(12) United States Patent  (10) Patent No.: US 7,912,574 B2
Wurman et al.  (45) Date of Patent: Mar. 22, 2011

(54) SYSTEM AND METHOD FOR TRANSPORTING INVENTORY ITEMS

(75) Inventors: Peter R. Wurman, Raleigh, NC (US); Raffaello D'Andrea, Ithaca, NY (US); Michael T. Barbehenn, Bedford, MA (US); Andrew E. Hoffman, Arlington, MA (US); Michael C. Mountz, Cambridge, MA (US)

(73) Assignee: Kiva Systems, Inc., North Reading, MA (US)

( * ) Notice: Subject to any disclaimer, the term of this patent is extended or adjusted under 35 U.S.C. 154(b) by 874 days.

(21) Appl. No.: 11/425,066

(22) Filed: Jun. 19, 2006

(65) Prior Publication Data

US 2007/0293978 A1 Dec. 20, 2007

(51) Int. Cl.
*G06F 7/00* (2006.01)
(52) U.S. Cl. .................. 700/213; 340/572.1; 705/28
(58) Field of Classification Search .......... 700/214, 700/213, 215, 216; 340/572.1; 705/28
See application file for complete search history.

(56) References Cited

U.S. PATENT DOCUMENTS

| | | |
|---|---|---|
| 3,689,106 A | 9/1972 | Young |
| 3,938,608 A | 2/1976 | Folco-Zambelli |
| 4,375,354 A | 3/1983 | Henriksson |
| 4,530,056 A | 7/1985 | MacKinnon et al. |
| 4,554,724 A | 11/1985 | Bantz |
| 4,562,635 A | 1/1986 | Carter |
| 4,630,216 A | 12/1986 | Tyler et al. |
| 4,779,203 A | 10/1988 | McClure et al. |
| 4,993,507 A | 2/1991 | Ohkura |
| 5,111,401 A | 5/1992 | Everett, Jr. et al. |
| 5,179,329 A | 1/1993 | Nishikawa et al. |
| 5,280,431 A | 1/1994 | Summerville et al. |
| 5,283,739 A | 2/1994 | Summerville et al. |
| 5,341,130 A | 8/1994 | Yardley et al. |
| 5,488,277 A | 1/1996 | Nishikawa et al. |
| 5,568,030 A | 10/1996 | Nishikawa et al. |
| 5,623,413 A | 4/1997 | Matheson et al. |
| 5,625,559 A | 4/1997 | Egawa |

(Continued)

FOREIGN PATENT DOCUMENTS

EP 1 118 573 A1 1/2001

(Continued)

OTHER PUBLICATIONS

PCT Notification of Transmittal of the International Search Report and the Written Opinion of the International Searching Authority, or the Declaration with attached International Search Report and Written Opinion of the International Searching Authority in International Application No. PCT/US 07/13450, Nov. 12, 2008, 9 pages.

(Continued)

*Primary Examiner* — Gene Crawford
*Assistant Examiner* — Ramya Prakasam
(74) *Attorney, Agent, or Firm* — Baker Botts L.L.P.

(57) ABSTRACT

A method for transporting inventory items includes moving a mobile drive unit to a first point within a workspace. The first point is a location of an inventory holder. The method further includes docking the mobile drive unit with the inventory holder and moving the mobile drive unit and the inventory holder to a second point within the workspace. The second point is associated with conveyance equipment. The method further includes moving the inventory holder to a third point within the workspace using the conveyance equipment.

18 Claims, 19 Drawing Sheets

U.S. PATENT DOCUMENTS

| | | | |
|---|---|---|---|
| 5,904,727 A | 5/1999 | Prabhakaran | |
| 5,928,294 A | 7/1999 | Zelinkovsky | |
| 6,138,064 A | 10/2000 | Matsumoto et al. | |
| 6,285,951 B1 | 9/2001 | Gaskins et al. | |
| 6,341,271 B1 | 1/2002 | Salvo et al. | 705/28 |
| 6,594,535 B1* | 7/2003 | Costanza | 700/97 |
| 6,600,418 B2 | 7/2003 | Francis et al. | 340/572.1 |
| 6,647,316 B2 | 11/2003 | Bahri et al. | |
| 6,652,213 B1 | 11/2003 | Mitchell et al. | 414/284 |
| 6,669,089 B2 | 12/2003 | Cybulski et al. | |
| 6,672,601 B1 | 1/2004 | Hofheins et al. | |
| 6,748,292 B2 | 6/2004 | Mountz | |
| 6,895,301 B2 | 5/2005 | Mountz | |
| 6,950,722 B2 | 9/2005 | Mountz | |
| 2002/0008005 A1 | 1/2002 | Eguchi | 198/617 |
| 2002/0154974 A1 | 10/2002 | Fukuda et al. | 414/416.01 |
| 2003/0218307 A1 | 11/2003 | Anderson et al. | |
| 2004/0010337 A1 | 1/2004 | Mountz | 700/214 |
| 2004/0153187 A1* | 8/2004 | Knight et al. | 700/99 |
| 2004/0203633 A1 | 10/2004 | Knauerhase et al. | |
| 2004/0238326 A1* | 12/2004 | Lichti | 198/475.1 |
| 2005/0080524 A1 | 4/2005 | Park | |
| 2005/0256639 A1 | 11/2005 | Aleksic et al. | |
| 2006/0089787 A1 | 4/2006 | Burr et al. | |
| 2006/0235557 A1* | 10/2006 | Knight et al. | 700/103 |
| 2007/0136152 A1 | 6/2007 | Dunsker et al. | |
| 2007/0198174 A1 | 8/2007 | Williams et al. | |
| 2007/0294029 A1 | 12/2007 | D'Andrea et al. | |
| 2008/0009965 A1 | 1/2008 | Bruemmer et al. | |
| 2008/0051984 A1 | 2/2008 | Wurman et al. | |
| 2008/0051985 A1* | 2/2008 | D'Andrea et al. | 701/200 |

FOREIGN PATENT DOCUMENTS

| | | |
|---|---|---|
| WO | WO 99/52091 | 10/1999 |
| WO | WO 2006/044108 A2 | 4/2006 |

OTHER PUBLICATIONS

PCT Invitation to Pay Additional Fees in International Application o. PCT/US2007/070742, dated Apr. 21, 2008, 5 pages.

European Patent Office Communication Pursuant to Article 94(3) EPC in EP Application No. 07 798 296.5-2206, dated Jul. 1, 2009, 3 pages.

U.S. Patent and Trademark Office Official Action dated Jun. 25, 2009 in U.S. Appl. No. 11/425,049, 16 pages.

"Vision—Cost of Ownership," *Frog Navigation Systems*, http://www.frog.nl/industry.php?f=cofo&s=vision, date unknown, 1 page.

"Vision—Reliability," *Frog Navigation Systems*, http://www.frog.nl/industry.php?f=reliability&s=vision, date unknown, 1 page.

"Vision—Availability," *Frog Navigation Systems*, http://www.frog.nl/industry.php?f=availability&s=vision, date unknown, 1 page.

"Technology—Vehicle Technology," *Frog Navigation Systems*, http://www.frog.nl/industry.php?f=vehicletech&s=technology, date unknown, 1 page.

"Technology—Supervisory Control System," *Frog Navigation Systems*, http://www.frog.nl/industry.php?f=superfrog&s=technology, date unknown, 1 page.

"Products—Box Runners," *Frog Navigation Systems*, http://www.frog.nl/industry.php?f=boxrunners&s=products.

"Products—Pallet Movers," *Frog Navigation Systems*, http://www.frog.nl/industry.php?f=palletmovers&s=products, date unknown, 1 page.

"Products—Special Carriers," *Frog Navigation Systems*, http://www.frog.nl/industry.php?f=specialcarriers&s=products, date unknown, 1 page.

"Company—Company Profile," *Frog Navigation Systems*, http://www.frog.nl/cargo.php, date unknown, 1 page.

"Box Runners," *Frog Navigation Systems*, http://www.frog.nl/img/visualarchive/pdf/BoxRunners.pdf, date unknown, 2 page.

Pallet Movers, *Frog Navigation Systems*, http://www.frog.nl/img/visualarchive/pdf/PalletMovers1.pdf, dated unknown, 2 pages.

"Special Carriers," *Frog Navigation Systems*, http://www.frog.nl/img/visualarchive/pdf/SpecialCarriers1.pdf, date unknown, 2 pages.

Special Carriers, *Frog Navigation Systems*, http://www.frog.nl/img/visualarchive/pdf/SpecialCarriers2.pdf, date unknown, 2 pages.

"Applications—Sony Disc Manufacturing," *Frog Navigation Systems*, http://www.frog.nl/industry.php?f=industrysony&s=applications, date unknown, 1 page.

"Applications—Hewlett Packard," *Frog Navigation Systems*, http://www.frog.nl/industry.php?f=industryhp&s=applications, date unknown, 1 page.

"Applications—Delphi Europe," *Frog Navigation Systems*, http://www.frog.nl/industry.php?f=industrydelphieurope&s=applications, date unknown, 1 page.

"Applications—Volkswagen," *Frog Navigation Systems*, http://www.frog.nl/industry.php?f=industryvw&s=applications, date unknown, 1 page.

"Applications—Delphi Automotive Systems," *Frog Navigation Systems*, http://www.frog.nl/industry.php?f=industrydelphi&s=applications, date unknown, 1 page.

"Applications—ACI Packaging," *Frog Navigation Systems*, http://www.frog.nl/industry.php?f=industryaci&s=applications, date unknown, 1 page.

"Applications—Nestlé Itancourt," *Frog Navigation Systems*, http://www.frog.nl/industry.php?f=industrynestle&s=applications, date unknown, 1 page.

"Applications—Corus," *Frog Navigation Systems*, http://www.frog.nl/industry.php?f=steelindustry&s=applications, date unknown, 1 page.

"Applications—Roto Smeets," *Frog Navigation Systems*, http://www.frog.nl/industry.php?f=paperprinting&s=applications, date unknown, 1 page.

"Applications—University Medical Center," *Frog Navigation Systems*, http://www.frog.nl/industry.php?f=medical-umc&s=applications, date unknown, 1 page.

"Applications—Pharma," *Frog Navigation Systems*, http://www.frog.nl/industry.php?f=medical-pharma&s=applications, date unknown, 1 pg.

"Applications—Nestor," *Frog Navigation Systems*, http://www.frog.nl/industry.php?f=nestor&s=research, date unknown, 1 page.

"Products—Container Carriers," *Frog Navigation Systems*, http://www.frog.nl/cargo.php?f=containercarriers&s=cproducts, date unknown, 1 page.

"Products—Parking Shuttle, "*Frog Navigation Systems*, http://www.frog.nl/cargo.php?f=pacvehicles&s=cproducts, date unknown, 1 page.

"Products—OLS Cargo Carriers," *Frog Navigation Systems*, http://www.frog.nl/cargo.php?f=olscargo&s=cproducts, date unknown, 1 page.

"Products—Park-a-Car," *Frog Navigation Systems*, http://www.frog.nl/cargo.php?f=parkacar&s=capplications, date unknown, 1 page.

"Applications—Europe Combined Terminal," *Frog Navigation Systems*, http://www.frog.nl/cargo.php?f=europecomter&s=capplications, date unknown, 1 page.

"Applications—OLS," *Frog Navigation Systems*,, http://www.frog.nl/cargo.php?f=ulogsys&s=capplications, date unknown, 1 page.

"Controler Units—FrogBox Light," *Frog Navigation Systems*, http://www.frog.nl/components.php?f=fboxlight&s=controllerunits, date unknown, 1 pg.

"Controller Units—FrogBox Aluminum," *Frog Navigation Systems*, http://www.frog.nl/components.php?f=fboxalu&s=controllerunits, date unknown, 1 pg.

"Calibration—Magnetruler," *Frog Navigation Systems*, http://www.frog.nl/components.php?f=magnetruler&s=calibration, date unknown, 1 pg.

"Safety—Bejo Sensor," *Frog Navigation Systems*, http://www.frog.nl/components.php?f=bejosensor&s=safety, date unknown, 1 pg.

"Communication—Hokuyo Infra Red," *Frog Navigation Systems*, http://www.frog.nl/components.php?f=hokuyo&s=communication, date unknown, 1 pg.

"Choppers—TwinDrive 30," *Frog Navigation Systems*, http://www.frog.nl/components.php?f=twindrive&s=choppers, date unknown, 1 page.

"Gyro—Frog Gyro MKII," *Frog Navigation Systems*, http://www.frog.nl/components.php?f=gyromk&s=gyro, date unknown, 1 page.

"Operator Devices—Frog Terminal," *Frog Navigation Systems*, http://www.frog.nl/components.php?f=frvehterm &s=operatordevices, 1 page.
*RibbIT*, No. 1, Frog Navigation Systems, online periodical, http://www.frog.nl/ribbit/ribbit-1-english.pdf, date unknown, 8 pages.
*RibbIT*, No. 2, Frog Navigation Systems, online periodical, http://www.frog.nl/ribbit/ribbit-2-english.pdf, date unknown, 8 pages.
*RibbIT*, No. 3, Frog Navigation Systems, online periodical, http://www.frog.nl/ribbit/Ribbit-3-English.pdf, date unknown, 8 pages.
*RibbIT*, No. 4, Frog Navigation Systems, online periodical, http://www.frog.nl/ribbit/Ribbit-3-English.pdf, date unknown, 8 pages.
*RibbIT*, No. 5, Frog Navigation Systems, online periodical, http://www.frog.nl/ribbit/ribbit-5-english.pdf, date unknown, 8 pages.
U.S. Appl. No. 11/425,042, entitled "System and Method for Managing Mobile Drive Units," filed Jun. 19, 2006, 125 pages.
U.S. Appl. No. 11/425,049, entitled, "System and Method for Positioning a Mobile Drive Unit," filed Jun. 19, 2006, 124 pages.
U.S. Appl. No. 11/425,057, entitled "System and Method from Generating a Path for a Mobile Drive Unit," filed Jun. 19, 2006, 113 pages.
U.S. Appl. No. 11/425,073, entitled "System and Method for Coordinating Movement of Mobile Drive Units," filed Jun. 19, 2006, 122 pages.
U.S. Appl. No. 11/425,076, entitled "System and Method for Maneuvering a Mobile Drive Unit," filed Jun. 19, 2006, 119 pages.
U.S. Patent and Trademark Official Action dated Dec. 17, 2009 in U.S. Appl. No. 11/425,049, 14 pages.
Sandt et al., "Perception for a Transport Robot in Public Environments," Proceedings IROS 97 0-7803-4119-8/97, IEEE Xplore, pp. 360-365, downloaded Mar. 31, 2009.
Groover, "Part II Material Handling and Identification Technologies, Introduction to Material Handling," Chapters 9 and 10, pp. 281-321, undated (Internet).
PCT Notification of Transmittal of the International Search Report and the Written Opinion of the International Searching Authority, or the Declaration in International Application No. PCT/US2007/070739, 10 pages, Apr. 3, 2008.
PCT Notification of the International Search Report and the Written Opinion of the International Searching Authority, or the Declaration with attached PCT International Search Report and Written Opinion of the International Searching Authority in International Application No. PCT/US2007/012952, 10 pgs, Sep. 19, 2008.
PCT Notification of Transmittal of International Search Report and the Written Opinion of the International Searching Authority, or the Declaration with attached International Search Report and the Written Opinion of the International Searching Authority in International Application No. PCT/US 07/70600, 7 pages, Oct. 15, 2008.
PCT Notification of Transmittal of International Search Report and the Written Opinion of the International Searching Authority, or the Declaration with attached International Search Report and the Written Opinion of the International Searching Authority in International Application No. PCT/US 07/12976, 11 pages, Nov. 10, 2008.
Communication Pursuant to Article 94(3) EPC in EP Application No. 07-798-295.7-2206, 5 pages, May 5, 2009.
U.S. Patent and Trademark Office, Official Action, U.S. Appl. No. 11/425,057, 15 pages, Apr. 7, 2009.
U.S. Patent and Trademark Office, Official Action, U.S. Appl. No. 11/425,076, 14 pages, Jun. 10, 2009.
U.S. Patent and Trademark Office, Official Action, U.S. Appl. No. 11/425,049, 12 pages, Jun. 25, 2009.
U.S. Patent and Trademark Office, Official Action, U.S. Appl. No. 11/425,042, 8 pages, Sep. 9, 2009.
U.S. Patent and Trademark Office, Official Action, U.S. Appl. No. 11/425,057, 14 pages, Sep. 18, 2009.
U.S. Patent and Trademark Office, Official Action, U.S. Appl. No. 11/425,073, 28 pages, Dec. 7, 2009.
U.S. Patent and Trademark Office, Official Action, U.S. Appl. No. 11/425,049, 13 pages, Dec. 17, 2009.
U.S. Patent and Trademark Office, Official Action, U.S. Appl. No. 11/425,076, 19 pages, Dec. 31, 2009.
U.S. Patent and Trademark Office, Official Action, U.S. Appl. No. 11/425,049, 16 pages, Apr. 13, 2010.
U.S. Patent and Trademark Office, Official Action, U.S. Appl. No. 11/425,057, 19 pages, May 27, 2010.
U.S. Patent and Trademark Office, Official Action, U.S. Appl. No. 11/425,076, Jul. 8, 2010.
U.S. Patent and Trademark Office, Official Action, U.S. Appl. No. 11/425,049, Sep. 27, 2010.
U.S. Patent and Trademark Office, Official Action, U.S. Appl. No. 11/425,057, May 27, 2010.
U.S. Patent and Trademark Office, Official Action, U.S. Appl. No. 11/425,073, Dec. 7, 2009.
U.S. Patent and Trademark Office, Official Action, U.S. Appl. No. 11/425,073, Jun. 29, 2010.

\* cited by examiner

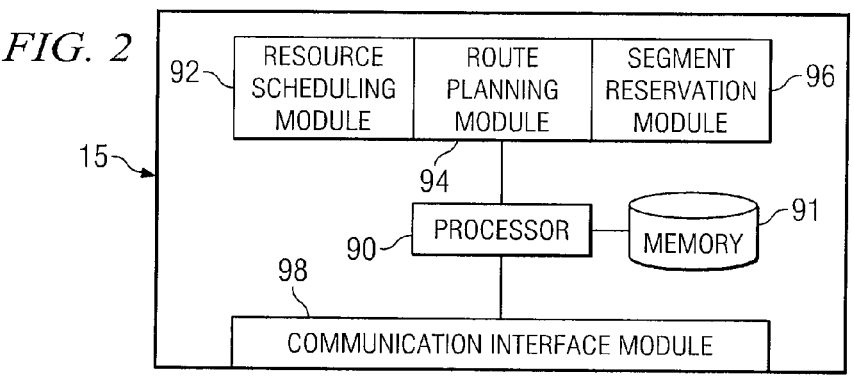
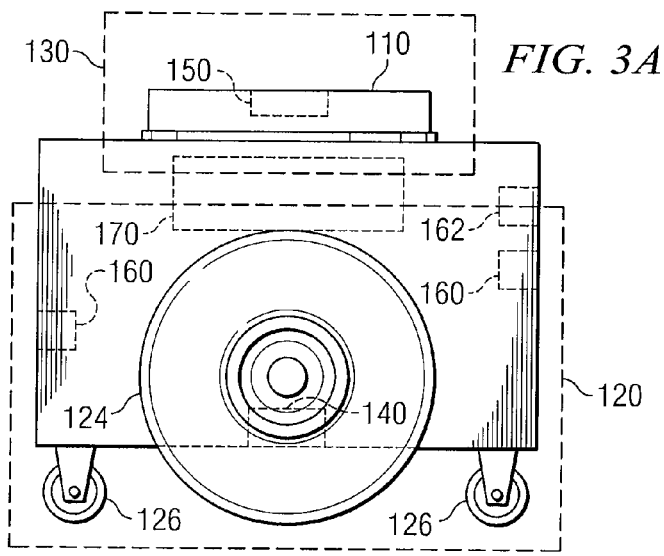
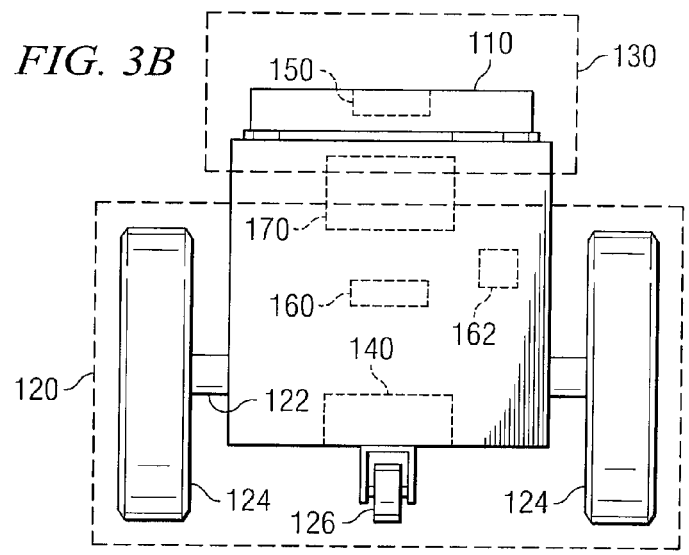

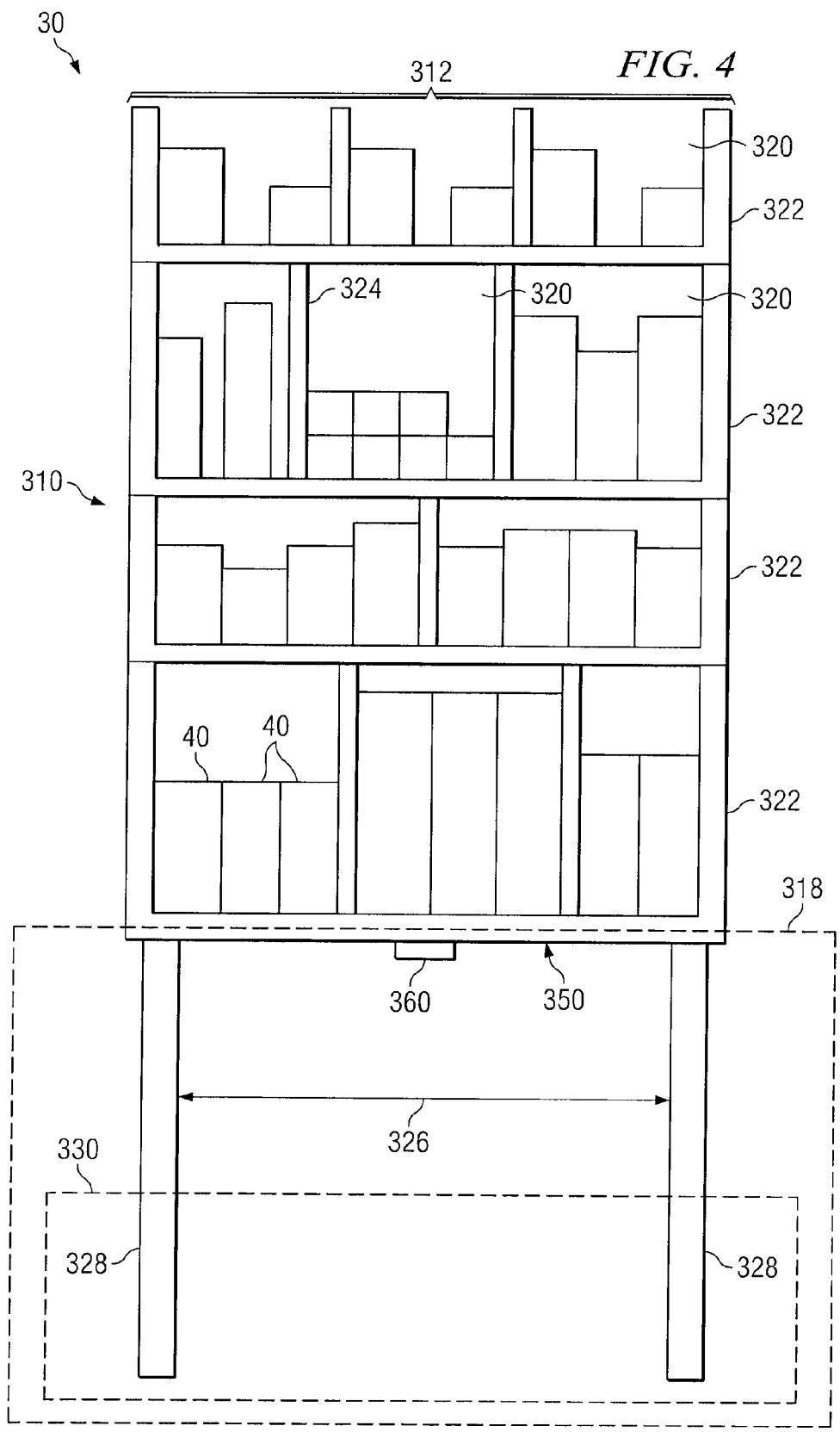

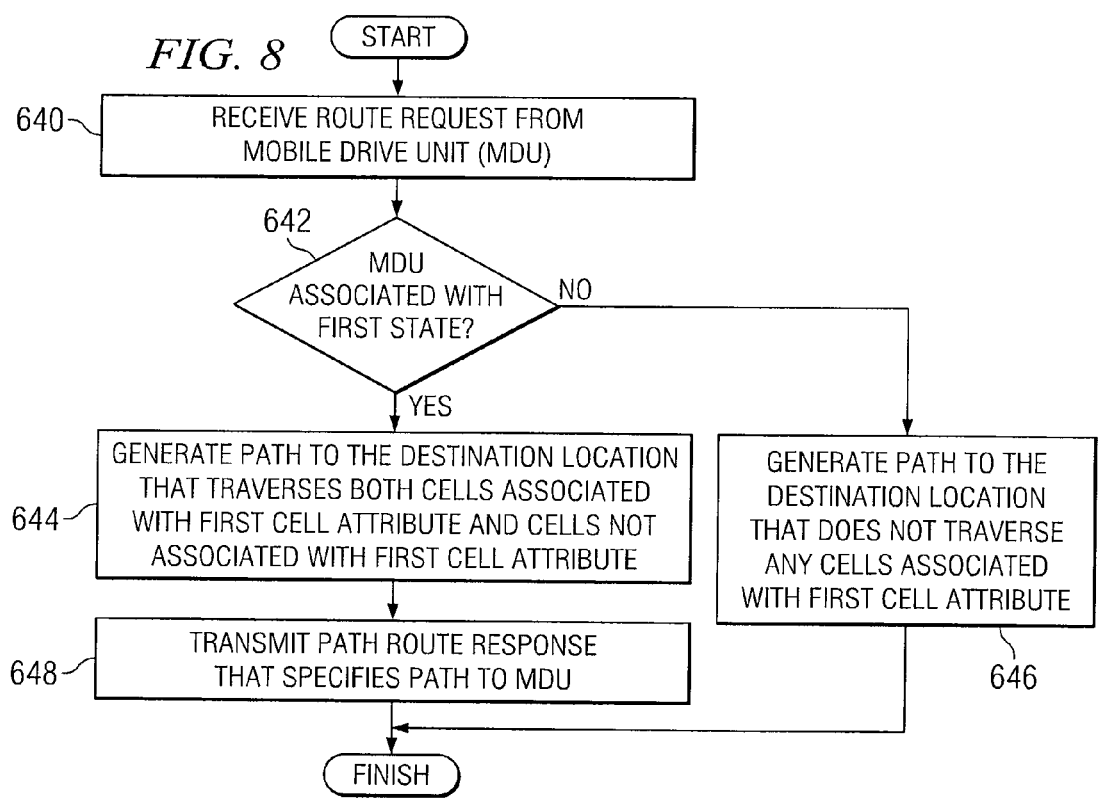
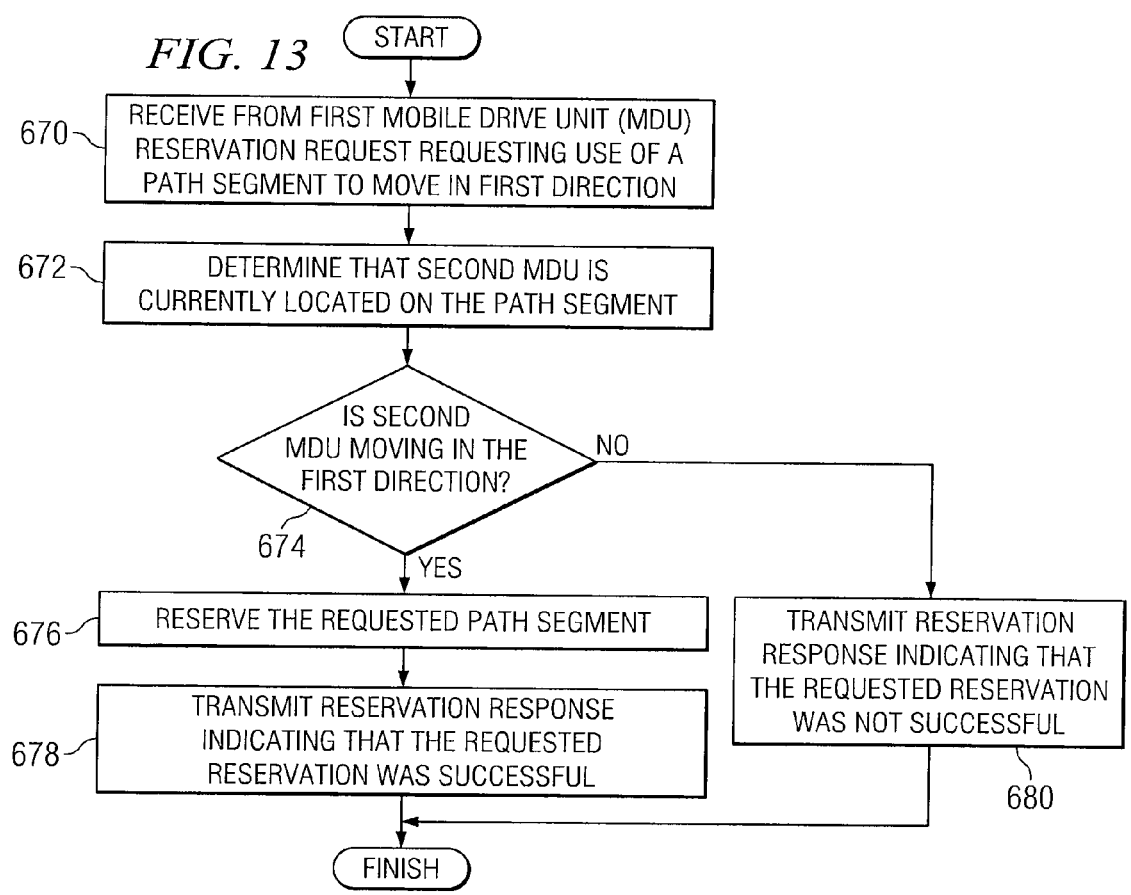

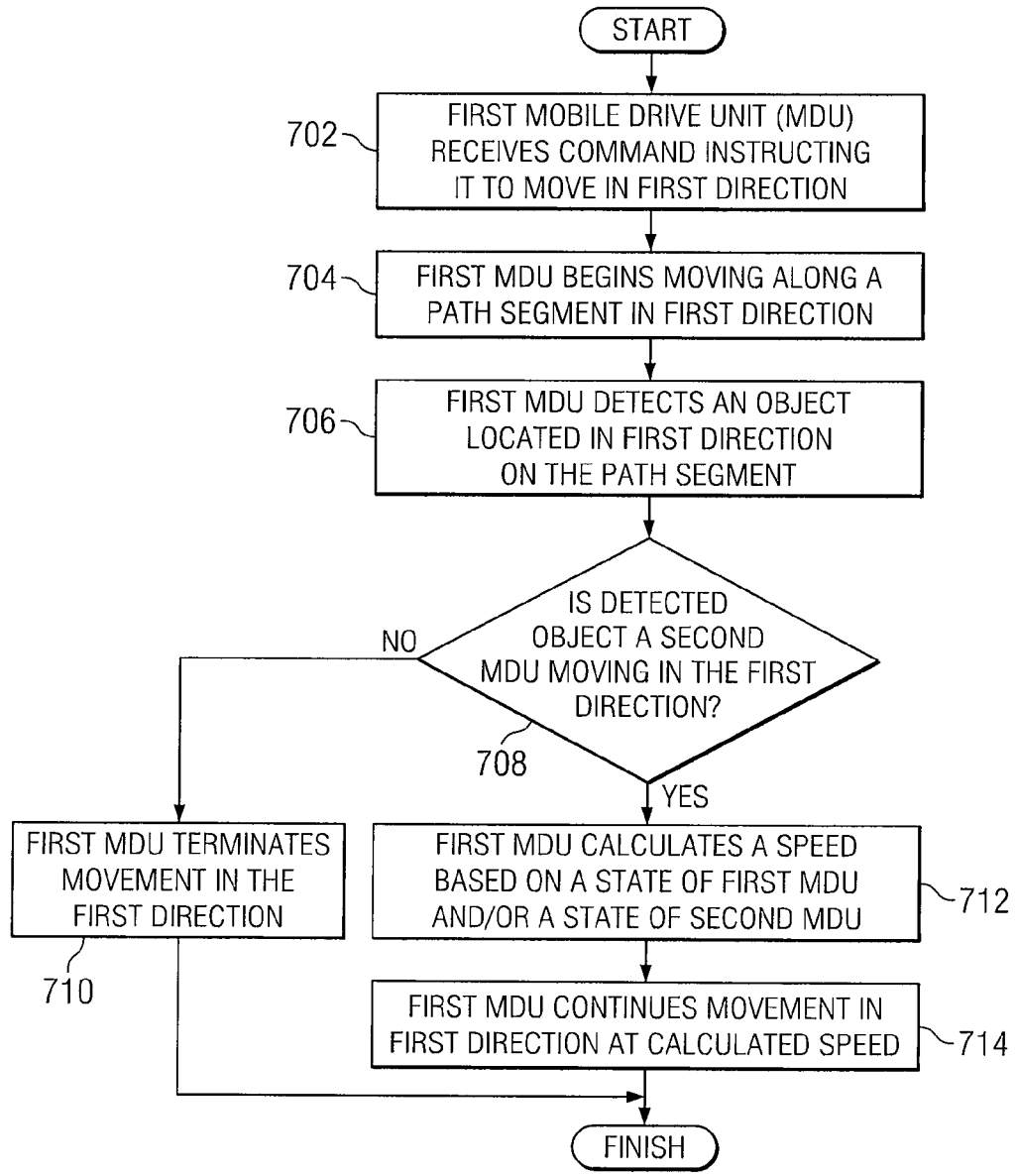

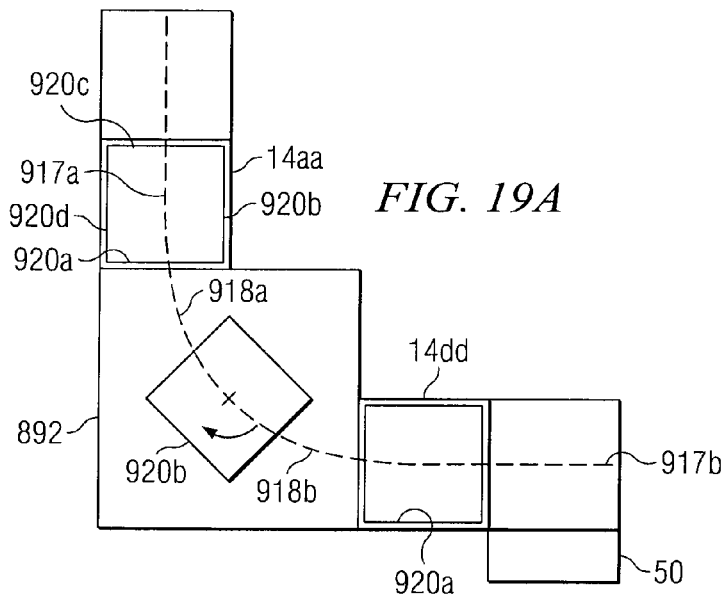
*FIG. 19A*
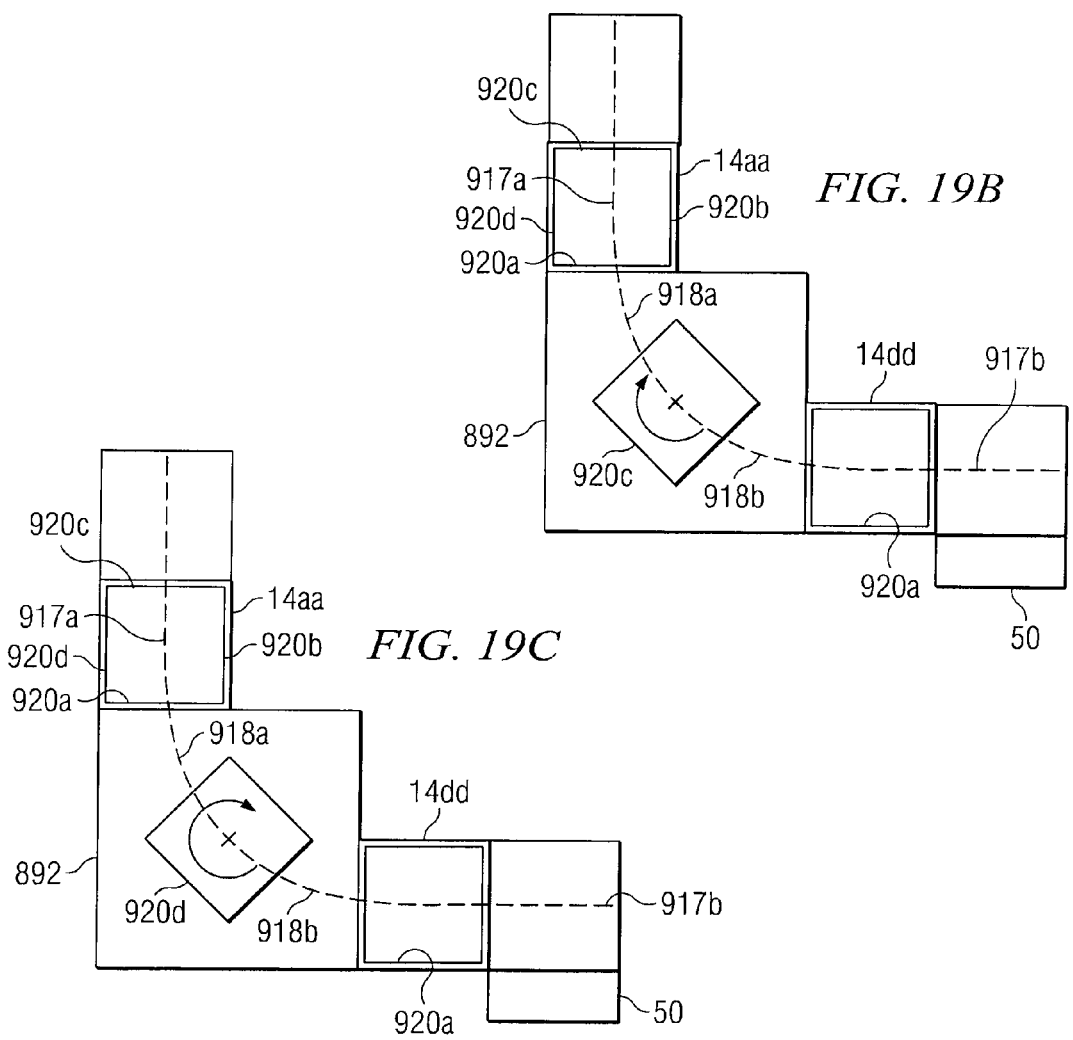
*FIG. 19B*
*FIG. 19C*

SYSTEM AND METHOD FOR TRANSPORTING INVENTORY ITEMS

TECHNICAL FIELD OF THE INVENTION

This invention relates in general to inventory systems, and more particularly to a method and system for efficient management of mobile drive units within an inventory system.

BACKGROUND OF THE INVENTION

Modern inventory systems, such as those in mail-order warehouses, supply chain distribution centers, airport luggage systems, and custom-order manufacturing facilities, face significant challenges in responding to requests for inventory items. As inventory systems grow, the challenges of simultaneously completing a large number of packing, storing, and other inventory-related tasks becomes non-trivial. In inventory systems tasked with responding to large numbers of diverse inventory requests, inefficient utilization of system resources, including space, equipment, and manpower, can result in lower throughput, unacceptably long response times, an ever-increasing backlog of unfinished tasks, and, in general, poor system performance. Additionally, expanding or reducing the size or capabilities of many inventory systems requires significant changes to existing infrastructure and equipment. As a result, the cost of incremental changes to capacity or functionality may be prohibitively expensive limiting the ability of the system to accommodate fluctuations in system throughput.

SUMMARY OF THE INVENTION

In accordance with the present invention, the disadvantages and problems associated with inventory storage have been substantially reduced or eliminated. In particular, a mobile inventory system is provided that includes one or more mobile drive units capable of moving any of one or more inventory holders between locations within a physical space associated with the mobile inventory system.

In accordance with one embodiment of the present invention, a method for transporting inventory items includes moving a mobile drive unit to a first point within a workspace. The first point is the location of an inventory holder. The method further includes docking the mobile drive unit with the inventory holder and moving the mobile drive unit and the inventory holder to a second point within the workspace. The second point is associated with conveyance equipment. The method further includes moving the inventory holder to a third point within the workspace using the conveyance equipment.

In accordance with another embodiment of the present invention, a system for transporting inventory items includes a plurality of inventory holders, a plurality of mobile drive units, and conveyance equipment. The inventory holders are capable of storing inventory items. The mobile drive units are each capable of moving to a first point, the first point being the location of one of the inventory holders. The mobile drive units are each further capable of docking with the inventory holder and moving the inventory holder to a second point, the second point being associated with the conveyance equipment. The conveyance equipment is capable of moving the inventory holder to a third point.

Technical advantages of certain embodiments of the present invention include the ability to optimize the use of space and equipment to complete inventory related-tasks. Additionally, particular embodiments may utilize a plurality of independently-operating drive units, each capable of accessing and moving a particular inventory item stored anywhere within the inventory system. Such a configuration may provide the ability for the inventory system to access in an arbitrary order any item stored in the system and allow for parallel completion of multiple inventory tasks in a system that is easily scalable and portable. Other technical advantages of certain embodiments of the present invention include providing a flexible and scalable inventory storage solution that can be easily adapted to accommodate system growth and modification and allocating system-level resources in an efficient manner to the completion of individual tasks.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present invention and its advantages, reference is now made to the following description, taken in conjunction with the accompanying drawings, in which:

FIG. 2 illustrates in greater detail the components of an example management module that may be utilized in particular embodiments of the inventory system shown in FIG. 1;

FIGS. 3A and 3B illustrate in greater detail an example mobile drive unit that may be utilized in particular embodiments of the inventory system shown in FIG. 1;

FIG. 4 illustrates in greater detail an example inventory holder that may be utilized in particular embodiments of the inventory system shown in FIG. 1;

FIG. 8 is a flowchart detailing example operation of a particular embodiment of the management module in implementing the techniques described in FIG. 7;

FIG. 13 is a flowchart detailing example operation of the management module in facilitating the coordinated movement illustrated in FIGS. 12A-12E;

FIG. 14 is a flowchart detailing example operation of a mobile drive unit in implementing the coordinated movement illustrated in FIGS. 12A-12E;

FIGS. 19A-19E illustrate example operation of a particular embodiment of mobile drive unit in utilizing a rotation area.

DETAILED DESCRIPTION OF THE INVENTION

Figure 1:
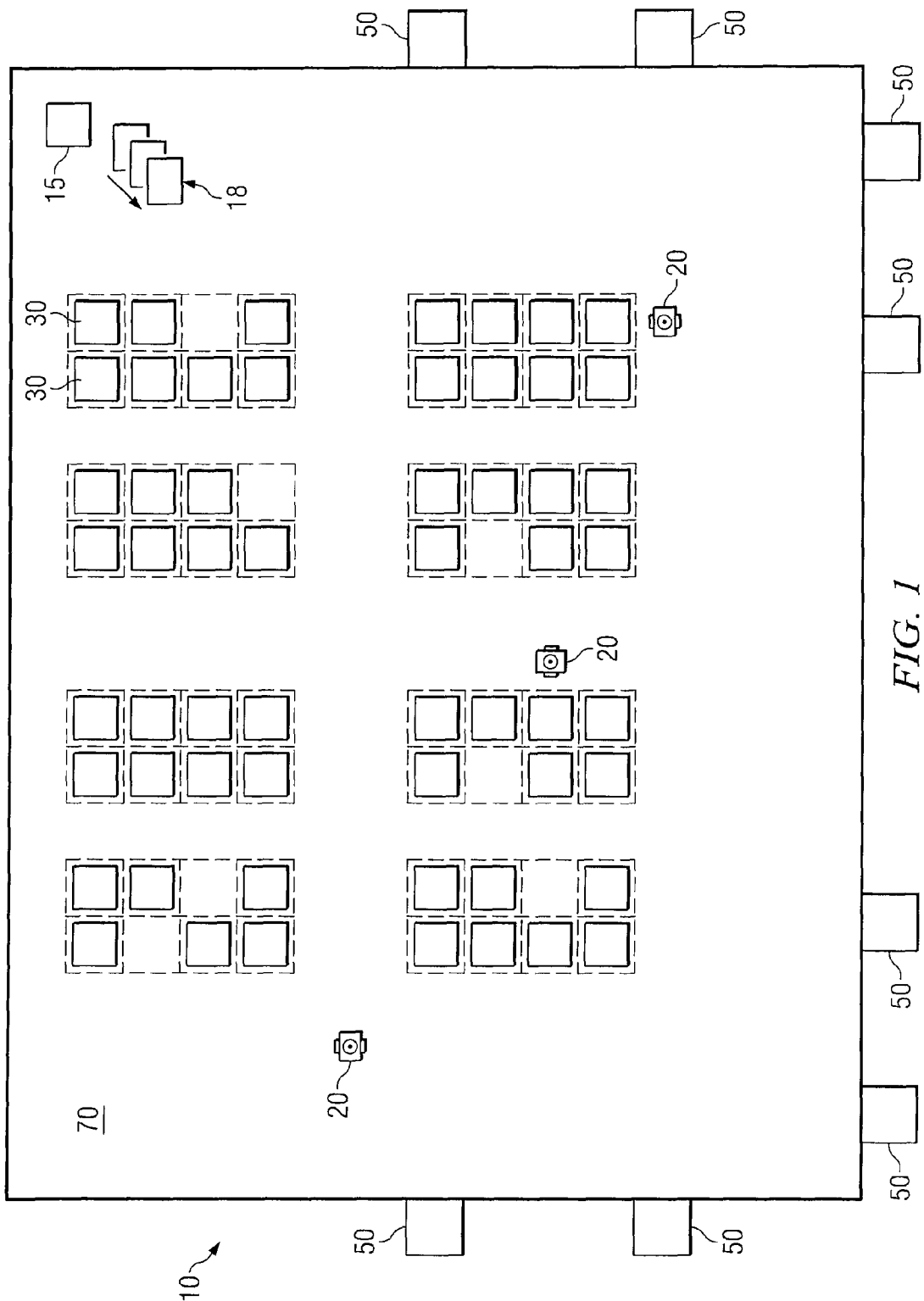
FIG. 1 illustrates components of an inventory system according to a particular embodiment.

FIG. 1 illustrates the contents of an inventory system 10. Inventory system 10 includes a management module 15, one or more mobile drive units 20, one or more inventory holders 30, and one or more inventory stations 50. Mobile drive units 20 transport inventory holders 30 between points within a workspace 70 in response to commands communicated by management module 15. Each inventory holder 30 stores one or more types of inventory items. As a result, inventory system 10 is capable of moving inventory items between locations within workspace 70 to facilitate the entry, processing, and/or removal of inventory items from inventory system 10 and the completion of other tasks involving inventory items.

Management module 15 assigns tasks to appropriate components of inventory system 10 and coordinates operation of the various components in completing the tasks. These tasks may relate not only to the movement and processing of inventory items, but also to the management and maintenance of the components of inventory system 10. For example, management module 15 may assign portions of workspace 70 as parking spaces for mobile drive units 20, the scheduled recharge or replacement of mobile drive unit batteries, the storage of empty inventory holders 30, or any other operations associated with the functionality supported by inventory system 10 and its various components. Management module 15 may select components of inventory system 10 to perform these tasks and communicate appropriate commands and/or data to the selected components to facilitate completion of these operations. Although shown in FIG. 1 as a single, discrete component, management module 15 may represent multiple components and may represent or include portions of mobile drive units 20 or other elements of inventory system 10. As a result, any or all of the interaction between a particular mobile drive unit 20 and management module 15 that is described below may, in particular embodiments, represent peer-to-peer communication between that mobile drive unit 20 and one or more other mobile drive units 20. The contents and operation of an example embodiment of management module 15 are discussed further below with respect to FIG. 2.

Mobile drive units 20 move inventory holders 30 between locations within workspace 70. Mobile drive units 20 may represent any devices or components appropriate for use in inventory system 10 based on the characteristics and configuration of inventory holders 30 and/or other elements of inventory system 10. In a particular embodiment of inventory system 10, mobile drive units 20 represent independent, self-powered devices configured to freely move about workspace 70. In alternative embodiments, mobile drive units 20 represent elements of a tracked inventory system 10 configured to move inventory holder 30 along tracks, rails, cables, crane system, or other guidance or support elements traversing workspace 70. In such an embodiment, mobile drive units 20 may receive power and/or support through a connection to the guidance elements, such as a powered rail. Additionally, in particular embodiments of inventory system 10 mobile drive units 20 may be configured to utilize alternative conveyance equipment to move within workspace 70 and/or between separate portions of workspace 70. The contents and operation of an example embodiment of a mobile drive unit 20 are discussed further below with respect to FIGS. 3A and 3B.

Additionally, mobile drive units 20 may be capable of communicating with management module 15 to receive information identifying selected inventory holders 30, transmit the locations of mobile drive units 20, or exchange any other suitable information to be used by management module 15 or mobile drive units 20 during operation. Mobile drive units 20 may communicate with management module 15 wirelessly, using wired connections between mobile drive units 20 and management module 15, and/or in any other appropriate manner. As one example, particular embodiments of mobile drive unit 20 may communicate with management module 15 and/or with one another using 802.11, Bluetooth, or Infrared Data Association (IrDA) standards, or any other appropriate wireless communication protocol. As another example, in a tracked inventory system 10, tracks or other guidance elements upon which mobile drive units 20 move may be wired to facilitate communication between mobile drive units 20 and other components of inventory system 10. Furthermore, as noted above, management module 15 may include components of individual mobile drive units 20. Thus, for the purposes of this description and the claims that follow, communication between management module 15 and a particular mobile drive unit 20 may represent communication between components of a particular mobile drive unit 20. In general, mobile drive units 20 may be powered, propelled, and controlled in any manner appropriate based on the configuration and characteristics of inventory system 10.

Inventory holders 30 store inventory items. In a particular embodiment, inventory holders 30 include multiple storage bins with each storage bin capable of holding one or more types of inventory items. Inventory holders 30 are capable of being carried, rolled, and/or otherwise moved by mobile drive units 20. In particular embodiments, inventory holder 30 may provide additional propulsion to supplement that provided by mobile drive unit 20 when moving inventory holder 30.

Additionally, each inventory holder 30 may include a plurality of faces, and each bin may be accessible through one or more faces of the inventory holder 30. For example, in a particular embodiment, inventory holder 30 includes four faces. In such an embodiment, bins located at a corner of two faces may be accessible through either of those two faces, while each of the other bins is accessible through an opening in one of the four faces. Mobile drive unit 20 may be configured to rotate inventory holder 30 at appropriate times to present a particular face and the bins associated with that face to an operator or other components of inventory system 10.

The contents and operation of an example embodiment of an inventory holder 30 are discussed further below with respect to FIG. 4.

Inventory items represent any objects suitable for storage, retrieval, and/or processing in an automated inventory system 10. For the purposes of this description, "inventory items" may represent any one or more objects of a particular type that are stored in inventory system 10. Thus, a particular inventory holder 30 is currently "storing" a particular inventory item if the inventory holder 30 currently holds one or more units of that type. As one example, inventory system 10 may represent a mail order warehouse facility, and inventory items may represent merchandise stored in the warehouse facility. During operation, mobile drive units 20 may retrieve inventory holders 30 containing one or more inventory items requested in an order to be packed for delivery to a customer or inventory holders 30 carrying pallets containing aggregated collections of inventory items for shipment. Moreover, in particular embodiments of inventory system 10, boxes containing completed orders may themselves represent inventory items.

As another example, inventory system 10 may represent a merchandise-return facility. In such an embodiment, inventory items may represent merchandise returned by customers. Units of these inventory items may be stored in inventory holders 30 when received at the facility. At appropriate times, a large number of units may be removed from a particular inventory holder 30 and packed for shipment back to a warehouse or other facility. For example, individual units of a particular inventory item may be received and stored in inventory holders 30 until a threshold number of units of that inventory item have been received. Mobile drive unit 20 may be tasked with retrieving an inventory holder 30 in this state. A pallet may then be packed with inventory items removed from that inventory holder 30 and shipped to another facility, such as a mail-order warehouse.

As another example, inventory system 10 may represent an airport luggage facility. In such an embodiment, inventory items may represent pieces of luggage stored in the luggage facility. Mobile drive units 20 may retrieve inventory holders 30 storing luggage arriving and/or departing on particular flights or luggage destined for particular types of processing, such as x-ray or manual searching.

As yet another example, inventory system 10 may represent a manufacturing facility, and inventory items may represent individual components of a manufacturing kit. More specifically, inventory items may represent components intended for inclusion in an assembled product, such as electronic components for a customized computer system. In such an embodiment, inventory system 10 may retrieve particular components identified by a specification associated with an order for the product so that a customized version of the product can be built. Although a number of example embodiments are described, inventory system 10 may, in general, represent any suitable facility or system for storing and processing inventory items, and inventory items may represent objects of any type suitable for storage, retrieval, and/or processing in a particular inventory system 10.

In particular embodiments, inventory system 10 may also include one or more inventory stations 50. Inventory stations 50 represent locations designated for the completion of particular tasks involving inventory items. Such tasks may include the removal of inventory items from inventory holders 30, the introduction of inventory items into inventory holders 30, the counting of inventory items in inventory holders 30, the decomposition of inventory items (e.g. from pallet- or case-sized groups to individual inventory items), and/or the processing or handling of inventory items in any other suitable manner. In particular embodiments, inventory stations 50 may just represent the physical locations where a particular task involving inventory items can be completed within workspace 70. In alternative embodiments, inventory stations 50 may represent both the physical location and also any appropriate equipment for processing or handling inventory items, such as scanners for monitoring the flow of inventory items in and out of inventory system 10, communication interfaces for communicating with management module 15, and/or any other suitable components. Inventory stations 50 may be controlled, entirely or in part, by human operators or may be fully automated. Moreover, the human or automated operators of inventory stations 50 may be capable of performing certain tasks to inventory items, such as packing or counting inventory items, as part of the operation of inventory system 10.

Workspace 70 represents an area associated with inventory system 10 in which mobile drive units 20 can move and/or inventory holders 30 can be stored. For example, workspace 70 may represent all or part of the floor of a mail-order warehouse in which inventory system 10 operates. Although FIG. 1 shows, for the purposes of illustration, an embodiment of inventory system 10 in which workspace 70 includes a fixed, predetermined, and finite physical space, particular embodiments of inventory system 10 may include mobile drive units 20 and inventory holders 30 that are configured to operate within a workspace 70 that is of variable dimensions and/or an arbitrary geometry. While FIG. 1 illustrates a particular embodiment of inventory system 10 in which workspace 70 is entirely enclosed in a building, alternative embodiments may utilize workspaces 70 in which some or all of the workspace 70 is located outdoors, within a vehicle (such as a cargo ship), or otherwise unconstrained by any fixed structure.

Moreover, in particular embodiments, workspace 70 may include multiple portions that are physically separated from one another, including but not limited to separate floors, rooms, buildings, and/or portions divided in any other suitable manner. Mobile drive units 20 may be configured to utilize alternative conveyance equipment such as vertical or horizontal conveyors, trucks, ferries, gondolas, escalators, and/or other appropriate equipment suitable to convey mobile drive units 20 between separate portions of workspace 70.

In particular embodiments, as discussed in greater detail below with respect to FIG. 5, workspace 70 is associated with a grid (shown in FIG. 5 as grid 12) that connects a plurality of points within workspace 70. This grid may divide workspace 70 into a number of portions referred to as cells 14. Cells 14 may square, rectangular, polygonal, and/or of any other appropriate shape. In particular embodiments, workspace 70 may be portioned so that cells 14 have dimensions slightly larger than inventory holders 30. This may allow inventory system 10 to utilize a workspace 70 of minimal size without collisions occurring between inventory holders 30 being transported through neighboring cells 14. In general, however, cells 14 may sized in any manner appropriate based on the configuration and characteristics of the components of inventory system 10. Additionally, workspace 70 may utilize an irregular grid 12 in which size and/or shape may vary from cell 14 to cell 14.

In operation, management module 15 selects appropriate components to complete particular tasks and transmits task assignments 18 to the selected components to trigger completion of the relevant tasks. Each task assignment 18 defines one or more tasks to be completed by a particular component. These tasks may relate to the retrieval, storage, replenishment, and counting of inventory items and/or the management of mobile drive units 20, inventory holders 30, inventory stations 50 and other components of inventory system 10. Depending on the component and the task to be completed, a particular task assignment 18 may identify locations, components, and/or actions associated with the corresponding task and/or any other appropriate information to be used by the relevant component in completing the assigned task.

In particular embodiments, management module 15 generates task assignments 18 based, in part, on inventory requests that management module 15 receives from other components of inventory system 10 and/or from external components in communication with management module 15. These inventory requests identify particular operations to be completed involving inventory items stored or to be stored within inventory system 10 and may represent communication of any suitable form. For example, in particular embodiments, an inventory request may represent a shipping order specifying particular inventory items that have been purchased by a customer and that are to be retrieved from inventory system 10 for shipment to the customer. Management module 15 may also generate task assignments 18 independently of such inventory requests, as part of the overall management and maintenance of inventory system 10. For example, management module 15 may generate task assignments 18 in response to the occurrence of a particular event (e.g., in response to a mobile drive unit 20 requesting a space to park), according to a predetermined schedule (e.g., as part of a daily start-up routine), or at any appropriate time based on the configuration and characteristics of inventory system 10. After generating one or more task assignments 18, management module 15 transmits the generated task assignments 18 to appropriate components for completion of the corresponding task. The relevant components then execute their assigned tasks.

With respect to mobile drive units 20 specifically, management module 15 may, in particular embodiments, communicate task assignments 18 to selected mobile drive units 20 that identify one or more destinations for the selected mobile drive units 20. Management module 15 may select a mobile drive unit 20 to assign the relevant task based on the location or state of the selected mobile drive unit 20, an indication that the selected mobile drive unit 20 has completed a previously-assigned task, a predetermined schedule, and/or any other suitable consideration. These destinations may be associated with an inventory request the management module 15 is executing or a management objective the management module 15 is attempting to fulfill. For example, the task assignment may define the location of an inventory holder 30 to be retrieved, an inventory station 50 to be visited, a storage location where the mobile drive unit 20 should park until receiving another task, or a location associated with any other task appropriate based on the configuration, characteristics, and/or state of inventory system 10, as a whole, or individual components of inventory system 10. For example, in particular embodiments, such decisions may be based on the popularity of particular inventory items, the staffing of a particular inventory station 50, the tasks currently assigned to a particular mobile drive unit 20, and/or any other appropriate considerations.

As part of completing these tasks mobile drive units 20 may dock with and transport inventory holders 30 within workspace 70. Mobile drive units 20 may dock with inventory holders 30 by connecting to, lifting, and/or otherwise interacting with inventory holders 30 in any other suitable manner so that, when docked, mobile drive units 20 are coupled to and/or support inventory holders 30 and can move inventory holders 30 within workspace 70. While the description below focuses on particular embodiments of mobile drive unit 20 and inventory holder 30 that are configured to dock in a particular manner, alternative embodiments of mobile drive unit 20 and inventory holder 30 may be configured to dock in any manner suitable to allow mobile drive unit 20 to move inventory holder 30 within workspace 70. Additionally, as noted below, in particular embodiments, mobile drive units 20 represent all or portions of inventory holders 30. In such embodiments, mobile drive units 20 may not dock with inventory holders 30 before transporting inventory holders 30 and/or mobile drive units 20 may each remain continually docked with a particular inventory holder 30.

While the appropriate components of inventory system 10 complete assigned tasks, management module 15 may interact with the relevant components to ensure the efficient use of space, equipment, manpower, and other resources available to inventory system 10. As one specific example of such interaction, management module 15 is responsible, in particular embodiments, for planning the paths mobile drive units 20 take when moving within workspace 70 and for allocating use of a particular portion of workspace 70 to a particular mobile drive unit 20 for purposes of completing an assigned task. In such embodiments, mobile drive units 20 may, in response to being assigned a task, request a path to a particular destination associated with the task. Moreover, while the description below focuses on one or more embodiments in which mobile drive unit 20 requests paths from management module 15, mobile drive unit 20 may, in alternative embodiments, generate its own paths.

Management module 15 may select a path between the current location of the requesting mobile drive unit 20 and the requested destination and communicate information identifying this path to the mobile drive unit 20. Management module 15 may utilize knowledge of current congestion, historical traffic trends, task prioritization, and/or other appropriate considerations to select an optimal path for the requesting mobile drive unit 20 to take in getting to the destination. Additionally, in planning the path (or in assigning tasks), management module 15 may make informed decisions regarding the use of lifts, conveyors, ramps, tunnels, and/or other conveyance equipment or features of workspace 70 to facilitate the movement of the relevant mobile drive unit 20, as discussed below with respect to FIGS. 15-17.

After receiving a path from management module 15, the requesting mobile drive unit 20 may then move to the destination, traversing the path in a segment-by-segment manner. Before beginning a particular segment, the relevant mobile drive unit 20 may request permission to use the segment from management module 15. As a result, management module 15 may reserve the segment for use of that mobile drive unit 20. As a result, management module 15 may also be responsible for resolving competing requests to the use of a particular portion of workspace 70. An example implementation of this process is discussed in greater detail below in conjunction with FIG. 5.

In addition, components of inventory system 10 may provide information to management module 15 regarding their current state, other components of inventory system 10 with which they are interacting, and/or other conditions relevant to the operation of inventory system 10. This may allow management module 15 to utilize feedback from the relevant components to update algorithm parameters, adjust policies, or otherwise modify its decision-making to respond to changes in operating conditions or the occurrence of particular events.

In addition, while management module 15 may be configured to manage various aspects of the operation of the components of inventory system 10, in particular embodiments, the components themselves may also be responsible for decision-making relating to certain aspects of their operation, thereby reducing the processing load on management module 15. In particular, individual components may be configured to independently respond to certain localized circumstances in a manner that allows these components to improve their effectiveness without reducing the overall efficiency of inventory system 10. As one example, under certain conditions, management module 15 may modify its policies regarding segment reservations to permit the simultaneous movement of multiple mobile drive units 20 in a particular cell 14 of workspace 70, allowing the relevant mobile drive units 20 to operate in closer proximity to one another than would otherwise be permitted. When operating under such conditions, management module 15 may rely on the independent decision-making of the mobile drive units 20 to prevent collisions. FIGS. 12A-12E, 13, and 14 illustrate an example of mobile drive units 20 operating under such conditions.

Thus, based on its knowledge of the location, current state, and/or other characteristics of the various components of inventory system 10 and an awareness of all the tasks currently being completed, management module 15 can generate tasks, allot usage of system resources, and otherwise direct the completion of tasks by the individual components in a manner that optimizes operation from a system-wide perspective. Moreover, by relying on a combination of both centralized, system-wide management and localized, component-specific decision-making, particular embodiments of inventory system 10 may be able to support a number of techniques for efficiently executing various aspects of the operation of inventory system 10. As a result, particular embodiments of management module 15 may, by implementing one or more management techniques described below, enhance the efficiency of inventory system 10 and/or provide other operational benefits.

FIGS. 2-4 illustrate in greater detail the contents of particular embodiments of management module 15, mobile drive unit 20, and inventory holder 30, respectively. FIGS. 5-20 illustrate examples of specific management techniques that may be supported by certain embodiments of inventory system 10. Although FIGS. 2-4 describe particular example embodiments of management module 15, mobile drive unit 20, and inventory holder 30 the techniques described with respect to FIGS. 5-20 may be utilized in inventory systems 10 utilizing any appropriate type of components.

FIG. 2 illustrates in greater detail the components of a particular embodiment of management module 15. As shown, the example embodiment includes a resource scheduling module 92, a route planning module 94, a segment reservation module 96, a communication interface module 98, a processor 90, and a memory 91. Management module 15 may represent a single component, multiple components located at a central location within inventory system 10, or multiple components distributed throughout inventory system 10. For example, management module 15 may represent components of one or more mobile drive units 20 that are capable of communicating information between the mobile drive units 20 and coordinating the movement of mobile drive units 20 within workspace 70. In general, management module 15 may include any appropriate combination of hardware and/or software suitable to provide the described functionality.

Processor 90 is operable to execute instructions associated with the functionality provided by management module 15. Processor 90 may comprise one or more general purpose computers, dedicated microprocessors, or other processing devices capable of communicating electronic information. Examples of processor 90 include one or more application-specific integrated circuits (ASICs), field-programmable gate arrays (FPGAs), digital signal processors (DSPs) and any other suitable specific or general purpose processors.

Memory 91 stores processor instructions, inventory requests, reservation information, state information for the various components of inventory system 10 and/or any other appropriate values, parameters, or information utilized by management module 15 during operation. Memory 91 may represent any collection and arrangement of volatile or non-volatile, local or remote devices suitable for storing data. Examples of memory 91 include, but are not limited to, random access memory (RAM) devices, read only memory (ROM) devices, magnetic storage devices, optical storage devices, or any other suitable data storage devices.

Resource scheduling module 92 processes received inventory requests and generates one or more assigned tasks to be completed by the components of inventory system 10. Resource scheduling module 92 may also select one or more appropriate components for completing the assigned tasks and, using communication interface module 98, communicate the assigned tasks to the relevant components. Additionally, resource scheduling module 92 may also be responsible for generating assigned tasks associated with various management operations, such as prompting mobile drive units 20 to recharge batteries or have batteries replaced, instructing inactive mobile drive units 20 to park in a location outside the anticipated traffic flow or a location near the anticipated site of future tasks, and/or directing mobile drive units 20 selected for repair or maintenance to move towards a designated maintenance station.

Route planning module 94 receives route requests from mobile drive units 20. These route requests identify one or more destinations associated with a task the requesting mobile drive unit 20 is executing. In response to receiving a route request, route planning module 94 generates a path to one or more destinations identified in the route request. Route planning module 94 may implement any appropriate algorithms utilizing any appropriate parameters, factors, and/or considerations to determine the appropriate path. After generating an appropriate path, route planning module 94 transmits a route response identifying the generated path to the requesting mobile drive unit 20 using communication interface module 98. This process is discussed in greater detail below with respect to FIG. 5.

Segment reservation module 96 receives reservation requests from mobile drive units 20 attempting to move along paths generated by route planning module 94. These reservation requests request the use of a particular portion of workspace 70 (referred to herein as a "segment") to allow the requesting mobile drive unit 20 to avoid collisions with other mobile drive units 20 while moving across the reserved segment. In response to received reservation requests, segment reservation module 96 transmits a reservation response granting or denying the reservation request to the requesting mobile drive unit 20 using the communication interface module 98. This process is also discussed in greater detail below with respect to FIG. 5.

Communication interface module 98 facilitates communication between management module 15 and other components of inventory system 10, including reservation responses, reservation requests, route requests, route responses, and task assignments. These reservation responses, reservation requests, route requests, route responses, and task assignments may represent communication of any form appropriate based on the capabilities of management module 15 and may include any suitable information. Depending on the configuration of management module 15, communication interface module 98 may be responsible for facilitating either or both of wired and wireless communication between management module 15 and the various components of inventory system 10. In particular embodiments, management module 15 may communicate using communication protocols such as 802.11, Bluetooth, or Infrared Data Association (IrDA) standards. Furthermore, management module 15 may, in particular embodiments, represent a portion of mobile drive unit 20 or other components of inventory system 10. In such embodiments, communication interface module 98 may facilitate communication between management module 15 and other parts of the same system component.

In general, resource scheduling module 92, route planning module 94, segment reservation module 96, and communication interface module 98 may each represent any appropriate hardware and/or software suitable to provide the described functionality. In addition, as noted above, management module 15 may, in particular embodiments, represent multiple different discrete components and any or all of resource scheduling module 92, route planning module 94, segment reservation module 96, and communication interface module 98 may represent components physically separate from the remaining elements of management module 15. Moreover, any two or more of resource scheduling module 92, route planning module 94, segment reservation module 96, and communication interface module 98 may share common components. For example, in particular embodiments, resource scheduling module 92, route planning module 94, segment reservation module 96 represent computer processes executing on processor 90 and communication interface module 98 comprises a wireless transmitter, a wireless receiver, and a related computer process executing on processor 90.

FIGS. 3A and 3B illustrate in greater detail the components of a particular embodiment of mobile drive unit 20. In particular, FIGS. 3A and 3B include a front and side view of an example mobile drive unit 20. Mobile drive unit 20 includes a docking head 110, a drive module 120, a docking actuator 130, and a control module 170. Additionally, mobile drive unit 20 may include one or more sensors configured to detect or determine the location of mobile drive unit 20, inventory holder 30, and/or other appropriate elements of inventory system 10. In the illustrated embodiment, mobile drive unit 20 includes a position sensor 140, a holder sensor 150, an obstacle sensor 160, and an identification signal transmitter 162.

Docking head 110, in particular embodiments of mobile drive unit 20, couples mobile drive unit 20 to inventory holder 30 and/or supports inventory holder 30 when mobile drive unit 20 is docked to inventory holder 30. Docking head 110 may additionally allow mobile drive unit 20 to maneuver inventory holder 30, such as by lifting inventory holder 30, propelling inventory holder 30, rotating inventory holder 30, and/or moving inventory holder 30 in any other appropriate manner. Docking head 110 may also include any appropriate combination of components, such as ribs, spikes, and/or corrugations, to facilitate such manipulation of inventory holder 30. For example, in particular embodiments, docking head 110 may include a high-friction portion that abuts a portion of inventory holder 30 while mobile drive unit 20 is docked to inventory holder 30. In such embodiments, frictional forces created between the high-friction portion of docking head 110 and a surface of inventory holder 30 may induce translational and rotational movement in inventory holder 30 when docking head 110 moves and rotates, respectively. As a result, mobile drive unit 20 may be able to manipulate inventory holder 30 by moving or rotating docking head 110, either independently or as a part of the movement of mobile drive unit 20 as a whole.

Drive module 120 propels mobile drive unit 20 and, when mobile drive unit 20 and inventory holder 30 are docked, inventory holder 30. Drive module 120 may represent any appropriate collection of components operable to propel drive module 120. For example, in the illustrated embodiment, drive module 120 includes motorized axle 122, a pair of motorized wheels 124, and a pair of stabilizing wheels 126. One motorized wheel 124 is located at each end of motorized axle 122, and one stabilizing wheel 126 is positioned at each end of mobile drive unit 20.

Docking actuator 130 moves docking head 110 towards inventory holder 30 to facilitate docking of mobile drive unit 20 and inventory holder 30. Docking actuator 130 may also be capable of adjusting the position or orientation of docking head 110 in other suitable manners to facilitate docking. Docking actuator 130 may include any appropriate components, based on the configuration of mobile drive unit 20 and inventory holder 30, for moving docking head 110 or otherwise adjusting the position or orientation of docking head 110. For example, in the illustrated embodiment, docking actuator 130 includes a motorized shaft (not shown) attached to the center of docking head 110. The motorized shaft is operable to lift docking head 110 as appropriate for docking with inventory holder 30.

Drive module 120 may be configured to propel mobile drive unit 20 in any appropriate manner. For example, in the illustrated embodiment, motorized wheels 124 are operable to rotate in a first direction to propel mobile drive unit 20 in a forward direction. Motorized wheels 124 are also operable to rotate in a second direction to propel mobile drive unit 20 in a backward direction. In the illustrated embodiment, drive module 120 is also configured to rotate mobile drive unit 20 by rotating motorized wheels 124 in different directions from one another or by rotating motorized wheels 124 at different speed from one another.

Position sensor 140 represents one or more sensors, detectors, or other components suitable for determining the location of mobile drive unit 20 in any appropriate manner. For example, in particular embodiments, the workspace 70 associated with inventory system 10 includes a number of fiducial marks that mark points on a two-dimensional grid that covers all or a portion of workspace 70. In such embodiments, position sensor 140 may include a camera and suitable image- and/or video-processing components, such as an appropriately-programmed digital signal processor, to allow position sensor 140 to detect fiducial marks within the camera's field of view. Control module 170 may store location information that position sensor 140 updates as position sensor 140 detects fiducial marks. As a result, position sensor 140 may utilize fiducial marks to maintain an accurate indication of the location mobile drive unit 20 and to aid in navigation when moving within workspace 70.

Holder sensor 150 represents one or more sensors, detectors, or other components suitable for detecting inventory holder 30 and/or determining, in any appropriate manner, the location of inventory holder 30, as an absolute location or as a position relative to mobile drive unit 20. Holder sensor 150 may be capable of detecting the location of a particular portion of inventory holder 30 or inventory holder 30 as a whole. Mobile drive unit 20 may then use the detected information for docking with or otherwise interacting with inventory holder 30.

Obstacle sensor 160 represents one or more sensors capable of detecting objects located in one or more different directions in which mobile drive unit 20 is capable of moving. Obstacle sensor 160 may utilize any appropriate components and techniques, including optical, radar, sonar, pressure-sensing and/or other types of detection devices appropriate to detect objects located in the direction of travel of mobile drive unit 20. In particular embodiments, obstacle sensor 160 may transmit information describing objects it detects to control module 170 to be used by control module 170 to identify obstacles and to take appropriate remedial actions to prevent mobile drive unit 20 from colliding with obstacles and/or other objects.

Obstacle sensor 160 may also detect signals transmitted by other mobile drive units 20 operating in the vicinity of the illustrated mobile drive unit 20. For example, in particular embodiments of inventory system 10, one or more mobile drive units 20 may include an identification signal transmitter 162 that transmits a drive identification signal. The drive identification signal indicates to other mobile drive units 20 that the object transmitting the drive identification signal is in fact a mobile drive unit. Identification signal transmitter 162 may be capable of transmitting infrared, ultraviolet, audio, visible light, radio, and/or other suitable signals that indicate to recipients that the transmitting device is a mobile drive unit 20.

Additionally, in particular embodiments, obstacle sensor 160 may also be capable of detecting state information transmitted by other mobile drive units 20. For example, in particular embodiments, identification signal transmitter 162 may be capable of including state information relating to mobile drive unit 20 in the transmitted identification signal. This state information may include, but is not limited to, the position, velocity, direction, and the braking capabilities of the transmitting mobile drive unit 20. In particular embodiments, mobile drive unit 20 may use the state information transmitted by other mobile drive units to avoid collisions when operating in close proximity with those other mobile drive units. FIGS. 12A-12E illustrate an example of how this process may be implemented in particular embodiments of inventory system 10.

Control module 170 monitors and/or controls operation of drive module 120 and docking actuator 130. Control module 170 may also receive information from sensors such as position sensor 140 and holder sensor 150 and adjust the operation of drive module 120, docking actuator 130, and/or other components of mobile drive unit 20 based on this information. Additionally, in particular embodiments, mobile drive unit 20 may be configured to communicate with a management device of inventory system 10 and control module 170 may receive commands transmitted to mobile drive unit 20 and communicate information back to the management device utilizing appropriate communication components of mobile drive unit 20. Control module 170 may include any appropriate hardware and/or software suitable to provide the described functionality. In particular embodiments, control module 170 includes a general-purpose microprocessor programmed to provide the described functionality. Additionally, control module 170 may include all or portions of docking actuator 120, drive module 130, position sensor 140, and/or holder sensor 150, and/or share components with any of these elements of mobile drive unit 20.

Moreover, in particular embodiments, control module 170 may include hardware and software located in components that are physically distinct from the device that houses drive module 120, docking actuator 130, and/or the other components of mobile drive unit 20 described above. For example, in particular embodiments, each mobile drive unit 20 operating in inventory system 10 may be associated with a software process (referred to here as a "drive agent") operating on a server that is in communication with the device that houses drive module 120, docking actuator 130, and other appropriate components of mobile drive unit 20. This drive agent may be responsible for requesting and receiving tasks, requesting and receiving routes, transmitting state information associated with mobile drive unit 20, and/or otherwise interacting with management module 15 and other components of inventory system 10 on behalf of the device that physically houses drive module 120, docking actuator 130, and the other appropriate components of mobile drive unit 20. As a result, for the purposes of this description and the claims that follow, the term "mobile drive unit" includes software and/or hardware, such as agent processes, that provides the described functionality on behalf of mobile drive unit 20 but that may be located in physically distinct devices from the drive module 120, docking actuator 130, and/or the other components of mobile drive unit 20 described above.

While FIGS. 3A and 3B illustrate a particular embodiment of mobile drive unit 20 containing certain components and configured to operate in a particular manner, mobile drive unit 20 may represent any appropriate component and/or collection of components configured to transport and/or facilitate the transport of inventory holders 30. As another example, mobile drive unit 20 may represent part of an overhead crane system in which one or more crane assemblies are capable of moving within a network of wires or rails to a position suitable to dock with a particular inventory holder 30. After docking with inventory holder 30, the crane assembly may then lift inventory holder 30 and move inventory to another location for purposes of completing an assigned task.

Furthermore, in particular embodiments, mobile drive unit 20 may represent all or a portion of inventory holder 30. Inventory holder 30 may include motorized wheels or any other components suitable to allow inventory holder 30 to propel itself. As one specific example, a portion of inventory holder 30 may be responsive to magnetic fields. Inventory system 10 may be able to generate one or more controlled magnetic fields capable of propelling, maneuvering and//or otherwise controlling the position of inventory holder 30 as a result of the responsive portion of inventory holder 30. In such embodiments, mobile drive unit 20 may represent the responsive portion of inventory holder 30 and/or the components of inventory system 10 responsible for generating and controlling these magnetic fields. While this description provides several specific examples, mobile drive unit 20 may, in general, represent any appropriate component and/or collection of components configured to transport and/or facilitate the transport of inventory holders 30.

FIG. 4 illustrates in greater detail the components of a particular embodiment of inventory holder 30. In particular, FIG. 4 illustrates the structure and contents of one side of an example inventory holder 30. In a particular embodiment, inventory holder 30 may comprise any number of faces with similar or different structure. As illustrated, inventory holder 30 includes a frame 310, a plurality of legs 328, and docking surface 350.

Frame 310 holds inventory items 40. Frame 310 provides storage space for storing inventory items 40 external or internal to frame 310. The storage space provided by frame 310 may be divided into a plurality of inventory bins 320, each capable of holding inventory items 40. Inventory bins 320 may include any appropriate storage elements, such as bins, compartments, or hooks.

In a particular embodiment, frame 310 is composed of a plurality of trays 322 stacked upon one another and attached to or stacked on a base 318. In such an embodiment, inventory bins 320 may be formed by a plurality of adjustable dividers 324 that may be moved to resize one or more inventory bins 320. In alternative embodiments, frame 310 may represent a single inventory bin 320 that includes a single tray 322 and no adjustable dividers 324. Additionally, in particular embodiments, frame 310 may represent a load-bearing surface mounted on mobility element 330. Inventory items 40 may be stored on such an inventory holder 30 by being placed on frame 310. In general, frame 310 may include storage internal and/or external storage space divided into any appropriate number of inventory bins 320 in any appropriate manner.

Additionally, in a particular embodiment, frame 310 may include a plurality of device openings 326 that allow mobile drive unit 20 to position docking head 110 adjacent docking surface 350. The size, shape, and placement of device openings 326 may be determined based on the size, the shape, and other characteristics of the particular embodiment of mobile drive unit 20 and/or inventory holder 30 utilized by inventory system 10. For example, in the illustrated embodiment, frame 310 includes four legs 328 that form device openings 326 and allow mobile drive unit 20 to position mobile drive unit 20 under frame 310 and adjacent to docking surface 350. The length of legs 328 may be determined based on a height of mobile drive unit 20.

Docking surface 350 comprises a portion of inventory holder 30 that couples to, abuts, and/or rests upon a portion of docking head 110, when mobile drive unit 20 is docked to inventory holder 30. Additionally, docking surface 350 supports a portion or all of the weight of inventory holder 30 while inventory holder 30 is docked with mobile drive unit 20. The composition, shape, and/or texture of docking surface 350 may be designed to facilitate maneuvering of inventory holder 30 by mobile drive unit 20. For example, as noted above, in particular embodiments, docking surface 350 may comprise a high-friction portion. When mobile drive unit 20 and inventory holder 30 are docked, frictional forces induced between docking head 110 and this high-friction portion may allow mobile drive unit 20 to maneuver inventory holder 30. Additionally, in particular embodiments, docking surface 350 may include appropriate components suitable to receive a portion of docking head 110, couple inventory holder 30 to mobile drive unit 20, and/or facilitate control of inventory holder 30 by mobile drive unit 20.

Holder identifier 360 marks a predetermined portion of inventory holder 30 and mobile drive unit 20 may use holder identifier 360 to align with inventory holder 30 during docking and/or to determine the location of inventory holder 30. More specifically, in particular embodiments, mobile drive unit 20 may be equipped with components, such as holder sensor 150, that can detect holder identifier 360 and determine its location relative to mobile drive unit 20. As a result, mobile drive unit 20 may be able to determine the location of inventory holder 30 as a whole. For example, in particular embodiments, holder identifier 360 may represent a reflective marker that is positioned at a predetermined location on inventory holder 30 and that holder sensor 150 can optically detect using an appropriately-configured camera.

Figure 5:
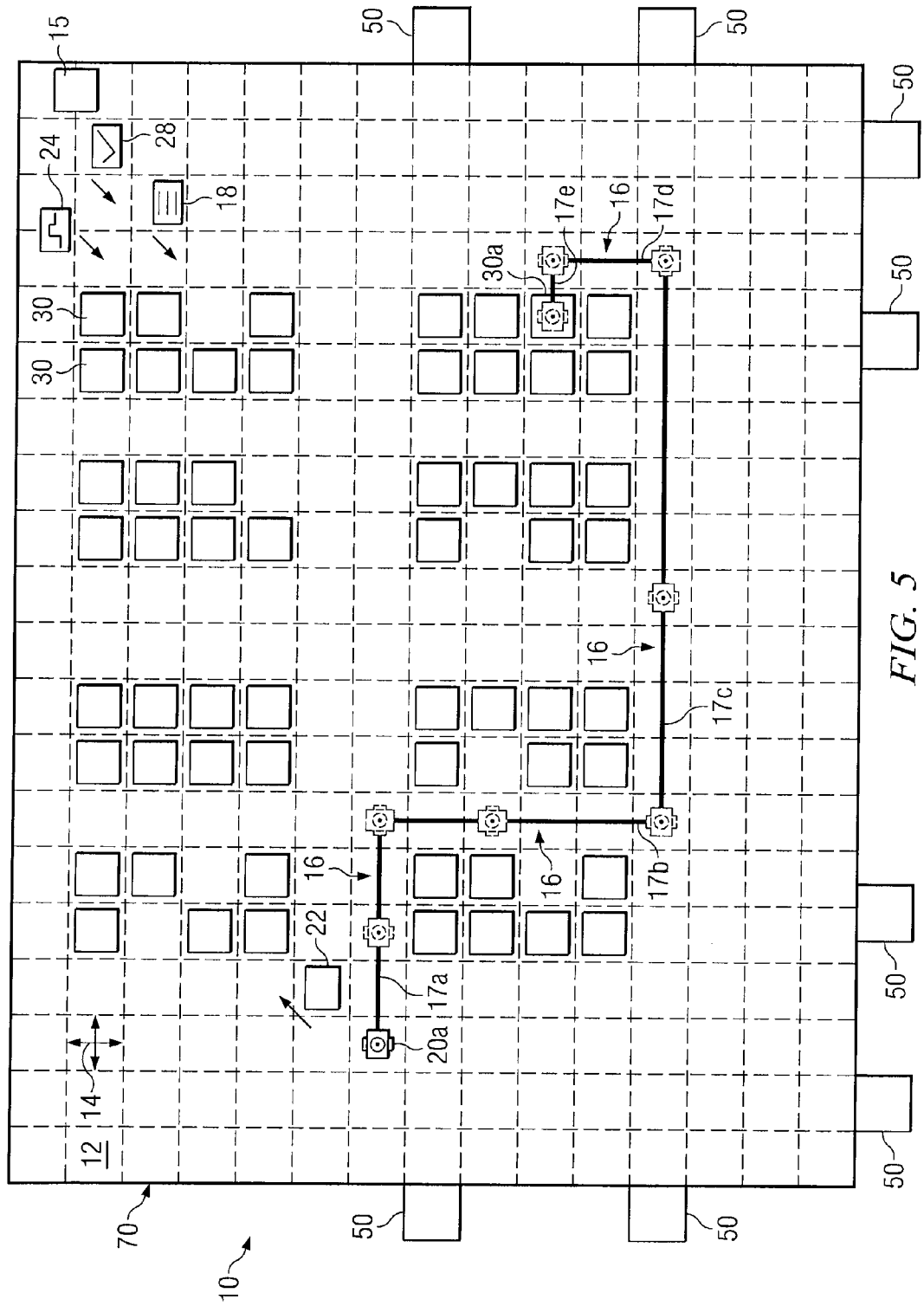
FIG. 5 illustrates an example of routing and reservation techniques that may be utilized by the management module in particular embodiments of the inventory system illustrated in FIG. 1.
Figure 6:
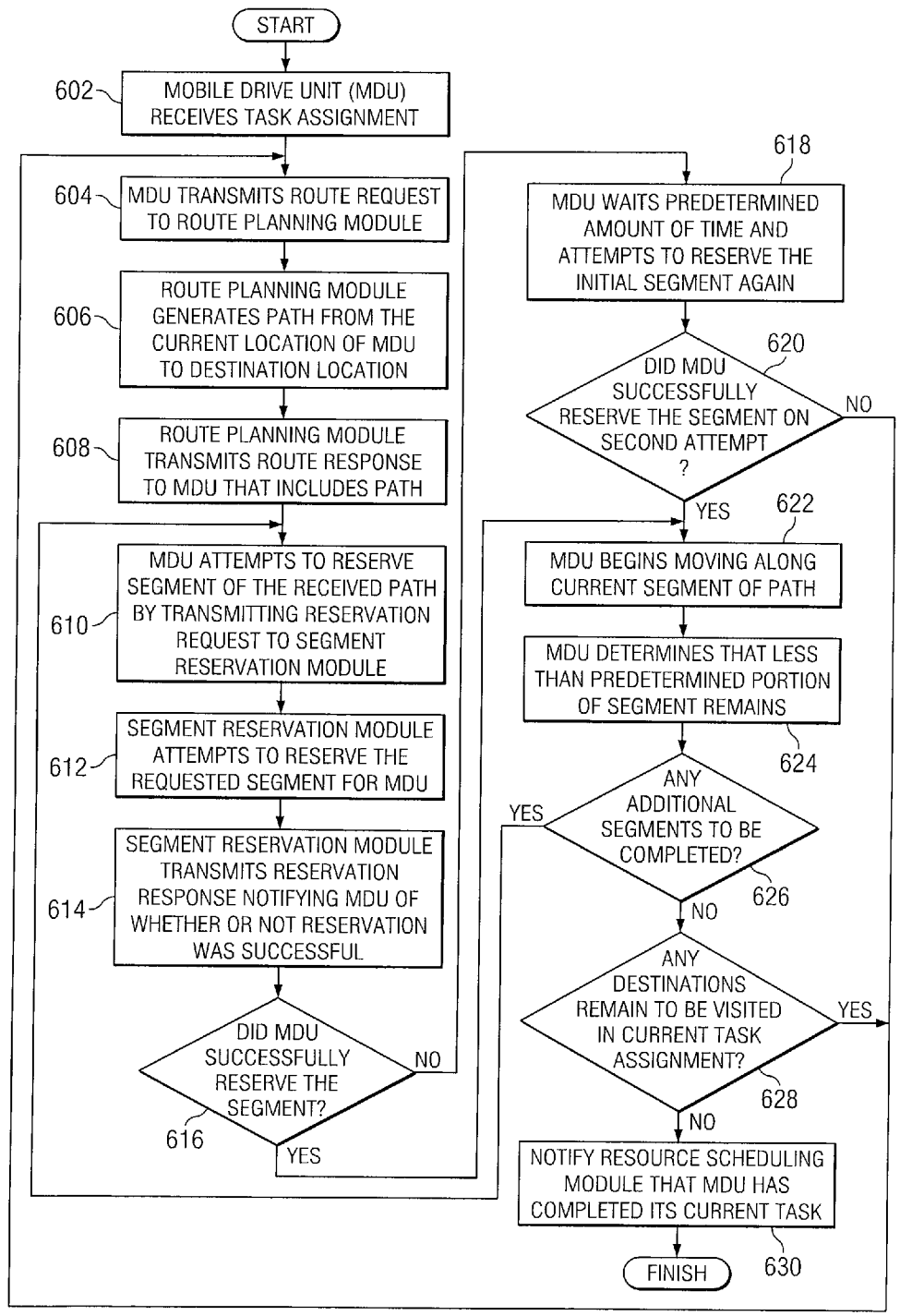
FIG. 6 is a flowchart detailing example operation of a particular embodiment of the management module in managing movement of mobile drive units in the inventory system.

FIGS. 5 and 6 illustrate a technique for planning and directing the movement of mobile drive units 20 within workspace 70 while the mobile drive units 20 complete assigned tasks. More specifically, FIG. 5 illustrates an example of how a mobile drive unit 20 may request, from management module 15, a path to a destination associated with an assigned task and then interact with management module 15 to allow mobile drive unit 20 to successfully traverse the path. FIG. 6 is a flowchart detailing example operation of a particular embodiment of mobile drive unit 20 in moving to a designated destination according to the techniques illustrated by FIG. 5.

FIG. 5 illustrates an example showing routing and reservation techniques that may be utilized in particular embodiments of inventory system 10. In general, FIG. 5 illustrates an example in which mobile drive unit 20 receives an assigned task 18 from management module 15 that instructs mobile drive unit 20 to retrieve inventory holder 30a from a storage cell where inventory holder 30a is currently located. Mobile drive unit 20 then requests a path to the location of inventory holder 30a and follows the received path to the relevant location.

In the illustrated embodiment of inventory system 10, workspace 70 is associated with a grid 12 comprising a plurality of cells 14, and mobile drive units 20 are configured to move within workspace 70 by navigating from the center of one cell 14 to the center of another. Nonetheless, in alternative embodiments, mobile drive units 20 may be configured to navigate grid 12 in any appropriate manner and starting points, destinations, and any intermediate points on the path traversed by mobile drive unit 20 may or may not represent the center point of a cell 14 or any other portion of grid 12. Furthermore, although FIG. 5 illustrates a grid-based embodiment of inventory system 10, alternative embodiments of inventory system 10 may utilize a gridless workspace having an arbitrary shape and structure.

As shown in FIG. 5, the routing process begins with management module 15 transmitting a task assignment 18 to mobile drive unit 20. Task assignment 18 identifies one or more destinations associated with a corresponding task. Task assignment 18 may identify the relevant destinations directly or by reference to the known location of specific components (e.g., a particular inventory holder 30 or inventory station 50) or a particular portion of workspace 70. Task assignment 18 may also include any additional information suitable for mobile drive unit 20 to use in completing the assigned task.

Upon receiving task assignment 18, mobile drive unit 20 requests a path to the location identified by the task assignment 18 or, if task assignment 18 identifies multiple locations, to the first location identified by task assignment 18. In the illustrated embodiment, mobile drive unit 20 requests a path by transmitting a route request 22 to route planning module 94. In particular embodiments, route request 22 may include one or more destination locations and the current location of mobile drive unit 20 or the anticipated location of mobile drive unit 20 when it completes its current segment 17. In alternative embodiments, management module 15 may independently monitor the location or assigned task of each mobile drive unit 20 and, consequently, one or more of these locations may be omitted from route request 22.

When route planning module 94 receives route request 22, route planning module 94 generates a path 16 for the requesting mobile drive unit 20 to use in moving from its current location to the requested destination. As noted above, route planning module 94 may use any suitable techniques to generate, select, or determine an appropriate path 16 for the requesting mobile drive unit 20. Route planning module 94 may then communicate information identifying path 16 to the requesting mobile drive unit 20 as part of a route response 24. For example, route planning module 94 may communicate information specifying certain points along path 16, specifying directions and distances to move, specifying known path segments to use in moving to the requested destination, specifying other equipment (for example, a lift, conveyor, or truck) or features of the workspace (such as a ramp or tunnel) to be utilized, and/or indicating, in any other appropriate manner, the portion of workspace 70 mobile drive unit 20 should traverse in moving between its current location and the requested destination. In particular embodiments, route planning module 94 communicates path 16 to mobile drive unit 20 as part of route response 24.

After route planning module 94 transmits information identifying one or more paths 16, this information is received by mobile drive unit 20. In particular embodiments, mobile drive unit 20 may then store this information for subsequent use in navigating to the destination location. Mobile drive unit 20 then attempts to reserve a segment 17 or other suitable portion of path 16. Mobile drive unit 20 may reserve a segment 17 of path 16 by taking any appropriate steps, based on the configuration of inventory system 10, to ensure that no other mobile drive unit 20, or other type of device capable of moving within workspace 70, is or will be traversing the reserved segment 17, positioned on the reserved segment 17, and/or otherwise impeding movement along the reserved segment 17 while the relevant mobile drive unit 20 has that segment 17 reserved.

In particular embodiments, route planning module 94 may, in response to a particular route request 22, generate multiple paths to a particular destination. Moreover, management module 15 may then transmit all of the generated paths 16 to the requesting mobile drive unit 20. Additionally, route planning module 94 or mobile drive unit 20 may assign a priority to each of the generated paths 16. As a result, in such embodiments, the requesting mobile drive unit 20 may be capable of storing the multiple paths 16 generated by route planning module 94 and then attempting to reserve segments 17 of the highest priority path 16. If the attempted reservation is denied, the requesting mobile drive unit 20 may then attempt to request a segment 17 from the next highest priority path 16. The requesting mobile drive unit 20 may then proceed to request segments 17 from each of the received paths 16 in order of priority until the requesting mobile drive unit 20 successfully reserves segments 17 from one of the received paths 16.

Furthermore, in particular embodiments or under certain conditions, multiple mobile drive units 20 may be allowed to utilize a particular segment 17 simultaneously. In such embodiments, mobile drive unit 20 may reserve a segment 17 by taking any appropriate steps to ensure that only mobile drive units 20 that satisfy particular conditions may use the reserved segment at the same time. As one example, in particular embodiments, segment reservation module 96 may reserve a particular segment by taking appropriate steps to ensure that only mobile drive units 20 moving in the same direction as that mobile drive unit 20 may reserve the relevant segment 17. As another example, in particular embodiments, inventory system 10 may be configured to allow a predetermined maximum number or concentration of mobile drive units 20 to use a given segment 17 and mobile drive unit 20 may reserve a given segment 17 by requesting a reservation for that segment 17. Management module 15 may then conditionally grant the reservation based on whether the current number or density of mobile drive units 20 utilizing the requested segment 17 is less than the predetermined maximum.

In the illustrated embodiment, mobile drive unit 20 reserves segment 17 by transmitting a reservation request 26 to segment reservation module 96. Reservation request 26 identifies the segment 17 that mobile drive unit 20 is attempting to reserve. Reservation request 26 may identify the relevant segment 17 in any manner appropriate based on the configuration and capabilities of mobile drive unit 20 and segment reservation module 96. For example, in particular embodiments, reservation request 26 identifies the relevant segment 17 by identifying the starting and ending coordinates of that segment 17, by specifying a direction and distance from the current location of mobile drive unit 20, or by including any other suitable information from which the requested segment 17 can be identified, either independently or based on other information maintained by segment reservation module 96 during operation.

Segment reservation module 96 receives the reservation request 26 and extracts information identifying the requested segment 17 from reservation request 26. Segment reservation module 96 then determines whether or not the requesting mobile drive unit 20 can reserve the requested segment 17. In particular embodiments, segment reservation module 96 determines based solely on whether another mobile drive unit 20 currently has the requested segment 17 reserved. In alternative embodiments, however, segment reservation module 96 may determine based both on whether another mobile drive unit 20 currently has the requested segment 17 reserved and on a priority level associated with the requesting mobile drive unit 20 or a task the mobile drive unit 20 is currently completing whether the requesting mobile drive unit 20 can reserve the requested segment 17. Consequently, segment reservation module 96 may refuse use of certain segments 17 (or segments 17 exceeding a certain size) to mobile drive units 20 having an insufficient priority level. In general, however, segment reservation module 96 may use any appropriate considerations to determine whether the received reservation request 26 can be satisfied.

Additionally, in particular embodiments, segment reservation module 96 may be configured to compensate for potential uncertainties in the location of mobile drive unit 20. In particular, segment reservation module 96 may attempt to reserve a modified segment that includes, but is larger than, the requested segment 17. As a result, if the actual location of the requesting mobile drive unit 20 differs, by less than some predetermined amount, from that calculated by mobile drive unit 20 and/or management module 15, collisions may still be prevented as a result of the larger reservation secured by segment reservation module 96. Segment reservation module 96 may be configured to always modify reservation requests 26 in this manner, to modify reservation requests 26 when management module 15 determines the actual location of the requesting mobile drive unit 20 differs from the calculated location, or to modify reservation requests 26 at any other appropriate times.

Furthermore, in particular embodiments of inventory system 10, mobile drive units 20 may attempt to make and/or resource scheduling module 92 may grant reservations of different types depending on the manner in which requesting mobile drive units 20 intend to use the requested segment 17. Moreover, resource scheduling module 92 may follow different policies for granting or denying each of these different types of reservations. For example, in particular embodiments, mobile drive units 20 may be configured to request a segment 17 that includes one or more cells 14 adjacent to the cells 14 through which path 16 runs. Consequently, when a requesting mobile drive unit 20 plans to rotate inventory holder 30 as part of its movement in completing a particular segment 16, the requesting mobile drive unit 20 may attempt to place rotation reservations on the cells 14 adjacent to the cell 14 in which mobile drive unit 20 intends to perform the rotation. Depending on the size of inventory holders 30 relative to the cells 14 utilized in the relevant workspace 70, the requesting mobile drive unit 20 may not need to use the entirety of each neighboring cell 14 to rotate. As a result, segment reservation module 96 may allow other mobile drive units 20 to also place reservation requests on a particular neighboring cell 14 at the same time the first requesting mobile drive unit 20 has reserved that particular cell 14. More specifically, in particular embodiments, resource scheduling module 92 may allow other mobile drive units 20 to reserve the neighboring cell 14 for purposes of encroaching into that cell 14 while rotating inventory holders 30 in other cells 14 that border the neighboring cell 14. This may reduce the number of delays mobile drive units 20 face when attempting to reserve a sufficiently large portion of workspace 70 to rotate inventory holders 30.

If segment reservation module 96 determines that the requesting mobile drive unit 20 cannot reserve the requested segment 17, segment reservation module 96 may notify the requesting mobile drive unit 20 that it did not successfully reserve the requested segment 17. For example, in the illustrated embodiment, segment reservation module 96 transmits a reservation response 28 that indicates the reservation was unsuccessful. Alternatively, in particular embodiments, segment reservation module 96 does not notify the requesting mobile drive unit 20 of the failed reservation, and the requesting mobile drive unit 20 is configured to determine the reservation was unsuccessful if the requesting mobile drive unit 20 does not receive an affirmative response within a predetermined period of time.

Additionally, in particular embodiments, segment reservation module 96 may be configured to take some remedial action if segment reservation module 96 is unable to satisfy a particular reservation request 26. For example, in particular embodiments, segment reservation module 96 may queue unsatisfied reservation requests 26 and attempt to satisfy them once any currently pending reservation for the requested segment 17 is terminated. Alternatively, however, segment reservation module 96 may be configured to discard unsatisfied reservation requests 26 after a single attempt to satisfy them, after a predetermined number of failed attempts, or after unsuccessfully attempting to satisfy such requests for a predetermined amount of time. The requesting mobile drive unit 20 may then be expected to transmit another reservation request 26 later if it is still attempting to reserve the requested segment 17. In addition, segment reservation module 96 may be configured to attempt reserving a portion of the requested segment 17 or a modified version of the requested segment 17 if the segment reservation module 96 is unable to successfully reserve the originally requested segment 17 for the requesting mobile drive unit 20. More generally, however, depending on the configuration of inventory system 10, segment reservation module 96 may be configured to take any appropriate remedial action or, alternatively, to take no remedial action at all, if segment reservation module 96 is unable to satisfy a particular reservation request 26.

Similarly, depending on the configuration of mobile drive unit 20, mobile drive unit 20 may execute any appropriate remedial action in response to determining that segment reservation module 96 has not satisfied the reservation. In particular embodiments, mobile drive unit 20 may wait a predetermined amount of time and attempt to reserve the same segment 17 again. In alternative embodiments, mobile drive unit 20 may be configured to request a new path 16 from route planning module 94, if mobile drive unit 20 is unsuccessful in reserving the requested segment 17 or if mobile drive unit 20 is unsuccessful after a predetermined number of attempts. Additionally, in particular embodiments, mobile drive units 20 may be able to adjust the size of the segments 17 mobile drive units 20 request. As a result, the requesting mobile drive unit 20 may, in response to determining that the attempted reservation was unsuccessful, attempt to reserve a smaller portion of the same requested segment 17. In such embodiments, the requesting mobile drive unit 20 may then request or automatically receive incremental portions of the original requested segment 17 as the requesting mobile drive unit 20 moves and/or the remaining portions become free. More generally, however, mobile drive unit 20 may respond in any suitable manner to the failed reservation attempt.

If, instead, segment reservation module 96 determines that the received reservation request 26 can be satisfied, segment reservation module 96 reserves the requested segment 17 for the requesting mobile drive unit 20. As part of reserving the requested segment, segment reservation module 96 stores information indicating the reserved state of the relevant segment 17 and takes any additional steps appropriate to ensure that the requesting mobile drive unit 20 may use the requested segment 17 until the reservation is terminated. Segment reservation module 96 also notifies the requesting mobile drive unit 20 that it has successfully reserved the requested segment 17. For example, in the illustrated embodiment, segment reservation module 96 transmits an acknowledgement, such as reservation response 28, that indicates to the requesting mobile drive unit 20 that the reservation was successful. When the requesting mobile drive unit 20 receives the reservation response 28 indicating that the attempted reservation was successful, the requesting mobile drive unit 20 begins moving along the reserved segment 17.

Returning to the example illustrated in FIG. 5, when mobile drive unit 20a receives reservation response 28 indicating that mobile drive unit 20a has successfully reserved segment 17a, mobile drive unit 20 begins moving along segment 17a. This is illustrated is in FIG. 5 by the dotted-line silhouette of mobile drive unit 20. At some point after beginning movement along segment 17a, mobile drive unit 20a attempts to reserve the next segment of the path that mobile drive unit 20a received from route planning module 94, i.e., segment 17b. In particular embodiments, mobile drive unit 20a may wait until mobile drive unit 20a reaches the end of the reserved segment (i.e., when mobile drive unit 20a reaches the second silhouette) and then request the next segment 17.

Alternatively, mobile drive unit 20a may attempt to reserve segment 17b before completing segment 17a. In particular embodiments, mobile drive unit 20a may request segment 17b at an appropriate point while moving across segment 17a. As one example, mobile drive unit 20a may request segment 17b after completing a predetermined proportion of segment 17a (e.g., after completing 75% of segment 17a). As another example, mobile drive unit 20 may request segment 17b when only a predetermined amount of segment 17a is left to be completed (e.g., once mobile drive unit 20a has completed all but half a cell's width of segment 17a). More generally, however, particular embodiments of mobile drive unit 20, or any appropriate component of inventory system 10 responsible for reserving segments 17 on behalf of mobile drive unit 20, may be configured to reserve the next segment in the current path at any suitable time while mobile drive unit 20 is moving along its currently-reserved segment 17. The remainder of this description assumes that mobile drive unit 20 is configured to attempt reservation of a new segment 17 before completing its current segment 17.

Additionally, as discussed above with respect to FIGS. 3A and 3B, particular embodiments of mobile drive unit 20a may include one or more sensors capable of detecting certain types of obstacles, obstructions, or other impediments to the movement of mobile drive unit 20. In response to detecting an obstacle, mobile drive unit 20 may be configured to stop and/or take any appropriate measures to complete the assigned task. As one example, mobile drive unit 20 may stop moving and periodically poll the relevant sensor to determine whether the obstacle has been removed. As another example, mobile drive unit 20a may request a new path upon detecting an obstacle located on or near a segment 17 of its current path 16. As yet another example, mobile drive unit 20 may notify management module 15 or a human operator of inventory system 10 to initiate appropriate actions to have the obstacle removed. In particular embodiments, mobile drive unit 20a may be configured to override its obstacle detection capabilities to support certain types of special navigation techniques. An example of these techniques is discussed in greater detail below with respect to FIGS. 12A-12E, 13, and 14.

In particular embodiments, as mobile drive unit 20a exits a particular cell 14 of segment 17a, mobile drive unit 20a may release its reservation with respect to that cell 14. Alternatively, in particular embodiments, mobile drive unit 20a may wait until reaching the end of segment 17a (i.e., when mobile drive unit 20a arrives at the second silhouette), and then terminate its reservation of all cells 14 in segment 17a. Mobile drive unit 20a may release its reservation of all or a portion of segment 17a by transmitting a reservation termination message (not shown) to segment reservation module 96 or by taking any other appropriate steps to relinquish its use of segment 17a. Alternatively, in particular embodiments, mobile drive unit 20a may not be configured to take any affirmative steps to terminate the reservation. Instead, segment reservation module 96 may itself detect that mobile drive unit 20a has completed segment 17a and terminate the reservation in response or segment reservation module 96 may time-out the reservation if mobile drive unit 20a does not renew the reservation within a predetermined time period. More generally, segment reservation module 96 may monitor any particular aspect of the operation of mobile drive unit 20a including, for example, its location, speed, last renewal request, and/or any other appropriate aspect of the state of mobile drive unit 20a, and terminate the reservation at any appropriate time based on the state of mobile drive unit 20a.

If mobile drive unit 20a has successfully reserved segment 17b by the time mobile drive unit 20a reaches the end of segment 17a, mobile drive unit 20a may begin moving along segment 17b. If mobile drive unit 20a has not successfully reserved segment 17b by the time mobile drive unit 20a reaches the end of segment 17a, mobile drive unit 20a may stop at the intersection of segment 17a and segment 17b and take appropriate steps based on the configuration of mobile drive unit 20a. For example, as noted above, mobile drive unit 20a may repeatedly attempt to reserve segment 17b until successful, make a predetermined number of reservation attempts and then request a new path 16, or take any other steps to continue its movement towards the destination location.

Once mobile drive unit 20a successfully reserves segment 17b, mobile drive unit 20a traverses segment 17b in a similar fashion. At an appropriate point during the completion of segment 17b, mobile drive unit 20a attempts to reserve segment 17c and repeats the above process. Mobile drive unit 20a continues reserving and traversing segments (as suggested by the dotted-line silhouettes) until mobile drive unit 20a reaches the destination location. Mobile drive unit 20a may then take any actions appropriate to complete the assigned task. For example, in FIG. 5, completion of the assigned task may include mobile drive unit 20a docking with a particular inventory holder 30 located at the destination location. If the currently-assigned task includes multiple destinations, mobile drive unit 20a may request a path 16 to the next step by transmitting a new route request 22 to route planning module 94 and repeating the above process with respect to the next destination. If the task assignment 18 that mobile drive unit 20a received does not specify any additional locations, mobile drive unit 20a may request or be given another assigned task from resource scheduling module 92 or otherwise notify management module 15 that mobile drive unit 20a is available for new assignments.

Although the illustrated example, utilizes only straight segments 17, particular embodiments of inventory system 10 may be configured to generate paths that include segments covering turns, curves, and other non-linear portions. Additionally, although in the illustrated example segments 17 extend without limit between turns in path 16, particular embodiments of inventory system 10 may be configured to generate paths 16 that have an upper limit on segment length or to allow only up to a maximum segment length to be reserved with a single reservation. As a result, a relatively long straight segment, such as segment 17c, may in reality represent a series of smaller, connected segments 17 running in the same direction.

Additionally, although mobile drive unit 20a relies on a single path in the illustrated example, mobile drive units 20 may, in particular embodiments, be configured to request new paths 16 to a particular location while in the process of completing a previously-requested path 16 to the same location. As noted above, mobile drive units 20 may be configured to request a new path 16 if they are unsuccessful in reserving a particular segment 17 in the current path 16. More generally, however, mobile drive units 20 may be configured to request a new path 16 to a particular destination at any appropriate time while completing an existing path 16 to the same destination. For example, a particular embodiment of mobile drive unit 20 may request a new path 16 a predetermined amount of time after requesting the original path, after completing each segment 17, or at any other suitable time. In such embodiments, mobile drive unit 20 may transmit the originally received path 16 back to route planning module 94 to be used as a starting point for determining any improved paths 16 to the same destination.

Moreover, management module 15 may be capable of pushing new paths 16 to a mobile drive unit 20 while that mobile drive unit 20 is in the process of completing a previously-received path 16. As one example, in particular embodiments, management module 15 may be configured to manage congestion by transmitting new paths 16 to mobile drive units 20 that are located in or near congested areas or that are traveling on paths that will traverse or pass near congested areas. As another example, management module 15 may be configured to improve the operational efficiency of inventory system 10 by transmitting new paths 16 to mobile drive units 20 that are optimized based on the attributes of inventory holders 30 or inventory stations 50 associated with the relevant mobile drive units 20 or the tasks they are completing. In general, either mobile drive unit 20 or route planning module 94 may determine that mobile drive unit 20 should receive a new path 16 based on changes in any appropriate condition, circumstance, property, or state of inventory system 10 or any individual components of inventory system 10.

In addition, although the illustrated example, describes an example embodiment in which route planning module 94 transmits the entirety of path 16 to mobile drive unit 20a at one time, particular embodiments of route planning module 94 may be configured to transmit path 16 in portions. For example, in a particular embodiment, route planning module 94 may be configured to transmit path 16 to the requesting mobile drive unit 20 one segment 17 at a time. After traversing a particular segment 17, the requesting mobile drive unit 20 may then request another segment 17 of the path 16. At that point, route planning module 94 may determine, based on changes in conditions within workspace 70 and/or any other appropriate considerations, whether to provide the next segment 17 in the original path 16 or to generate a new path 16 to the destination of the requesting mobile drive unit 20. Route planning module 94 then communicates another segment 17, either from the original path 16 or a new path 16, to the requesting mobile drive unit 20. This process may continue until the requesting mobile drive unit 20 reaches its destination.

Furthermore, while the illustrated example focuses on an embodiment of inventory system 10 in which mobile drive units 20 actively request reservation of particular segments 17 on their own behalf, in alternative embodiments management module 15 or other suitable components of inventory system 10 may be responsible for initiating reservations, either explicitly or implicitly. As one example, in particular embodiments, management module 15 may monitor the location and current path of mobile drive units 20 and may reserve appropriate segments 17 on behalf of mobile drive units 20 at appropriate times during the movement of mobile drive units 20. As another example, particular embodiments of inventory system 10 may include signaling devices, such as traffic signals, that mange the flow of traffic within workspace 70. As a result, management module 15 or other components that control the signaling devices may implicitly reserve a particular segment 17 for a mobile drive unit 20 by signaling to other mobile drive units 20 that they are not permitted to use the relevant segment 17 at a particular time.

Consequently, inventory system 10 supports a number of techniques that provide for efficient routing, navigation, and management of mobile drive units 20 moving within workspace 70. Because inventory system 10 supports techniques for resolving conflicting requests for a particular segment 17 by two different mobile drive units 20 management module 15 may also help reduce or eliminate collisions between mobile drive units 20 simultaneously completing tasks. As a result, the described techniques may provide one or more operational benefits.

FIG. 6 is a flow chart illustrating the operation of a particular embodiment of mobile drive unit 20 in traversing a path 16 to a designated location. More specifically, FIG. 6 illustrates the process by which mobile drive unit 20, in particular embodiments of inventory system 10, requests a path to a particular destination and iteratively reserves and traverses the various segments 17 of that path 16. Any of the steps illustrated in FIG. 6 may be combined, modified, or deleted where appropriate, and additional steps may also be added to those shown in the flowchart. Moreover, the described steps may be performed in any suitable order without departing from the scope of the invention.

The example operation begins, at step 602, with mobile drive unit 20 receiving a task assignment 18 from resource scheduling module 92. Task assignment 18 identifies one or more locations associated with a task assigned to mobile drive unit 20. In response to receiving task assignment 18, mobile drive unit 20 requests, from route planning module 94, a path to one of the destinations identified in task assignment 18. In particular embodiments, mobile drive unit 20 requests the path by transmitting a route request 22 to route planning module 94 at step 604. Route request 22 identifies a destination location and the current location of mobile drive unit 20.

At step 606, route planning module 94 generates, selects, or identifies a path 16 from the current location of mobile drive unit 20 to the destination location. Route planning module 94 then transmits path 16 to mobile drive unit 20. In particular embodiments, route planning module 94 transmits path 16 to mobile drive unit 20 by transmitting a route response 24 to mobile drive unit 20, at step 608, that identifies path 16 in an appropriate manner based on the capabilities of mobile drive unit 20. In particular embodiments, path 16 includes multiple segments 17, including at least an initial segment 17 and one or more additional segments 17. The initial segment 17 is associated with a section of workspace 70 adjacent to the current location of mobile drive unit 20 when mobile drive unit 20 requests the path, and at least one of the additional segments 17 is associated with a section of workspace 70 adjacent to the destination. Path 16 may include any number of additional segments 17.

After receiving the path from route planning module 94, mobile drive unit 20 attempts to reserve the initial segment 17 of the received path 16. In particular embodiments, mobile drive unit 20 attempts to reserve the initial segment 17 by transmitting a reservation request 26 to segment reservation module 96 at step 610. Reservation request 26 identifies the requested segment 17.

Upon receiving reservation request 26, segment reservation module 96 attempts to reserve the requested segment 17 for mobile drive unit 20 at 612. In particular embodiments, segment reservation module 96 may modify the requested segment 17 to account for potential uncertainties or errors in the calculated position of mobile drive unit 20. As a result, in particular embodiments, segment reservation module 96 may reserve a portion of workspace 70 other than the segment specified by the received reservation request 26. For example, segment reservation module 96 may, under appropriate circumstances, expand, translate, and/or otherwise modify the requested segment to create a modified segment more suitable for use by the requesting mobile drive unit 20. In particular embodiments, segment reservation module 96 may be configured to modify the requested segment based on an error margin utilized by inventory system 10. Segment reservation module 96 may, as a result, attempt to reserve a portion of workspace 70 that is expanded, shifted, or otherwise modified from the reserved segment 17 in an amount determined based on the error margin. As a specific example, in particular embodiments that utilize a grid-based workspace 70 that includes a plurality of cells 14, segment reservation module 96 may attempt to reserve a segment 17 that includes one or more cells 14, beyond that included in the requested segment 17, that extend in the direction that the requesting mobile drive unit 20 is currently traveling. As another example, in particular embodiments, segment reservation module 96 may attempt to reserve a segment that has been shifted a particular number of cells in a specified direction.

Segment reservation module 96 may then notify mobile drive unit 20 of whether or not mobile drive unit 20 has successfully reserved a segment 17 for mobile drive unit 20. Alternatively, segment reservation module 96 may notify mobile drive unit 20 only of successful reservation attempts. In particular embodiments, segment reservation module 96 notifies mobile drive unit 20 by transmitting a reservation response 28 to mobile drive unit 20 at step 614.

At step 616, mobile drive unit 20 determines whether mobile drive unit 20 has successfully reserved the initial segment 17. If mobile drive unit 20 was not successful in reserving the initial segment 17, mobile drive unit 20 may take appropriate steps to continue working toward completion of the assigned task. For example, in the illustrated embodiment, mobile drive unit 20 waits a predetermined amount of time and attempts to reserve the initial segment again at step 618. Moreover, in the illustrated embodiment, mobile drive unit 20 determines at step 620 if the second attempt is successful. If the second attempt is successful, operation continues at step 622. If the second attempt is not successful, operation returns to 604 with mobile drive unit 20 requesting a new path 16.

Once mobile drive unit 20 is able to successfully reserve the initial segment 17, mobile drive unit 20 begins moving away from its original location along the initial segment of the path at step 622. At step 624, mobile drive unit 20 determines that there is less than a predetermined portion of the initial segment 17 left to complete. As a result, mobile drive unit 20 determines, at step 626, whether any additional segments 17 remain to be completed in the current path 16.

If segments 17 remain to be completed in the current path 16, mobile drive unit 20 attempts to reserve the next segment 17, returning to step 610. If mobile drive unit 20 successfully reserves the next segment operation continues with mobile drive unit 20 moving along the next segment 17. If mobile drive unit is not successful in reserving the next segment 17, operation continues through to step 622. If mobile drive unit 20 reaches the end of the initial segment 17 before successfully reserving the next segment, mobile drive unit 20 may pause its movement at the end of the initial segment and remain stationary until mobile drive unit 20 successfully reserves the next segment or obtains an alternative path.

If no segments 17 remain to be completed in the current path, mobile drive unit 20 determines whether any destinations remain to be visited in the current task assignment 18 at step 628. If so, operation returns to step 604. If not, mobile drive unit 20 may notify resource scheduling module 92 that mobile drive unit 20 has completed its current task at step 630. Operation with respect to completing the current task may then end as shown in FIG. 6.

Figure 7:
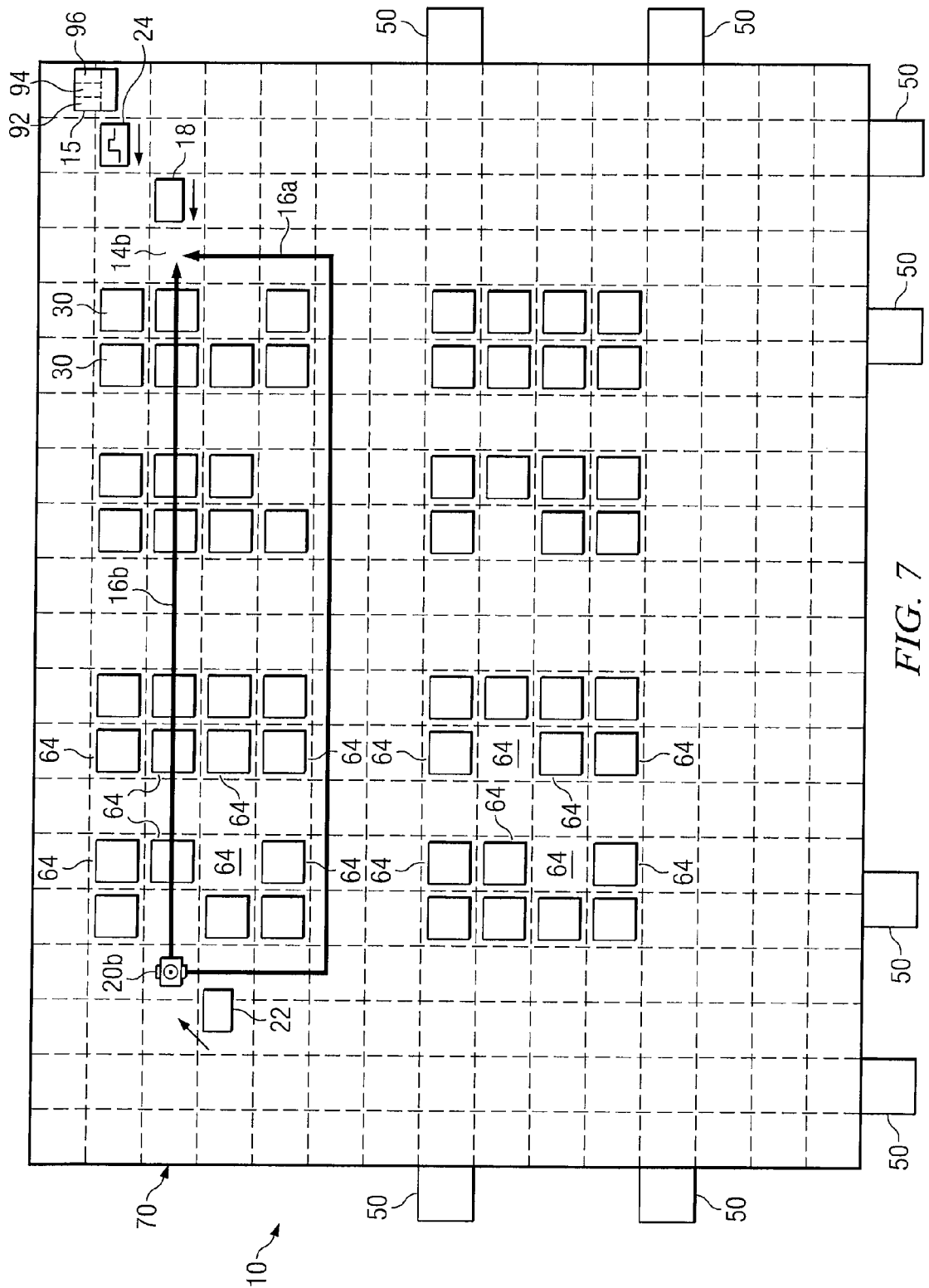
FIG. 7 illustrates an example embodiment of the inventory system that is capable of planning paths for a requesting mobile drive unit based on the mobile drive unit's current state.

FIGS. 7 and 8 illustrate a technique for planning paths based on the current state of a requesting mobile drive unit 20. More specifically, FIG. 7 illustrates an example of how such techniques might be implemented in a particular inventory system 10, and FIG. 8 is a flowchart detailing example operation of management module 15 in implementing a particular embodiment of these techniques. As one example of how such a technique might be used in inventory system 10, particular embodiments of inventory system 10 may allow mobile drive units 20 that are not docked to an inventory holder 30 to move through spaces currently occupied by stored inventory holders 30, but mobile drive units 20 that are docked with inventory holders 30 may not be capable of doing so. As a result, when undocked, mobile drive units 20 may be able to "tunnel" through cells 14 having inventory holders 30, thereby allowing for more effective use of system resources.

FIG. 7 illustrates techniques that may be used by management module 15 in generating appropriate paths 16 for mobile drive units 20. More specifically, in particular embodiments, when mobile drive unit 20 requests a path 16, route planning module 94, management module 15 in general, or other appropriate components of inventory system 10 determine a state of the requesting mobile drive unit 20. As used in this description and the claims that follow, "state" may refer to transitional, temporary conditions, such as a current task assignment, that are associated with the requesting mobile drive unit 20 as well as permanent characteristics and properties, such as height and width, associated with the requesting mobile drive unit 20.

Route planning module 94 then generates, selects, or identifies a path based in part on the state of the requesting mobile drive unit 20. More specifically, the state of mobile drive unit 20 may dictate the cells through which mobile drive unit 20 can travel, and route planning module 94 may produce a path 16 that utilizes appropriate cells 14. To illustrate, FIG. 7 shows an example of two alternative paths 16, paths 16a and 16b, that might be generated by route planning module 94 based on a particular aspect of the state of the requesting mobile drive unit 20b. Specifically, FIG. 7 illustrates two paths 16 that may be generated based on whether or not mobile drive unit 20b is currently docked with an inventory holder 30.

To begin the example, mobile drive unit 20b receives a task assignment 18 as discussed above with respect to FIG. 5. Task assignment 18 identifies a destination associated with a corresponding task assigned to mobile drive unit 20b. In response to task assignment 18, mobile drive unit 20b requests path 16 from route planning module 94. In the example, mobile drive unit 20b requests path 16 by transmitting route request 22, which identifies the relevant destination location, here cell 14b.

In response to route request 22, route planning module 94 generates a path 16 to the destination location by identifying, selecting and/or otherwise generating an appropriate path 16. In generating path 16, route planning module 94 considers a particular aspect of the state of mobile drive unit 20b, here its docking status. Based on the relevant aspect of the requesting mobile drive unit's state, route planning module 94 may determine that the requesting mobile drive unit 20b is prohibited from moving through particular cells 14, from traversing particular paths 16, and/or from utilizing particular equipment (e.g., a drive lift) within workspace 70, and/or that the state of mobile drive unit 20b places some other form of restriction on the path 16 that route planning module 94 can properly generate for mobile drive unit 20b.

In particular embodiments, the requesting mobile drive unit 20 may itself indicate the relevant state information to route planning module 94. For example, in the illustrated embodiment, mobile drive unit 20b may indicate its docking status in route request 22. In alternative embodiments, route planning module 94 may monitor one or more mobile drive units 20 operating in workspace 70 and may maintain the relevant state information as part of its normal operation. Additionally, in particular embodiments, route planning module 94 may instead retrieve the relevant state information from other components of inventory system 10 when a particular mobile drive unit 20 requests a path 16. For example, in particular embodiments, when route planning module 94 receives a route request 22 from a particular mobile drive unit 20, route planning module 94 may communicate with resource scheduling module 92 to determine whether the requesting mobile drive unit 20 is currently assigned a task.

In the illustrated example, it is assumed that mobile drive units 20 that are currently docked with an inventory holder 30 are not allowed to move through cells 14 of workspace 70 designated for the storage of inventory holders 30 (referred to as storage cells 64). Consequently, if mobile drive unit 20b is currently docked to an inventory holder 30, route planning module 94 may generate a path for mobile drive unit 20 that circumvents all designated storage cells, such as the path shown in FIG. 7 as path 16a. On the other hand, if mobile drive unit 20 is not currently docked to an inventory holder 30, route planning module 94 may generate a path that includes designated storage cells 64, such as the path shown in FIG. 7 as path 16b.

Once route planning module 94 has generated the appropriate path 16, route planning module 94 communicates path 16 to the requesting mobile drive unit 20. In the illustrated embodiment, route planning module 94 transmits a route response 24 to the mobile drive unit 20b that identifies path 16. Mobile drive unit 20b then completes the received path 16 as discussed above.

By considering the state of the requesting mobile drive unit 20 when generating path 16, route planning module 94 may make more intelligent decisions regarding paths 16 that route planning module 94 generates for that mobile drive unit 20. In particular embodiments, route planning module 94 may consider the state of a requesting mobile drive unit 20 to allow route planning module 94 to selectively use cells, paths, or equipment that might be prohibited for use by mobile drive units 20 of a certain state. Similarly, in particular embodiments, route planning module 94 may consider the state of a requesting mobile drive unit 20 to limit the use of particular cells, paths, or equipment by mobile drive units 20 of a particular state so that they can be available for use by mobile drive units 20 having states preferable for using the relevant cell, path, or equipment.

As one example, route planning module 94 may, as already discussed, consider the docking status of the requesting mobile drive unit 20 when generating the path. Similarly, in particular embodiments (for example, embodiments in which mobile drive units 20 do not actually dock with inventory holders 30 they transport), route planning module 94 may alternatively consider whether the requesting mobile drive unit 20 is carrying a load when generating the path. As a result, route planning module 94 may be able to selectively use a cell 14 that might otherwise be prohibited for use in routing because docked or loaded mobile drive units 20 cannot traverse the cell 14 in question due to the presence of a stored inventory holder 30, the position of overhanging stairs, or other physical limitations that prevent a docked or loaded mobile drive unit 20 from being able to cross cell 14. Consequently, cells 14 that would otherwise have to be prohibited from use in any paths may be selectively utilized in paths for appropriate mobile drive units 20, thereby increasing the space resources available to route planning module 94 for routing requested paths 16.

Additionally, route planning module 94 may use the docking or loading status of the requesting mobile drive unit 20 as a proxy for determining the urgency of the path 16 that mobile drive unit 20 is requesting. As a result, in particular embodiments, route planning module 94 may decide not to route undocked or unloaded mobile drive units 20 through cells in high-traffic areas even if the resulting path 16 is significantly longer. Similarly, in particular embodiments, route planning module 94 may decide not to generate paths for undocked or unloaded mobile drive units 20 that require the use of scarce equipment resources, such as drive lifts, to complete the paths. Consequently, route planning module 94 may generate prioritized routes for certain mobile drive units 20 based on the docking or loading status of those mobile drive units 20.

As another example, route planning module 94 may consider the power or fuel level of the requesting mobile drive unit 20 when generating path 16. As a result, route planning module 94 may, based on the charge or fuel level of the requesting mobile drive unit 20, generate a path 16 that is less than some maximum length to ensure the requesting mobile drive unit 20 does not end up stranded, even if this path will increase the probability that the requesting mobile drive unit 20 will be delayed by congestion. Similarly, route planning module 94 may decide based on the fuel or charge level of the requesting mobile drive unit 20 to generate a path that runs near a recharging or refueling station to allow the requesting mobile drive unit 20 to recharge or refuel while en route to the destination location.

As yet another example, route planning module 94 may also consider the current assignment state of a requesting mobile drive unit 20 in generating path 16 for that mobile drive unit 20. This assignment state may relate to whether that mobile drive unit 20 is currently assigned a task, the priority of that task, and/or any other consideration relating to the tasks currently or previously assigned to that mobile drive unit 20. As a result, in particular embodiments, route planning module 94 may only route mobile drive units 20 that are currently assigned a high-priority task through what would otherwise be high-traffic cells 14. Similarly, in particular embodiments, route planning module 94 may decide to generate a path that requires use of scare equipment resources, such as drive lifts, only if the requesting mobile drive unit 20 is currently assigned a task or, alternatively, a high-priority task. Consequently, in particular embodiments, route planning module 94 generates paths 16 that are quicker to complete for mobile drive units 20 currently assigned a task, or for those currently assigned a high-priority task.

As yet another example, particular embodiments of inventory system 10 may utilize mobile drive units 20 having different physical characteristics, such as height and width. In such embodiments, route planning module 94 may be configured to consider the physical characteristics of the requesting mobile drive unit 20 in generating path 16. As a result, in such an embodiment, the fact that it may be physically impossible for certain mobile drive units 20 to move through certain cells 14, follow certain paths 16, or use certain equipment, may not cause route planning module 94 to forgo use of such cells 14, paths 16, or equipment when generating paths for all mobile drive units 20.

In general, however, route planning module 94 may, in particular embodiments, consider any one or more aspects of the state of mobile drive unit 20, or of the load that mobile drive unit 20 is carrying, in generating a requested path 16. Consequently, route planning module 94 may, in particular embodiments, be able to further optimize the use of resource in inventory system 10 by tailoring path 16 to meet the requirements of the requesting mobile drive unit 20. Furthermore, by considering both the destination provided by mobile drive unit 20 and the state of the requesting mobile drive unit 20 in generating path 16, certain embodiments of route planning module 94 may be able to facilitate the completion of a second goal (such as recharging) with little or no impact on the ability of mobile drive unit 20 to complete its assigned task. As a result, particular embodiments of inventory system 10 that implement the techniques described with respect to FIG. 7 may provide a number of operational benefits.

FIG. 8 is a flowchart illustrating operation of an example embodiment of route planning module 94 in implementing some or all of the techniques described with respect to FIG. 7. While FIG. 8 focuses on a particular embodiment of inventory system 10 that considers a particular aspect of the state of a mobile drive unit 20 in generating a path 16 to a particular destination for that mobile drive unit 20, alternative embodiments of inventory system 10 may be configured to consider any appropriate aspect of the state of mobile drive units 20 when generating paths 16. Additionally, any of the steps illustrated in FIG. 8 may be combined, modified, or deleted where appropriate, and additional steps may also be added to those shown in the flowchart. Moreover, the described steps may be performed in any suitable order without departing from the scope of the invention.

Operation begins at step 640 with route planning module 94 receiving a route request 22 from a mobile drive unit 20. Route request 22 identifies a destination location within workspace 70. In particular embodiments, workspace 70 comprises at least one cell 14 associated with a first cell attribute and at least one cell that is not associated with the first cell attribute. For example, in particular embodiments, those cells 14 which require tunneling to traverse are associated with a tunneling attribute, while those cells which do not require tunneling are not associated with the tunneling attribute. In the illustrated example, all storage cells 64 in workspace 70 are associated with the tunneling attribute, and therefore require an mobile drive unit 20 to be tunneling to traverse them. By contrast, all cells 14 that are not storage cells 64 ("non-storage cells") in workspace 70 are not associated with the tunneling attribute, and these non-storage cells 64 can be traversed without tunneling.

At step 642, route planning module 94 determines a state of the mobile drive unit 20. As discussed above, route planning module 94 may determine the state of mobile drive unit 20 based on information included in route request 22 or other communication with the requesting mobile drive unit 20, information maintained by route planning module 94, information received from another component of inventory system 10, and/or any other suitable information. In response to determining that the requesting mobile drive unit 20 is associated with a first state, route planning module 94 generates a path 16 to the destination location for mobile drive unit 20 that may traverse cells 14 that are associated with the first cell attribute at step 644. In this case, the generated path 16 may traverse both cells that are associated with the first cell attribute and cells that are not associated with the first cell attribute. In response to determining mobile drive unit 20 is not associated with the first state, however, route planning module 94 generates a path 16 to the destination location for mobile drive unit 20 that does not traverse any cells 14 associated with the first cell attribute at step 646. In this case, the generated path 16 traverses only cells that are not associated with the first cell attribute. While, in particular embodiments, the generated path 16 may allow for a particular mobile drive unit 20 to enter and exit a cell associated with the first cell attribute from the same direction (e.g. to drop off an inventory holder 30 in an empty storage cell 64) the generated path 16, in such embodiments, will not allow or require the requesting mobile drive unit 20 to traverse any such cells 14.

For example, in particular embodiments, route planning module 94 may determine whether mobile drive unit 20 is currently in a docked or undocked state. If route planning module 94 determines at step 642 that the requesting mobile drive unit 20 is currently docked, route planning module 94 generates a path 16 between the first destination and the second destination that only includes cells 14 that are not designated as storage cells 64, such as path 16a in FIG. 7. Instead, if route planning module 94 determines that the requesting mobile drive unit 20 is not currently docked, route planning module 94 may generate a path 16 that includes cells 14 that are designated as storage cells 64 as well as cells 14 that are designated as non-storage cells, such as path 16b in FIG. 7.

After generating the appropriate path 16, route planning module 94 communicates path 16 to the requesting mobile drive unit 20. In the illustrated example, route planning module 94 communicates the generated path 16 to the requesting mobile drive unit 20 by transmitting a route response 24 to the requesting mobile drive unit 20 that specifies the generated path 16 at step 648. Route response 24 includes information defining the generated path 16. After receiving route response 24, mobile drive unit 20 may then begin traversing the generated path 16 to the destination location, and the operation of route planning module 94 with respect to generating this path 16 ends, as shown in FIG. 8.

Figure 9:
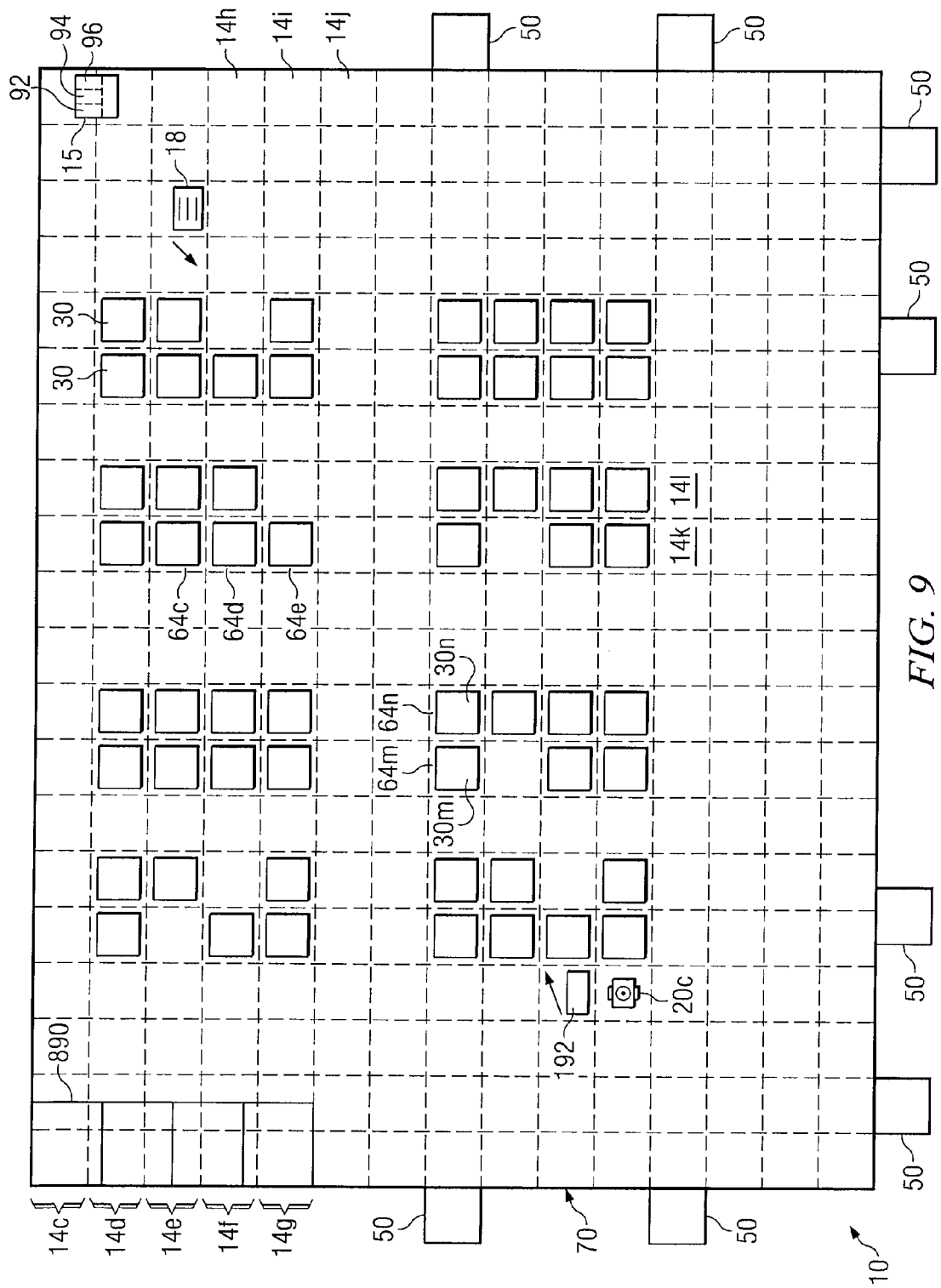
FIG. 9 illustrates an example embodiment of the inventory system capable of optimizing the placement of mobile drive units based on their assignment state.
Figure 10:
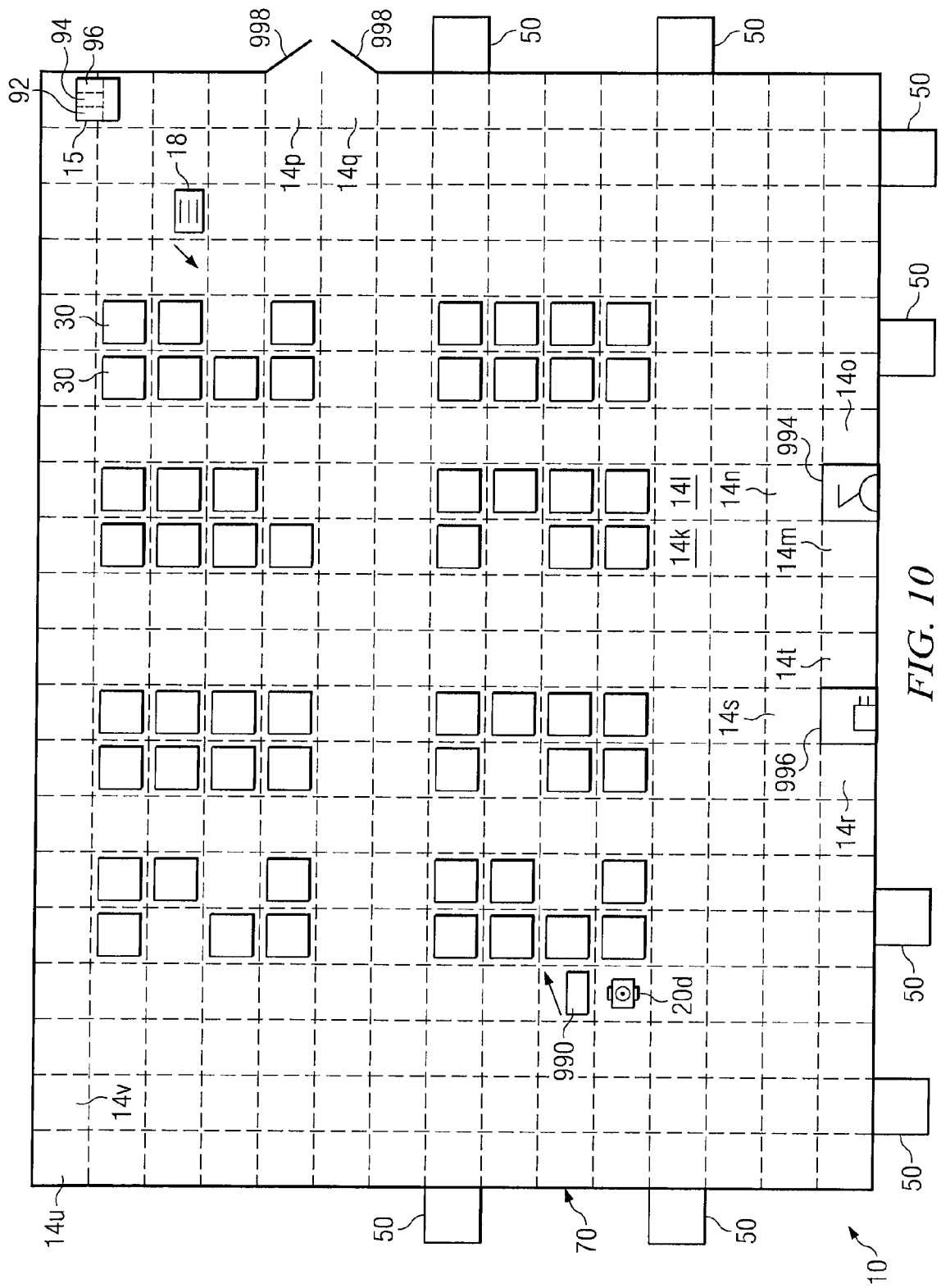
FIG. 10 illustrates an example embodiment of the inventory system capable of optimizing the placement of mobile drive units based on their capability state.
Figure 11:
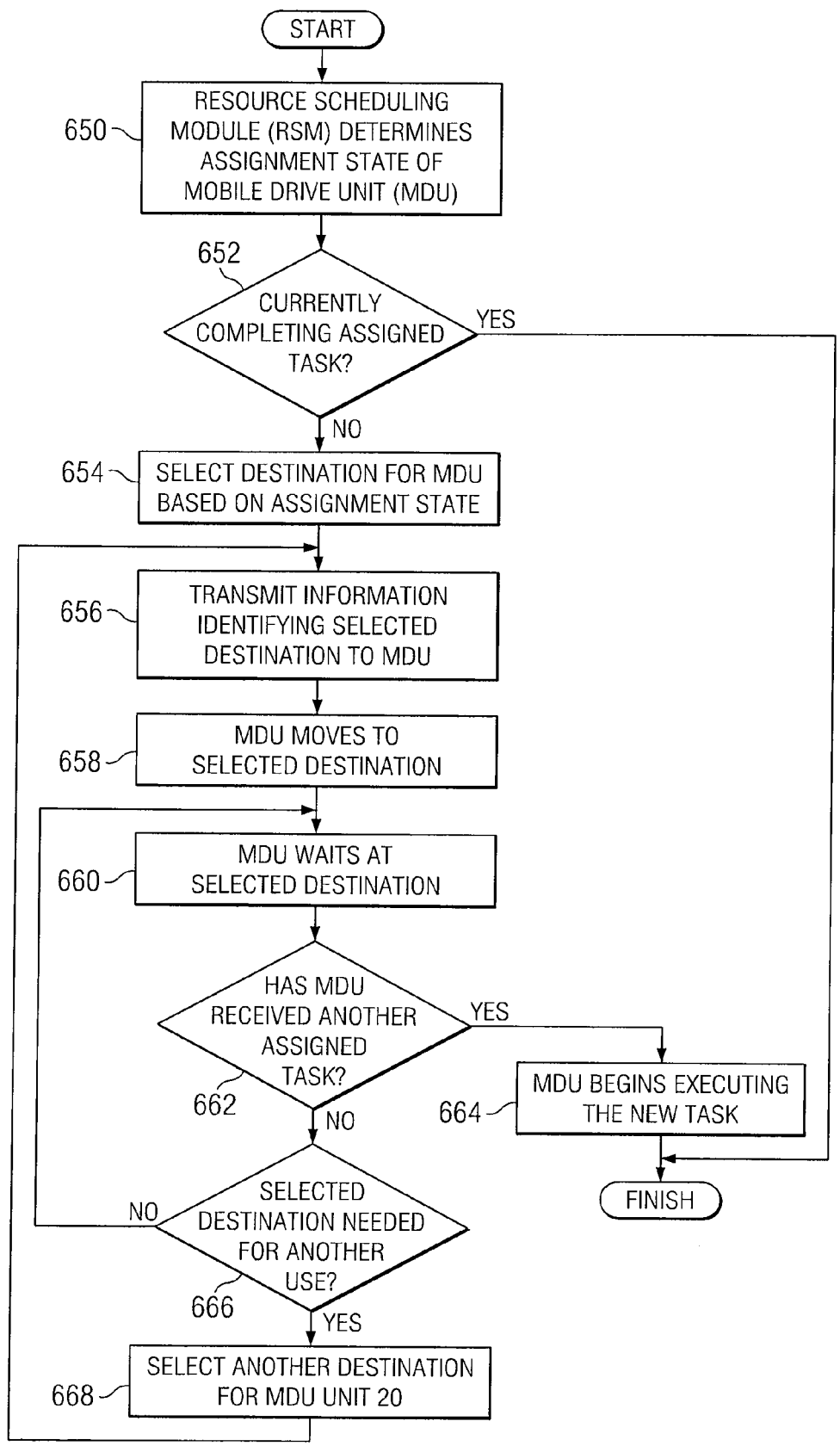
FIG. 11 is a flowchart detailing example operation of a particular embodiment of the management module in implementing the techniques described in FIG. 9.

FIGS. 9-11 illustrate techniques for selecting a destination for mobile drive unit 20 based on the state of the relevant mobile drive unit 20. More specifically, FIG. 9 illustrates an example of how management module 15 might utilize such techniques to select destinations for mobile drive units 20 based on their task assignments, while FIG. 10 illustrates an example of how management module 15 might utilize such techniques to select a destination for mobile drive units 20 based on their capability to complete tasks. Additionally, FIG. 11 is a flowchart illustrating example operation of management module 15 in a particular implementation of these techniques. As one example of how such a technique might be used in inventory system 10, in particular embodiments of inventory system 10, mobile drive units 20 and inventory holders 30 may be sized and shaped to allow an undocked mobile drive unit 20 and an inventory holder 30 to share the same portion of workspace 70, such as storage cells 64. As a result, management module 15 may instruct mobile drive units 20 that are not currently engaged in completing any assigned tasks to park in a space currently storing an inventory holder 30. This may reduce the possibility of an idle mobile drive unit 20 becoming an obstacle in workspace 70 and free more room for traffic. Additionally, these techniques may result in idle mobile drive units 20 being directed to a location selected to best situate the relevant mobile drive unit 20 for responding to its next assignment.

The example illustrated by FIG. 9 begins with resource scheduling module 92 determining a state of mobile drive unit 20c. In particular, in this example, resource scheduling module 92 determines an assignment state of mobile drive unit 20c. The assignment state may relate to whether the relevant mobile drive unit 20 is currently assigned one or more tasks, is actively engaged in completing one or more tasks, has just completed one or more previously-assigned tasks, and/or any other consideration associated with the tasks that have been assigned to and/or completed by mobile drive unit 20c.

Additionally, resource scheduling module 92 may determine the assignment state of a particular mobile drive unit 20 in any appropriate manner. In particular embodiments, mobile drive units 20, upon completing a task, notify resource scheduling module 92 of the fact that they have completed their currently assigned tasks. In the illustrated example, mobile drive unit 20c notifies resource scheduling module 92 by transmitting a task completion message 192. Task completion message 192 indicates to resource scheduling module that the mobile drive unit 20 that transmitted task completion message 192 has completed its currently-assigned task. Task completion message 192 may include an identifier for the idle mobile drive unit 20 and/or other information suitable to allow resource scheduling module 92 to determine that the relevant mobile drive unit 20 has completed its task. As a result, resource scheduling module 92 determines the assignment state of mobile drive unit 20c based on receipt of task completion message 192. In alternative embodiments, resource scheduling module 92 may monitor one or more mobile drive units 20 operating in workspace 70 and may maintain the relevant state information as part of its normal operation.

In response to determining that mobile drive unit 20c has completed its assigned tasks, resource scheduling module 92 selects a destination for mobile drive unit 20c that is chosen based on the fact that mobile drive unit 20c is idle. Depending on the configuration of inventory system 10, resource scheduling module 92 may use the knowledge that mobile drive unit 20c is idle in any suitable manner in selecting an appropriate destination for mobile drive unit 20c. By providing special treatment for idle mobile drive units 20, resource scheduling module 92 may selectively place these mobile drive units 20 to improve the overall effectiveness of inventory system 10.

In particular embodiments, resource scheduling module 92 may direct mobile drive unit 20c to low-traffic locations to prevent mobile drive unit 20c from creating congestion while it awaits another task. As one example, resource scheduling module 92 may select a destination location from among storage cells 64 that currently hold a stored inventory holder 30. Storage cells 64c, 64d, and 64e in FIG. 9 illustrate examples of such locations.

As another example, resource scheduling module 92 may direct mobile drive unit 20c to a low-traffic destination by selecting a cell 14 that is otherwise inaccessible by mobile drive units 20, as a destination and/or to move through, that are currently docked with an inventory holder 30. For example, in particular embodiments, resource scheduling module 92 may identify a destination from among cells 14 in workspaces that have overhanging staircases, narrow entryways, low ceilings, and/or are otherwise inaccessible by mobile drive units 20 docked with the inventory holders 30 used in that embodiment of inventory system 10. This may help ensure that mobile drive units 20 transporting inventory holders 30 will not need to use the cell 14 selected as a parking space for mobile drive unit 20c. Workspace 70 illustrated in FIG. 9 includes a stairway 890 that prevents mobile drive units 20 transporting inventory holders 30 from moving through at least cells 14c-14g. As a result, cells 14c-14g illustrate an example of this type of inaccessible cell in FIG. 9.

As yet another example, in particular embodiments resource scheduling module 92 may direct mobile drive unit 20c to a low-traffic destination by selecting a destination location based on the actual traffic flow through the relevant area. For example, resource scheduling module 92 may consider the frequency with which a particular cell 14 is included in paths 16 generated by route planning module 94, the frequency with which segments that include that cell 14 are requested for reservation, and/or any other appropriate indicator of traffic flow, and may then select a destination for mobile drive unit 20c from among cells 14 that are only infrequently used by mobile drive units 20. Cells 14h-14j in FIG. 9 are assumed, for the purposes of this example, to be infrequently used by mobile drive units 20 and thus illustrate an example of this type of location.

Additionally, resource scheduling module 92 may attempt to improve operation of inventory system 10 by placing mobile drive unit 20c in an optimal position for responding to subsequent tasks assigned to mobile drive unit 20c. For example, in particular embodiments, resource scheduling module 92 may select a destination location for mobile drive unit 20c that is close to stored inventory holders 30. Cells 14k-14l in FIG. 9 illustrate generic examples of this type of location.

Furthermore, in particular embodiments, resource scheduling module 92 may select a destination for mobile drive unit 20c that is close to frequently-requested inventory holders 30. For example, in a mail-order warehouse, resource scheduling module 92 may select a destination for mobile drive unit 20c near inventory holders 30 that store top-selling inventory items 40. As a result, in such embodiments, resource scheduling module 92 may consider the frequency with which particular inventory holders 30 are used in responding to inventory requests and select a location for mobile drive unit 20c that is near a frequently-requested inventory holder 30. Moreover, in particular embodiments, resource scheduling module 92 may attempt to achieve both goals by selecting a destination for mobile drive unit 20c that is located in a storage cell 64 that holds a frequently-requested inventory holder 30. As a result, mobile drive unit 20c may be kept out of traffic and also optimally positioned for responding to subsequent tasks likely to be assigned to mobile drive unit 20. For the purposes of this example, inventory holders 30m and 30n are assumed to be frequently-requested inventory holders. As a result, due to the fact that storage cells 64m and 64n are each currently storing an inventory holder 30 and, in particular, an inventory holder 30 that is frequently requested, storage cells 64m and 64n in FIG. 9 represent example locations that satisfy both goals.

More generally, resource scheduling module 92 may select any particular type of location as a destination for a mobile drive unit 20 having a particular assignment status. Additionally, while FIG. 9 illustrates an example configuration in which particular types of cells 14 that may be selected as destinations are located in particular locations in workspace 70, resource scheduling module 92 may utilize destinations of any type located anywhere within workspace 70.

After selecting a destination for mobile drive unit 20c, resource scheduling module 92 communicates the destination location to mobile drive unit 20c. In the illustrated embodiment, resource scheduling module 92 transmits a task assignment 18 that identifies the selected destination location. In particular embodiments, mobile drive unit 20c may then request a path and move to the destination, as described with respect to FIG. 5. In particular embodiments, mobile drive unit 20 may then wait at the destination until receiving another task assignment 18.

Thus, by selecting parking locations in low-traffic areas for idle mobile drive units 20, a particular embodiment of resource scheduling module 92 may reduce the probability that such mobile drive units 20 will create congestion while they wait for further assignments. Furthermore, by placing idle mobile drive units 20 near inventory holders 30 or other appropriate components of inventory system 10, resource scheduling module 92 can reduce the completion time for future tasks that idle mobile drive units 20 are assigned. More generally, a particular embodiment of inventory system 10 may be configured to use the knowledge that a particular mobile drive unit 20 is idle in any appropriate manner to select a destination for that mobile drive unit 20. By strategically placing mobile drive units 20 when they are not being used, resource scheduling module 92 can further increase the overall efficiency and throughput of inventory system 10.

FIG. 10 illustrates another example of how resource scheduling module 92 may use various aspects of the state of a mobile drive unit 20 to determine a location for that mobile drive unit 20. More specifically, FIG. 10 illustrates how resource scheduling module 92 may use a capability state of a mobile drive unit 20 to determine a location for that mobile drive unit 20. By determining an appropriate destination for a mobile drive unit 20 based on the repair status, energy supply status, and/or any other consideration relating to the ability of that mobile drive unit 20 to complete assigned tasks, in general, and/or to complete a particular assigned task, resource scheduling module 92 may optimize the placement of mobile drive units 20 in need of repair, re-supply, and/or other types of maintenance to regain or improve their capability of completing assigned tasks.

The example illustrated by FIG. 10 begins with resource scheduling module 92 determining the state or a particular aspect of the state of mobile drive unit 20d. In particular, in this example, resource scheduling module 92 determines a capability state of mobile drive unit 20d. The capability state may relate to the repair status, supply status, maintenance status, and/or any other aspect of the mobile drive units current ability or anticipated future ability to complete assigned tasks.

Resource scheduling module 92 may determine the capability state of mobile drive unit 20d in any appropriate manner. In the illustrated embodiment, mobile drive units 20d is configured to transmit a capability message 990 when its capabilities change and/or an event affecting its capabilities occurs. For example, a mobile drive unit 20 may transmit a capability message 990 when its fuel level or battery charge level drops, parts or components of mobile drive unit 20d break or become unusable, a scheduled maintenance period for mobile drive unit 20d elapses, or any other event occurs affecting or potentially affecting the ability of mobile drive unit 20d to complete assigned tasks and/or remain active. In alternative embodiments, resource scheduling module 92 may monitor various characteristics of mobile drive units 20 or events associated with mobile drive units 20 as part of its normal operation and determine the capability state of mobile drive units 20 based on the monitored information. In yet other embodiments, resource scheduling module 92 may receive information from other components of inventory system 10 from which resource scheduling module 92 determines the capability state of mobile drive units 20. In general, however, resource scheduling module 92 may determine the capability state of a particular mobile drive unit 20 using any appropriate information obtained from any suitable source.

Returning to the illustrated example, resource scheduling module 92, after determining the capability state of mobile drive unit 20d from capability message 990, selects a location for mobile drive unit 20d based on this capability state. Resource scheduling module 92 then generates a task assignment 18 identifying the selected location and transmits task assignment 18 to mobile drive unit 20 for completion. By selecting a destination appropriate for mobile drive unit 20 based on its capability state, resource scheduling module 92 may be able to reduce the effects of damage, energy depletion, and other debilitating occurrences on the congestion, throughput, and responsiveness of inventory system 10.

As one example, in particular embodiments, the capability state of mobile drive unit 20d may relate to its state of repair. If any components, or a specific component, of mobile drive unit 20d breaks or becomes unusable, mobile drive unit 20 may transmit capability message 990 to resource scheduling module 92. Resource scheduling module 92 may then select a destination for mobile drive unit 20 based on the knowledge that mobile drive unit 20d needs repair. In particular embodiments, inventory system 10 may include automated repair stations 992 that are capable of repairing certain types of malfunctions or replacing certain types of parts. For example, inventory system 10 may include an automated repair station 992 that can replace blown tires, clean sensors, or perform other types of repairs with limited or no human involvement. In such embodiments, resource scheduling module 92 may select a destination at or near an appropriate automated repair station 992, such as cells 14m, 14n, and 14o, in response to determining mobile drive unit 20d needs repair or, in response to determining mobile drive unit 20d needs a particular type of repair.

As another example, in particular embodiments, inventory system 10 may include cells 14, such as cells 14p and 14q that provide easy access for human operators attempting to repair mobile drive units 20, and resource scheduling module 92 may be configured to send mobile drive units 20 to these cells for at least certain types of repairs. In particular embodiments, such as the one illustrated in FIG. 10, some or all of workspace 70 may be enclosed by a wall, railing, or other barrier that prevents or limits entry to workspace 70 and resource scheduling module 92 may select a destination near access points to workspace 70 (such as doors 998 in FIG. 10). Alternatively or additionally, resource scheduling module 92 may select a destination that is located away from high-traffic areas, reserved for repair work, or otherwise situated to allow human operators safe and/or easy access to mobile drive units needing repair. Thus, in response to determining drive unit 20d needs repair or, in response to determining mobile drive unit 20d needs a particular type of repair (e.g., a type of repair too complicated for automated repair station 994), resource scheduling module 92 may select a destination, such as cells 14p and 14q, for mobile drive unit 20d that is easily accessible to human operators.

As yet another example, in particular embodiments, the capability state of mobile drive unit 20d may relate to its fuel or charge level. For example, in particular embodiments, mobile drive unit 20d may transmit capability message 990 indicating its fuel level, battery charge, or other appropriate form of energy level to resource scheduling module 92. Resource scheduling module 92 may then select an appropriate destination for mobile drive unit 20d based on this information. In particular embodiments, inventory system 10 may include one or more energy stations 996 at which mobile drive units 20 may be recharged or refueled, receive a new battery, or otherwise receive additional energy for responding to assigned tasks. Thus, in response to determining drive unit 20d needs refueling or recharging, resource scheduling module 92 may select a destination, such as cells 14r, 14s, or 14t, that is close to an appropriate energy station 996.

As yet another example, in particular embodiments, resource scheduling module 92 may be configured to send mobile drive units 20 that need repair, refuel, or recharging to low-traffic cells 14. Consequently, in such embodiments, mobile drive units 20 that are not capable of completing assigned tasks will not impede traffic while awaiting repair or removal from inventory system 10. In doing so, resource scheduling module 92 may consider the frequency with which a particular cell 14 is included in paths 16 generated by route planning module 94, the frequency with which segments that include that cell 14 are requested for reservation, and/or any other appropriate indicator of traffic flow, and may then select a destination for mobile drive unit 20d from among cells 14 that are only infrequently used by mobile drive units 20. Additionally, when selecting a destination for such mobile drive units 20, resource scheduling module 92 may consider the fact that, because of physical constraints, system policies, and/or any other suitable considerations a particular cell 14 is not otherwise available as a destination for mobile drive units 20 and/or for mobile drive units 20 to move through. In FIG. 10, cells 14u and 14v in are assumed, for the purposes of this example, to be infrequently used by mobile drive units 20 and thus illustrate an example of this type of location. Thus, in response to determining drive unit 20d needs repair or, in response to determining mobile drive unit 20d needs a particular type of repair, resource scheduling module 92 may select a destination in a low-traffic area, such as cells 14u or 14v.

As yet another example, resource scheduling module 92 may select a particular task or tasks for a mobile drive unit 20 based on the degraded capabilities of mobile drive unit 20. Thus, when resource scheduling module 92 detects that a mobile drive unit 20 is in a state of disrepair, low on batteries or fuel, or otherwise in a state of degraded capabilities, resource scheduling module 92 may assign that mobile drive unit 20 a task associated with lighter inventory holders 30, inventory holders 30 closer to the position of the mobile drive unit 20, or otherwise better suited for transport by the degraded mobile drive unit 20 than the inventory holders 30 associated with other tasks. As a result, resource scheduling module 92 may select for the relevant mobile drive unit 20 a destination location associated with such inventory holders 30.

More generally, resource scheduling module 92 may select any particular type of location as a destination for a mobile drive unit 20 having a particular capability state. Additionally, while FIG. 10 illustrates an example configuration in which particular types of cells 14 that may be selected as destinations are located in particular locations in workspace 70, resource scheduling module 92 may utilize destinations of any type located anywhere within workspace 70.

After resource scheduling module 92 selects an appropriate destination for mobile drive unit 20*d* based on its capability state, resource scheduling module 92 communicates the destination to mobile drive unit 20*d*. In the illustrated example, communicates the destination by transmitting a task assignment 18 to mobile drive unit 20*d* that identifies the selected destination. Mobile drive unit 20*d* then requests a path 16 to the selected destination and travels the path to the selected destination as described above with respect to FIG. 5. In particular embodiments, mobile drive unit 20 may then remain at the selected destination until being repaired or receiving appropriate maintenance. Mobile drive unit 20 may then become available to receive other task assignments from resource scheduling module 92.

Although the above description focuses on an example in which mobile drive unit 20*d* transmits information indicating its capability state to resource scheduling module 92, in particular embodiments, resource scheduling module 92 may instead determine the capability state of a particular mobile drive unit 20 based on information resource scheduling module 92 retrieves from a source other than the relevant mobile drive unit 20. For example, in particular embodiments, mobile drive unit 20 may be repaired or maintained according to a repair or maintenance schedule, and resource scheduling module 92 may determine the capability state of a particular mobile drive unit 20 based on this schedule and stored information indicating the last time the relevant mobile drive unit 20 was repaired or received maintenance.

Thus, by selecting parking spaces for mobile drive units 20 that increase the speed or ease with which mobile drive units 20 can be repaired, refueled, recharged, maintained, or otherwise have their capabilities restored, resource scheduling module 92 can limit the negative impact of mobile drive units 20 that are damaged, expended, or otherwise incapable of completing assigned tasks. Moreover, by choosing parking spaces in low-traffic areas for such mobile drive units 20, particular embodiments of resource scheduling module 92 may reduce the probability that such mobile drive units 20 will create congestion while they await repair or maintenance. More generally, a particular embodiment of inventory system 10 may be configured to use the knowledge that a particular mobile drive unit 20 is damaged, expended, or otherwise incapable of completing assigned tasks in any appropriate manner to select a destination for that mobile drive unit 20. By strategically locating mobile drive units 20 that are in such a state, resource scheduling module 92 can further increase the overall efficiency and throughput of inventory system 10.

FIG. 11 is a flowchart illustrating the operation of a particular embodiment of resource scheduling module 92 in selecting a destination location for a mobile drive unit 20. More specifically, FIG. 11 illustrates the process by which resource scheduling module 92, in particular embodiments of inventory system 10, selects a destination for a particular mobile drive unit 20 based on the state of that mobile drive unit 20. Although FIG. 11 focuses on an example in which resource scheduling module 92 selects a destination for mobile drive unit 20 based on an assignment state of the mobile drive unit 20, particular embodiments of resource scheduling module 92 may be configured to instead select a destination based on a capability state or any other aspect of the overall state of the relevant mobile drive unit 20. Additionally, any of the steps illustrated in FIG. 11 may be combined, modified, or deleted where appropriate, and additional steps may also be added to those shown in the flowchart. Moreover, the described steps may be performed in any suitable order without departing from the scope of the invention.

Operation, in this example, begins with resource scheduling module 92 determining an assignment state of a particular mobile drive unit 20 at step 650. As noted above, the assignment state may relate to whether the mobile drive unit 20 is currently assigned one or more tasks, is actively engaged in completing one or more tasks, and/or has just completed one or more previously-assigned tasks, and/or any other aspect of the tasks that have been assigned to and/or completed by mobile drive unit 20. At step 652, resource scheduling module 92 determines, based on this assignment state, whether mobile drive unit 20 is currently completing any assigned tasks. If resource scheduling module 92 determines that mobile drive unit 20 is currently completing an assigned task, resource scheduling module 92 may allow mobile drive unit 20 to complete its assigned task and operation of resource scheduling module 92 with respect to selecting a destination for that mobile drive unit 20 may end as shown in FIG. 11.

If, instead, resource scheduling module 92 determines that mobile drive unit 20 is not currently completing any assigned tasks, resource scheduling module 92 selects a destination for mobile drive unit 20, at step 654, based on the assignment state of mobile drive unit 20. Depending on the configuration of resource scheduling module 92, resource scheduling module 92 may select any appropriate destination for mobile drive unit 20 based on its assignment state. In particular embodiments, resource scheduling module 92 may select a low-traffic destination or a destination near locations associated with anticipated future tasks. Thus, in response to determining that mobile drive unit 20 is idle, resource scheduling module 92 may select a location based on a traffic level associated with the destination, based on its proximity to inventory holders 30, or based on any other consideration appropriate a state of the mobile drive unit 20.

At step 656, resource scheduling module 92 transmits information identifying the selected destination to mobile drive unit 20. In particular embodiments, resource scheduling module 92 transmits a task assignment 18 that includes the selected destination. At step 658, mobile drive unit 20 moves to the selected destination.

Mobile drive unit 20 then waits until it receives another assigned task at step 660. Thus, at step 662, mobile drive unit 20 determines whether mobile drive unit 20 has received another assigned task. If so, mobile drive unit 20 begins executing the assigned task at step 664, and the operation of resource scheduling module 92 with respect to selecting a destination for mobile drive unit 20 ends as shown in FIG. 11.

While mobile drive unit 20 is waiting for another assigned task, resource scheduling module 92 may determine, at step 666, that a portion of workspace 70 associated with the selected destination, such as a cell 14 that contains the selected destination, is needed for another use. As a result, resource scheduling module 92 may select another destination for mobile drive unit 20 at step 668, and operation may return to step 656 with resource scheduling module 92 transmitting information identifying the newly-selected location to mobile drive unit 20.

FIGS. 12A-12E, 13, and 14 illustrate a technique for managing the coordinated movement, or "platooning," of mobile drive units 20. More specifically, FIGS. 12A-12E illustrate an example of how coordinated movement techniques might be implemented and utilized in a particular embodiment of inventory system 10. FIG. 13 is a flowchart illustrating example operation of management module 15 in utilizing a particular implementation of these techniques, while FIG. 14 is a flowchart illustrating example operation of a mobile drive unit 20 in utilizing a particular implementation of these techniques.

As one example of how such a technique might be implemented and utilized in inventory system 10, management module 15 may employ modified reservation policies for a group of mobile drive units 20 that are moving in the same direction. In particular, one or more mobile drive units 20 in the rear of the group may be allowed to reserve a segment 17 that includes a particular cell 14 occupied by the mobile drive unit 20 in front of that mobile drive unit 20 before the front mobile drive unit 20 vacates the relevant cell 14, based on the expectation that the mobile drive unit(s) 20 in the front will be moving at the same time that the mobile drive unit(s) 20 in the back are moving and that, as a result, a collision will not occur despite the relaxed reservation policy.

Figure 12A:
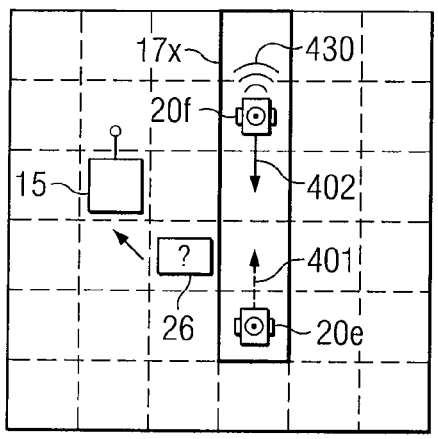
FIGS. 12A-12E illustrate an example of coordinated movement that may be executed by particular embodiments of the mobile drive unit.
Figure 12B:
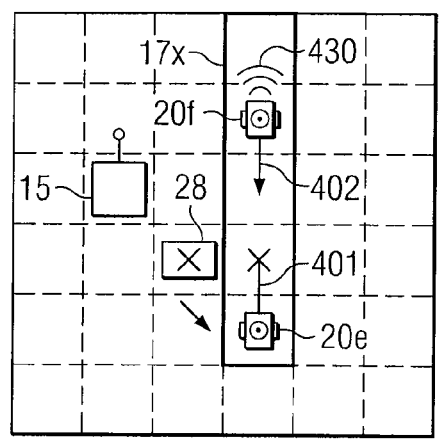

FIGS. 12A-12B illustrate an example of how these policies might be implemented in the case of mobile drive units 20 that are not moving in the same direction. More specifically, FIGS. 12A-12B show an example in which mobile drive unit 20e is attempting to reserve a path segment 17x to move in the direction indicated by arrow 401. In the illustrated example, segment 17x is presently reserved and occupied by mobile drive unit 20f. Moreover, mobile drive unit 20e is attempting to move towards mobile drive unit 20f as indicated by arrow 402. FIGS. 12A and 12B also show a drive identification signal 430 that is generated by mobile drive unit 20f and described in greater detail below with respect to FIGS. 12C-12E.

FIG. 12A shows the location of mobile drive units 20e and 20f, in this example, when mobile drive unit 20e attempts to reserve segment 17x. As shown in FIG. 12A, mobile drive unit 20e attempts to reserve segment 17x by transmitting reservation request 26 to management module 15. Similar to the result under the reservation policies described above with respect to FIG. 5, this reservation request 26 will be denied even under the modified reservation policies utilized in this example, because mobile drive unit 20f already occupies cell 14xx on the requested segment 17x and mobile drive unit 20e and mobile drive unit 20f are not moving in the same direction. In the illustrated example, management module 15 notifies mobile drive unit 20e that the attempted reservation was unsuccessful by transmitting reservation response 28 indicating that the reservation was unsuccessful, as shown in FIG. 12B.

Additionally, in particular embodiments, mobile drive units 20e may be equipped with an obstacle sensor that senses objects in the path of mobile drive unit 20e, including other mobile drive units 20. As a result, mobile drive unit 20e may stop moving if mobile drive unit 20e detects mobile drive unit 20f in its path while in transit, or may refrain from requesting a reservation if mobile drive unit 20e detects mobile drive unit 20f on a segment 17, such as segment 17x, that mobile drive unit 20e is attempting to reserve. Consequently, in particular embodiments, mobile drive unit 20e may not even attempt to reserve segment 17x if mobile drive unit 20e detects mobile drive unit 20f on segment 17x as is shown in the example.

Figure 12C:
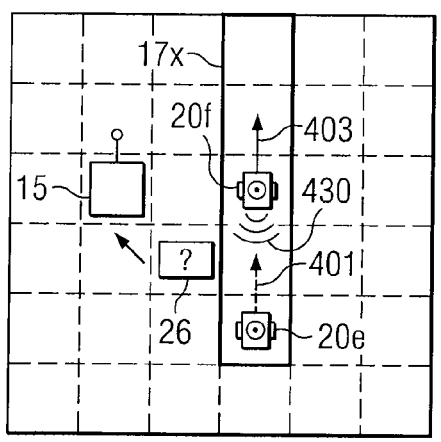
Figure 12D:
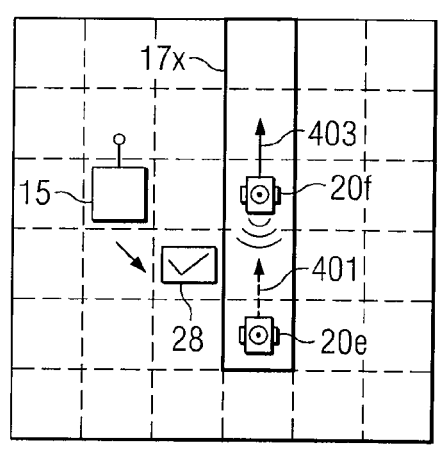
Figure 12E:
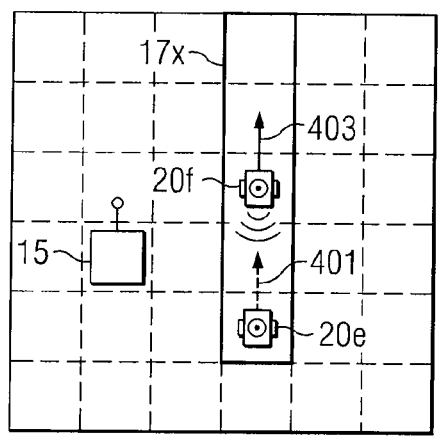

FIGS. 12C-12E illustrate an example of how the modified policies might operate in the case of mobile drive units 20 that are moving in the same direction. In FIGS. 12C-12E, mobile drive unit 20e is again attempting to reserve path segment 17x to move in the direction indicated by arrow 401. As in the previous illustrations, segment 17x is already reserved and occupied by mobile drive unit 20f. In this case, however, mobile drive unit 20f is attempting to move away from mobile drive unit 20e as indicated by arrow 403.

FIG. 12C shows the location of mobile drive units 20e and 20f when mobile drive unit 20e attempts to reserve segment 17x. As shown in FIG. 12C, mobile drive unit 20e again attempts to reserve segment 17x by transmitting a reservation request 26 to management module 15. In this case, however, segment reservation module 96 (or another appropriate component of management module 15) determines that mobile drive unit 20f is moving in the same direction as mobile drive unit 20e. As a result, segment reservation module 96 decides that it is acceptable to allow mobile drive unit 20e to reserve segment 17x sooner than mobile drive unit 20e would otherwise be able to do so. As a result, management module 15 may transmit a reservation response 28 indicating that mobile drive unit 20f has successfully reserved segment 17, as shown in FIG. 12D.

Consequently, in particular embodiments, mobile drive unit 20e may be able to successfully request reservations that overlap with the reservations of mobile drive unit 20f based on the fact that mobile drive units 20e and 20f are moving in the same direction as one another. Additionally, depending on the specific policies implemented by the relevant embodiment of inventory system 10, mobile drive unit 20e may also be permitted to move into a given cell 14 earlier than would otherwise be allowed. As a result, in particular embodiments, mobile drive unit 20e may, at particular times during its movement along segment 17x, occupy a portion of the same cell 14 as mobile drive unit 20e, as shown in FIG. 12E. Thus, the modified reservation policies shown in FIGS. 12C-12E allow for mobile drive units 20 traveling in the same direction to follow one another with a much smaller distance separating them than would otherwise be allowed.

Additionally, as noted above, mobile drive unit 20e may also include a collision detector capable of detecting obstacles in its way. If the collision detector detects an obstacle in the path of mobile drive unit 20e, the collision detector may prevent mobile drive unit 20e from moving even if mobile drive unit 20e has successfully reserved the segments 17 in its path. Therefore, in embodiments of inventory system 10 in which mobile drive units 20 utilize such collision detectors, mobile drive units 20 may also be configured to transmit a drive identification signal 430, as shown in FIGS. 12A-12E.

Drive identification signal 430 may represent any appropriate form of signal that indicates to other mobile drive units 20 that the object transmitting drive identification signal 430 is itself a mobile drive unit 20. Examples of drive identification signals include, but are not limited to, audio, visible light, radio, infra-red, and ultraviolet signals. In particular embodiments, drive identification signal 430 may comprise a line-of-sight signal, and mobile drive units 20 may transmit drive identification signal 430 in a direction opposite the direction in which they are traveling. As a result, only mobile drive units 20 positioned behind the transmitting mobile drive unit 20 (relative to the direction the transmitting mobile drive unit 20 is traveling) will be able to detect drive identification signal 430. Consequently, mobile drive units 20 that do detect drive identification signal 430 can determine, based on this detection, that the obstacle they are detecting is in fact a mobile drive unit 20 moving away from them and these mobile drive units 20 may override their collision detectors as a result of this determination.

Furthermore, in addition to identifying the transmitting mobile drive unit 20 as a mobile drive unit, drive identification signal 430 may carry additional information about the transmitting mobile drive unit 20 to allow any nearby mobile drive unit 20 to modify its movement based on the movement or planned movement of the transmitting mobile drive unit 20. For example, drive identification signal 430 may contain the current speed, current acceleration/deceleration, destination, size, and/or location of the transmitting mobile drive unit 20 and/or any other appropriate information to be used by mobile drive units 20 trying to navigate within the vicinity of the transmitting mobile drive unit 20. As a result, when the transmitting mobile drive unit 20 adjusts its speed or direction, mobile drive units 20 following behind it can detect this adjustment based on information contained in drive identification signal 430. The trailing mobile drive units 20 may then adjust their own speed in response and avoid collisions when the transmitting mobile drive unit 20 brakes or otherwise decelerates.

Thus, in the example illustrated by FIGS. 12C-12E, mobile drive unit 20f transmits drive identification signal 430 that informs mobile drive unit 20e that mobile drive unit 20f is a mobile drive unit 20 and that it is traveling at a particular speed. When mobile drive unit 20e detects drive identification signal 430 transmitted by mobile drive unit 20f, mobile drive unit 20e determines that the object detected by its collision detector is in fact a mobile drive unit 20 moving in the opposite direction. As a result, mobile drive unit 20e overrides its collision detector and proceeds in the direction of mobile drive unit 20f, as shown by the dotted-line silhouette in FIG. 12E. As mobile drive unit 20f adjusts its speed, mobile drive unit 20e detects the change based on information in drive identification signal 430 and adjusts its own speed to match. As a result, mobile drive unit 20e is able to follow closely behind mobile drive unit 20f while they are traveling in the same direction while limiting or eliminating the possibility of a collision between mobile drive units 20e and 20f.

FIG. 13 is a flowchart illustrating example operation of segment reservation module 96 in implementing the techniques described above. In particular, FIG. 13 details operation of a particular embodiment of segment reservation module 96 in managing the movement of a first mobile drive unit 20 and a second mobile drive unit 20 that may be operating in close proximity to one another. Any of the steps illustrated in FIG. 13 may be combined, modified, or deleted where appropriate, and additional steps may also be added to those shown in the flowchart. Moreover, the described steps may be performed in any suitable order without departing from the scope of the invention.

Operation begins, at step 670, with resource scheduling module 92 receiving, from first mobile drive unit 20, a reservation request 26 requesting use of a path segment 17 to move in a first direction. Prior to or after receiving reservation request 26, resource scheduling module 92 determines that a second mobile drive unit 20 is currently located on the requested path segment 17 at step 672. Because the second mobile drive unit 20 is currently located on the requested path segment 17, resource scheduling module 92 determines whether the second mobile drive unit 20 is moving in the first direction at step 674.

If resource scheduling module 92 determines that the second mobile drive unit 20 is moving in the first direction, resource scheduling module 92 grants the reservation. As a result, resource scheduling module 92 reserves the requested path segment 17 at step 676. At step 678, resource scheduling module 92, in particular embodiments, then transmits a reservation response 28 indicating that the requested reservation was successful.

If resource scheduling module 92 determines that the second mobile drive unit 20 is not moving in the first direction, resource scheduling module 92 denies the reservation. In particular embodiments, resource scheduling module 92 may then transmit a reservation response 28 to the first mobile drive unit 20, at step 680, indicating that the first mobile drive unit 20 did not successfully reserve the requested segment 17. The operation of resource scheduling module 92 with respect to responding to reservation request 26 may then end, as shown in FIG. 13.

FIG. 14 is a flowchart illustrating example operation of a mobile drive unit 20 in implementing the techniques described above. In particular, FIG. 14 details the decision-making utilized in particular embodiments of inventory system 10 by a first mobile drive unit 20 operating in close proximity to a second mobile drive unit 20. Any of the steps illustrated in FIG. 14 may be combined, modified, or deleted where appropriate, and additional steps may also be added to those shown in the flowchart. Moreover, the described steps may be performed in any suitable order without departing from the scope of the invention.

Operation begins at step 702 with the first mobile drive unit 20 receiving a command instructing it to move in a first direction. This command may represent a task assignment 18 assigning mobile drive unit 20 a task associated with a destination in the first direction, a route response 24 identifying a path 16 heading in the first direction, and/or any other appropriate form of command instructing the first mobile drive unit 20 to move in the first direction. At step 704, the first mobile drive unit 20 begins moving in the first direction along a path segment 16.

At step 706, the first mobile drive unit 20 detects an object located in the first direction along the path segment 16. In particular embodiments, mobile drive units 20 include an obstacle sensor 160 capable of detecting objects in the paths of mobile drive units 20. Thus, in such embodiments, the obstacle sensor 160 of first mobile drive unit 20 may detect the object.

At step 708, the first mobile drive unit 20 determines whether the detected object is another mobile drive unit 20 moving in the first direction. In particular embodiments, mobile drive units 20 transmit drive identification signals 430 that identify them as mobile drive units 20. Moreover, in particular embodiments, mobile drive units 20 transmit drive identification signal 430 in a direction opposite their direction of travel. As a result, only mobile drive units 20 behind a transmitting mobile drive units 20 (relative to the direction of travel of the transmitting mobile drive unit 20) receive the drive identification signal 430 transmitted by the transmitting mobile drive unit 20. Thus, in such embodiments, the first mobile drive unit 20 may determine whether the detected object is a second mobile drive unit 20 moving in the first direction by determining whether the first mobile drive unit 20 detects a drive identification signal 430 transmitted by the object.

If the first mobile drive unit 20 determines that the detected object is not a second mobile drive unit 20 traveling in the second direction, the first mobile drive unit 20 may terminate movement in the first direction at step 710. The first mobile drive unit 20 may then wait until the first mobile drive unit 20 no longer detects the detected obstacle in its path, move around the detected obstacle, request a new path, and/or take any other remedial action appropriate based on the configuration of the first mobile drive unit 20. Operation may then end with respect to this particular movement of the first mobile drive unit 20, as shown in FIG. 14.

If, instead, the first mobile drive unit 20 determines that the detected object is a second mobile drive unit 20 moving in the first direction, the first mobile drive unit 20 continues moving in the first direction. Additionally, in particular embodiments, the second mobile drive unit 20 may communicate information regarding its current state to the first mobile drive unit 20. For example, in particular embodiments, the drive identification signal 430 transmitted by the second mobile drive unit 20 may include information specifying the current speed of the second mobile drive unit 20, its position, and the maximum rate of deceleration it can presently achieve. At step 712, the first mobile drive unit 20 may then calculate a speed at which it can safely follow the second mobile drive unit 20. In particular embodiments, first mobile drive unit 20 may calculate this speed based on the state of first mobile drive unit 20 and/or the state of second mobile drive unit 20, as described above. At step 714, the first mobile drive unit 20 may continue movement in the first direction at the calculated speed. Operation may then end with respect to this particular movement of the first mobile drive unit 20, as shown in FIG. 14.

Figure 15:
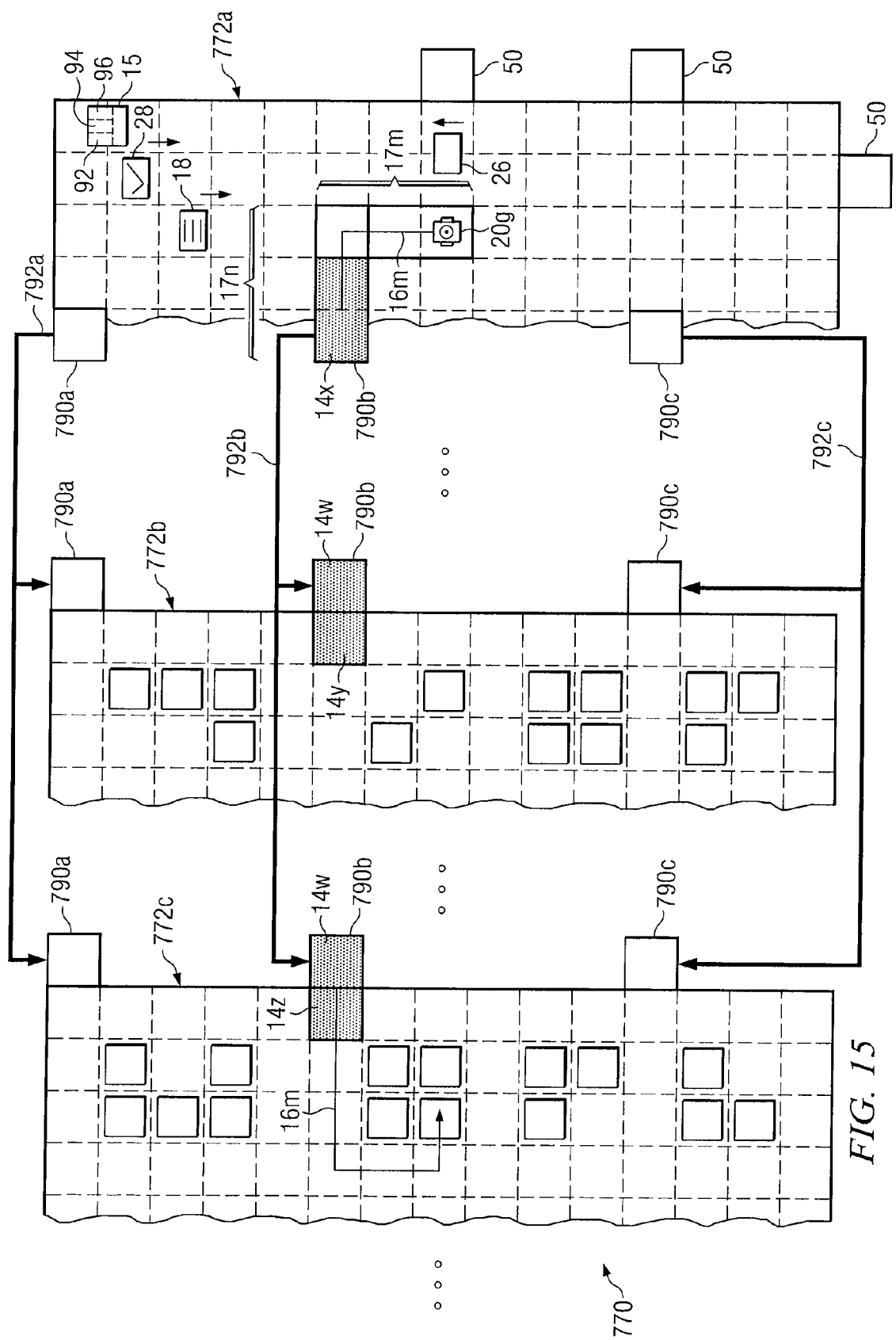
FIG. 15 illustrates an example embodiment of the inventory system that includes conveyance equipment capable of transporting mobile drive units between separate portions of the workspace.
Figure 16:
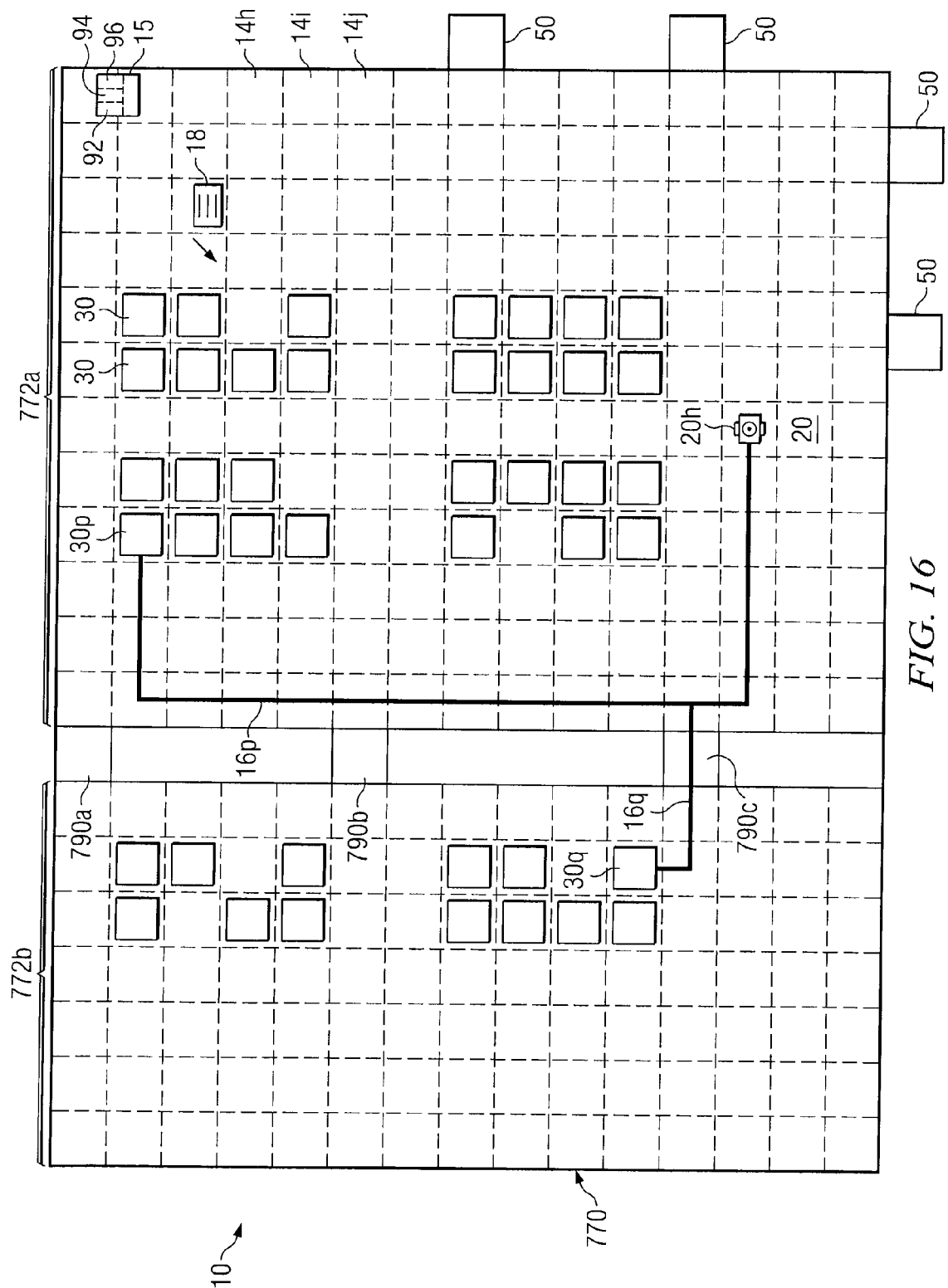
FIG. 16 illustrates techniques that the inventory system may use in assigning tasks based on the availability and characteristics of conveyance equipment.
Figure 17:
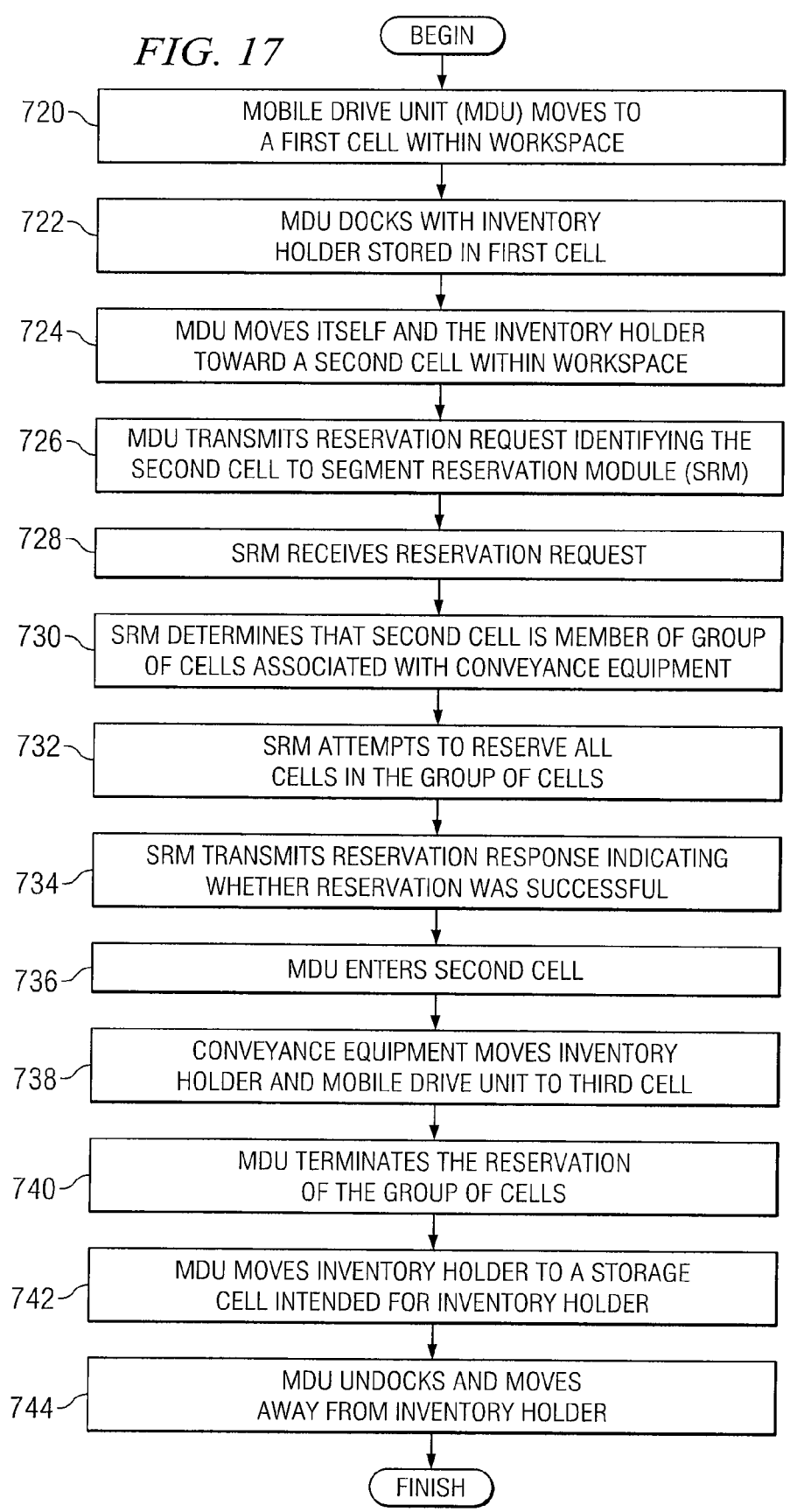
FIG. 17 is a flowchart illustrating the operation of a particular embodiment of resource scheduling module in selecting paths for mobile drive units in a workspace that utilizes drive lifts.

FIGS. 15 and 16 illustrate operation of a particular embodiment of route planning module 94 in utilizing various types of equipment in inventory system 10 to facilitate the movement of mobile drive units 20. More specifically, FIG. 15 illustrates a particular embodiment of inventory system 10 that includes conveyance equipment to supplement the capabilities of mobile drive units 20 in transporting inventory holders 30, while FIG. 16 illustrates an example of how route planning module 94 may plan paths for mobile drive units 20 that rely on such equipment. Additionally, FIG. 17 is a flowchart illustrating example operation of inventory system 10 in utilizing particular types of conveyance equipment to transport inventory holders 30.

FIG. 15 illustrates an embodiment of inventory system 10 that includes certain types of conveyance equipment that route planning module 94 may incorporate into paths 16 that route planning module 94 generates for requesting mobile drive units 20. In general, inventory system 10 may include any appropriate form of conveyance equipment to supplement the transportation capabilities provided by mobile drive units 20. Such conveyance equipment may include, but is not limited to, vertical lifts, horizontal conveyors, elevators, escalators, trucks, ferries, and/or any other equipment capable of transporting inventory holders 30 and/or mobile drive unit 20 that are themselves transporting inventory holders 30. As a result, particular embodiments of inventory system 10 that include such conveyance equipment may be capable of providing alternative manners of conveyance unachievable by the particular type of mobile drive unit 20 utilized in that embodiment of inventory system 10 (e.g., transportation between floors of a multi-floored workspace 70 or transportation between buildings in a multi-building workspace 70) or may be capable of more efficiently providing transportation of inventory holders 30 under certain conditions (e.g., scheduled transportation of groups of inventory holders 30 along high-traffic paths 16 or segments 17).

To optimize use of such conveyance equipment, management module 15 may implement certain techniques for path planning, segment reservation, and/or other aspects of managing inventory system 10 that consider the characteristics, advantages, and/or limitations of the conveyance equipment included in that particular embodiment of inventory system 10. FIG. 15 illustrates one example of techniques management module 15 may utilize to reserve access to and use of particular types of conveyance equipment for requesting mobile drive units 20. More specifically, FIG. 15 illustrates an example of how management module 15 handles reservation of drive lifts 790 in a multi-storied workspace 70 to facilitate entry to, use of, and exit from drive lifts 790 by mobile drive units 20.

Particular embodiments of inventory system 10, such as the one shown in FIG. 15, may utilize a workspace 770 that is spread over multiple different floors, rooms, and/or areas of a building or other structure that are otherwise physically separated from one another. In such embodiments, inventory holders 30, inventory stations 50, and/or other elements of inventory system 10 may be spread over multiple different floors, rooms, and/or areas, and mobile drive units 20 may move between these separate portions of workspace 770 to complete assigned tasks. Moreover, such embodiments may include alternative conveyance equipment to supplement the transportation capabilities of mobile drive units 20 in moving inventory holders 30 between the various portions of workspace 770. For example, FIG. 15 illustrates an inventory system 10 that includes drive lifts 790a-c to facilitate the movement of mobile drive units 20 and inventory holders 30 between the various floors 772 of workspace 770. As a result, resource scheduling module 92, route planning module 94, and/or other components of management module 15 may consider the multi-floor nature of workspace 770 and the existence of drive lifts 790 when assigning tasks to mobile drive units 20, planning paths to facilitate the completion of certain tasks, or performing any other task relating to the management of inventory system 10.

In the illustrated embodiment, inventory system 10 utilizes a plurality of drive lifts 790 that connect floors 772a-c of a multi-floor workspace 770. Drive lifts 790a-c each connect a ground floor 772a to a second-level floor 772b and a third-level floor 772c, as indicated by arrows 792a-c, respectively. Route planning module 94 is capable of generating paths 16 for mobile drive units 20 that rely on drive lifts 790 to facilitate the movement of mobile drive units 20 between different floors 772 of workspace 770. In particular embodiments, mobile drive units 20 may then traverse these paths 16, as described above with respect to FIG. 5, additionally reserving and using drive lifts 790 as appropriate to complete the received paths 16.

For the purposes of the illustrated example, mobile drive unit 20g is located on floor 772a and is assumed to have received a path 16m to a destination cell 14 located on floor 772c. Path 16m is assumed to utilize drive lift 790b to transport mobile drive unit 20g to floor 772c. After receiving path 16m, mobile drive unit 20 may begin advancing along the received path 16m, reserving segments and moving as described above with respect to FIG. 5. At an appropriate point along path 16m, for example while traversing segment 17m, mobile drive unit 20 may attempt to reserve a segment 17n associated with drive lift 790b.

Because the use of drive lifts 790 may require that certain conditions be satisfied to ensure that mobile drive units 20 are capable of safely entering and exiting drive lifts 790, segment reservation module 96 may be configured to consider the fact that a particular requested cell 14 or segment 17 is adjacent to or associated with a drive lift 790 when resolving reservations of that cell 14 or segment 17. As one example, in particular embodiments, resource scheduling module 92 may group cells 14 adjacent to a particular drive lift 790 on the various floors 772 of workspace 770 into a single group. In such embodiments, resource scheduling module 92 may grant use of the cells 14 and the associated drive lift 790 to a single mobile drive unit 20 at a time. As a result, resource scheduling module 92 may be able to ensure that a particular requesting mobile drive unit 20, after reserving a particular drive lift 790, is able to exit drive lift 790 on any floor 772 without the possibility of another mobile drive unit 20 blocking the requesting mobile drive unit 20 from exiting the relevant drive lift 790, either physically or by reserving a cell 14 the requesting mobile drive unit 20 must use to exit the relevant drive lift 790.

Thus, in the illustrated example, cells 14w, 14x, 14y, and 14z (the shaded cells 14 in FIG. 15) are all considered part of a cell group that is associated with drive lift 790b. As mobile drive unit 20g approaches drive lift 790b while traversing path 16m, mobile drive unit 20g attempts to reserve cell 14x by transmitting a reservation request 26 that identifies segment 17n. Segment reservation module 96 receives the reservation request 26 and determines that segment 17n includes a cell 14w that contains drive lift 790b. As a result, segment reservation module 96 attempts to satisfy the reservation request 26 by reserving all of the cells 14 in the group associated with drive lift 790b. More specifically, segment reservation module 96 attempts to reserve cells 14x, 14y, and 14z, as well as the requested cell 14w. In this embodiment, if segment reservation module 96 determines that mobile drive unit 20g cannot reserve all of cells 14w-14z then segment reservation module 96 transmits a reservation response 28 indicating that the requested reservation response 28 was unsuccessful. Mobile drive unit 20 may then take any appropriate remedial actions as described above with respect to FIG. 5. If, instead, segment reservation module 96 determines that mobile drive unit 20g can reserve all of cells 14w-14z, then segment reservation module 96 transmits a reservation response 28 indicating that the requested reservation was successful.

Additionally, in particular embodiments, drive lift 790 may include only a single platform or car and a mobile drive unit's ability to access the drive lift 790 at a given time may depend on the floor 772 on which the car or platform is located at that time. Thus, as part of determining whether a requesting mobile drive unit 20 can reserve a particular drive lift 790, segment reservation module 96 may determine whether the platform or car is currently located on the same floor 772 as the requesting mobile drive unit 20. If not, segment reservation module 96 may, depending on the configuration of inventory system 10, decline the requested reservation, grant the requested reservation but indicate that mobile drive unit 20 must wait a particular amount of time before attempting to enter the relevant drive lift 790, or grant the requested reservation and rely upon interaction between the relevant drive lift 790 and the requesting mobile drive unit 20 (e.g., traffic signals transmitted by the drive lift 790) to ensure that the requesting mobile drive unit 20 waits until the drive lift 790 is appropriately positioned before entering.

Additionally, in particular embodiments, to improve the effectiveness of drive lifts 790, segment reservation module 96 may consider the current position of a car or platform of a particular drive lift 790 when deciding which of competing mobile drive units 20 to grant use of that drive lift 790. As an example, in particular embodiments, segment reservation module 96 may reduce movement of the car or platform while empty by granting mobile drive units 20 located on the current floor of the car or platform priority in reserving use of the car or platform. Thus, if two mobile drive units 20 both request use of the same drive lift 790 at approximately the same time, segment reservation module 96 may give priority to the reservation of the mobile drive unit 20 that is located on the same floor that the car or platform of the relevant drive lift 790

Returning to the example, drive lift 790b is appropriately configured for use by mobile drive unit 20g, mobile drive unit 20g may enter drive lift 790b. Drive lift 790b may then transport mobile drive unit 20g to floor 772c. Mobile drive unit 20g may then exit drive lift 790b into cell 14z, which, in this example, mobile drive unit 20g has already reserved by virtue of reserving cell 14w and/or use of drive lift 790b.

Additionally, in particular embodiments, mobile drive units 20 may be capable of receiving new tasks and/or paths 16 while being transported between floors 772. As a result, the fact that mobile drive units 20, when using a particular drive lift 790, reserve a group of cells 14 appropriate to allow exit and entry to that drive lift 790 on any floor 772 may, in particular embodiments, allow mobile drive unit 20 to adjust quickly to the new task or path 16 and exit the relevant drive lift 790 on a different floor 772 without being blocked by mobile drive units 20 on the new floor 772. For example, mobile drive unit 20g may receive a new task and/or path 16 requiring mobile drive unit 20 to exit drive lift 790 on floor 772b. As a result of the fact that mobile drive unit 20g previously reserved all of the cells 14 in the group associated with drive lift 790b, another mobile drive unit 20 will not be blocking cell 14y physically or by reservation, if mobile drive unit 20g attempts to change its path and exit on floor 772b. This, in turn, may prevent mobile drive unit 20g from monopolizing lift 772b despite its sudden change in route.

Returning to the illustrated example, once drive lift 790b transports mobile drive unit 20g to floor 772c, mobile drive unit 20g exits drive lift 790b. As noted above, in particular embodiments, mobile drive unit 20 has already reserved cell 14z as part of its initial reservation. In such embodiments, that reservation will ensure cell 14z is clear and mobile drive unit 20 can immediately disembark from drive lift 790. Mobile drive unit 20 may then proceed with completing the remainder of path 16m as described above with respect to FIG. 5.

By reserving an entrance and multiple possible exits from drive lifts 790 for mobile drive units 20 using those drive lifts 790, segment reservation module 96 may limit traffic congestion and reduce the amount of time mobile drive units 20 are forced to wait before exiting drive lifts 790. Additionally, this reservation system may prevent a blocked mobile drive unit 20 from delaying use of a drive lift 790 by other mobile drive units 20. Furthermore, by considering the current location of a car or lift of a drive lift 790 in granting reservations, segment reservation module 96 may limit the number of unloaded transitions the car or platform makes between floors 772 and increase the drive lifts 790 throughput. As a result, the described techniques may facilitate more efficient operation of drive lifts 790 and mobile drive units 20.

FIG. 16 illustrates further certain techniques that particular embodiments of inventory system 10 may implement to optimize the use of conveyance equipment, such as drive lifts 790, to supplement the operation of mobile drive units 20 in transporting inventory holders 30. More specifically, FIG. 16 illustrates certain techniques particular embodiments of inventory system 10 may utilize to ensure that the benefits and drawbacks of using a particular type conveyance are weighed in planning the tasks that will be assigned and the routes that mobile drive units 20 will take when moving within workspace 70. As a result, particular embodiments of inventory system 10 may further increase the efficiency that may result from the availability and use of conveyance equipment to assist mobile drive units 20 in transporting inventory holders 30.

For example, in particular multi-story embodiments of inventory system 10, resource scheduling module 92 may associate a cost with the use of each cell 14 in workspace 770.

This cost may represent the time expended in driving across the cell 14, the historical level of congestion within the cell 14 or neighboring cells 14, the number of inventory holders 30 adjacent to the cell, and/or any other consideration that may reflect the cost in time, space, and/or other resources that is associated with routing a mobile drive unit 20 through the relevant cell 14. Likewise, resource scheduling module 92 may associate a cost with the use of drive lifts 790 and/or other equipment used to facilitate movement of mobile drive units 20 such as conveyors, escalators, and/or cranes. Using drive lifts 790 as an example, this cost may represent the time expended in riding drive lift 790 between particular floors 772, the power expended in operating drive lift 790, the frequency with which multi-floor paths using that drive lift 790 are otherwise generated by resource scheduling module 92, and/or any other consideration that may reflect the cost in time, space, and/or other system resources that is associated with providing mobile drive unit 20 a path 16 that utilizes the relevant drive lift 790.

When management module 15 receives an inventory request identifying, for example, a particular inventory item 40 to be retrieved, resource scheduling module 92 may select an inventory holder 30 based, at least in part, on the least-costly route to each of the inventory holders 30 currently storing the requested inventory item 40. Consequently, in particular embodiments, resource scheduling module 92 may add up the total cost associated with every possible path 16 between the current location of the relevant mobile drive unit 20 and a particular inventory holder 30 storing the relevant inventory item 40. Resource scheduling module 92 may then compare the cost of the least expensive path between the mobile drive unit 20 and each inventory holder 30 and select an inventory holder 30 based, at least in part, on the least costly path 16 between a selected mobile drive unit 20 and each of the inventory holders 30.

To illustrate, FIG. 16 shows an example in which management module 15 selects an inventory holder 30 to be used in satisfying an inventory request requesting a particular inventory item 40. In the example, resource scheduling module 92 has already selected mobile drive unit 20h based on appropriate criteria to retrieve an inventory holder 30 containing the requested inventory item 40. Inventory holders 30p and 30q are the only inventory holders 30 currently storing the requested inventory item 40. Additionally, for the purposes of this example, it is assumed that path 16p and path 16q are the least costly paths 16 between mobile drive unit 20h and inventory holder 30p and 30q, respectively. As a result, resource scheduling module 92 selects one of inventory holder 30p and 30q based, at least in part, on the cost associated with path 16p and 16q.

Consequently, if the cost associated with path 16p is greater than the cost associated with path 16q, resource scheduling module 92 will select inventory holder 30q, and mobile drive unit 20h, in this example, will be required to use one of drive lifts 790 to access floor 772b when retrieving inventory holder 30q. If however, the cost associated with using drive lift 790 and traversing the cells 14 on path 16q exceed the cost of traversing cells 14 on path 16p, resource scheduling module 92 will select inventory holder 30p. Thus, resource scheduling module 92, in particular embodiments, is capable of recognizing that one or more costs of using drive lifts 790 may make the use of drive lifts 790 less preferred in many cases, but that, under certain circumstances, the benefits of using drive lifts 790 may outweigh these costs.

After selecting an inventory holder 30 to be retrieved, resource scheduling module 92 communicates the location of the selected inventory holder 30 to mobile drive unit 20h, for example, as part of a task assignment 18, as described above. Assuming, for the purpose of this example, that resource scheduling module 92 has selected inventory holder 30q, mobile drive unit 20h requests a path 16 to inventory holder 30q from route planning module 94. In response, route planning module 94 communicates path 16q or, if routing considerations have changed since inventory holder 30q was selected, another path 16 to inventory holder 30q.

Upon receiving a suitable path 16 to inventory holder 30q, mobile drive unit 20h reserves a first segment 17 of the received path 16 and begins moving towards inventory holder 30q as described above with respect to FIG. 5. Assuming mobile drive unit 20h received path 16q from route planning module 94, mobile drive unit 20h will move towards drive lift 790c along path 16q. As mobile drive unit 20h approaches drive lift 790c, mobile drive unit 20h may attempt to reserve drive lift 790c. In particular embodiments, mobile drive unit 20h may reserve drive lift 790c in a similar manner as that described above for reserving segments 17. Thus, if another mobile drive unit 20h currently has drive lift 790c reserved and/or is currently on drive lift 790c, mobile drive unit 20h may be unable to reserve drive lift 790c.

Once mobile drive unit 20h does successfully reserve drive lift 790c, mobile drive unit 20h may position itself on drive lift 790c. Drive lift 790c may then lift mobile drive unit 20h to floor 772b. As noted above, operation of drive lifts 790 may be controlled by mobile drive units 20, management module 15, or any other suitable components of inventory system 10. After drive lift 790c lifts mobile drive unit 20h to floor 772, mobile drive unit 20h proceeds to the location of inventory holder 30q and docks with inventory holder 30q. Mobile drive unit 20h may then request, from route planning module 94, a path 16 back to an inventory station 50 associated with the inventory request. After receiving such a path 16, mobile drive unit 20h may use a drive lift 790 specified by the received path 16 to return to floor 772a and then move inventory holder 30q to the relevant inventory station 50 to complete the assigned task.

As a result, inventory system 10 may incorporate drive lifts 790 to lift and lower mobile drive units 20 thereby facilitating the use of multi-storied workspaces 770. Moreover, management module 15 and its various components may be configured to consider the costs and benefits of using drive lifts 790 and may, as a result, make knowledgeable decisions regarding the use of drive lifts 790 to complete particular tasks. In a similar manner, inventory system 10 and management module 15 may be configured to utilize other equipment (such as, for example, conveyors, escalators, cranes, or ferries) or features (such as, for example, ramps, tunnels, or stairways) to facilitate the movement of mobile drive units 20 within workspace 770. Additionally, the ability to effectively incorporate such equipment into inventory system 10 may allow greater flexibility in the size, shape, and configuration of workspace 770 and/or provide other benefits.

FIG. 17 is a flowchart illustrating the operation of a particular embodiment of resource scheduling module 92 in selecting paths for mobile drive units 20 in a workspace 70 that utilizes conveyance equipment in conjunction with mobile drive units 20 to transport inventory holders 30. While FIG. 17 focuses on a particular embodiment of inventory system 10 that utilizes a particular technique for reserving conveyance equipment, alternative embodiments of inventory system 10 may be configured to utilize conveyance equipment in any appropriate manner. Additionally, any of the steps illustrated in FIG. 17 may be combined, modified, or deleted where appropriate, and additional steps may also be added to those shown in the flowchart. Moreover, the described steps may be performed in any suitable order without departing from the scope of the invention.

Operation begins, in FIG. 17, with a mobile drive unit 20 moving to a first point within a workspace 70 at step 720. In the described example, an inventory holder 30 is stored in a first cell 14 at the first point. After arriving at the first point, mobile drive unit 20 docks with the inventory holder 30 stored at the first point at step 722.

After docking with inventory holder 30, mobile drive unit 20 moves itself and the inventory holder toward a second point within the workspace at step 724. In the illustrated example, the second point is located in a second cell 14 that is associated with conveyance equipment. This second cell 14 may represent a cell in which the conveyance equipment is located, an entry cell for the conveyance equipment, a pick-up cell for the conveyance equipment, or a cell associated with the conveyance equipment in any other manner. Additionally, in the described example, the conveyance equipment is associated with a group of multiple cells 14 of which the second cell 14 is a member.

As mobile drive unit 20 moves to the second point, or once mobile drive unit 20 arrives at the second point, mobile drive unit 20 reserves the second cell 14. In the described example, mobile drive unit 20 reserves the second cell 14 by transmitting a reservation request 26 identifying the second cell 14 to segment reservation module 96 15 at step 726. At step 728, segment reservation module 96 receives reservation request 26.

After receiving reservation request 26, segment reservation module 96 determines that the second cell 14 is a member of a group of cells 14 that are associated with the conveyance equipment at step 730. As a result, segment reservation module 96, as a response to receiving reservation request 26, attempts to reserve all of the cells 14 in the group of cells 14 associated with the conveyance equipment at step 732. Segment reservation module 96 then indicates to the requesting mobile drive unit 20 whether segment reservation module 96 was able to reserve the second cell and/or all of the cells 14 in the group associated with the conveyance equipment. In the described example, segment reservation module 96 communicates the outcome to mobile drive unit 20 by transmitting a reservation response 28 at step 734.

After successfully reserving the group of cells 14 associated with the conveyance equipment, mobile drive unit 20 enters the second cell 14 at step 736. At step 738, in the described example, the conveyance equipment moves inventory holder 30 and mobile drive unit 20 to a third point. In alternative embodiments, the conveyance equipment may move inventory holder 30 without moving mobile drive unit 20 and mobile drive unit 20 may undock from the inventory holder 30 at the second point.

After the conveyance equipment moves the inventory holder 30 and, if appropriate, mobile drive unit 20 to the third point, mobile drive unit 20 or another suitable component of inventory system 10 terminates the reservation of the group of cells 14 associated with the conveyance equipment at step 740. In particular embodiments, the group of cells 14 may include, at or near the third point, one or more exit cells 14, drop-off cells 14, and/or other appropriate cells 14 that are part of the group of cells 14 associated with the conveyance equipment and the reservation may be maintained until mobile drive unit 20 exits those cells 14.

At step 742, the original mobile drive unit 20 or another mobile drive unit 20 moves inventory holder 30 to a fourth point. The fourth point may represent a storage location, inventory station 50, or other appropriate destination associated with the relevant inventory holder 30. For example, in the described example, the fourth point is located in a storage cell 64 intended for inventory holder 30. Thus, in this example, mobile drive unit 20 undocks from inventory holder 30 and moves away from inventory holder 30 at step 744. In this example, operation of inventory system 10 with respect to moving inventory holder 30 then ends as shown in FIG. 17.

Figure 18:
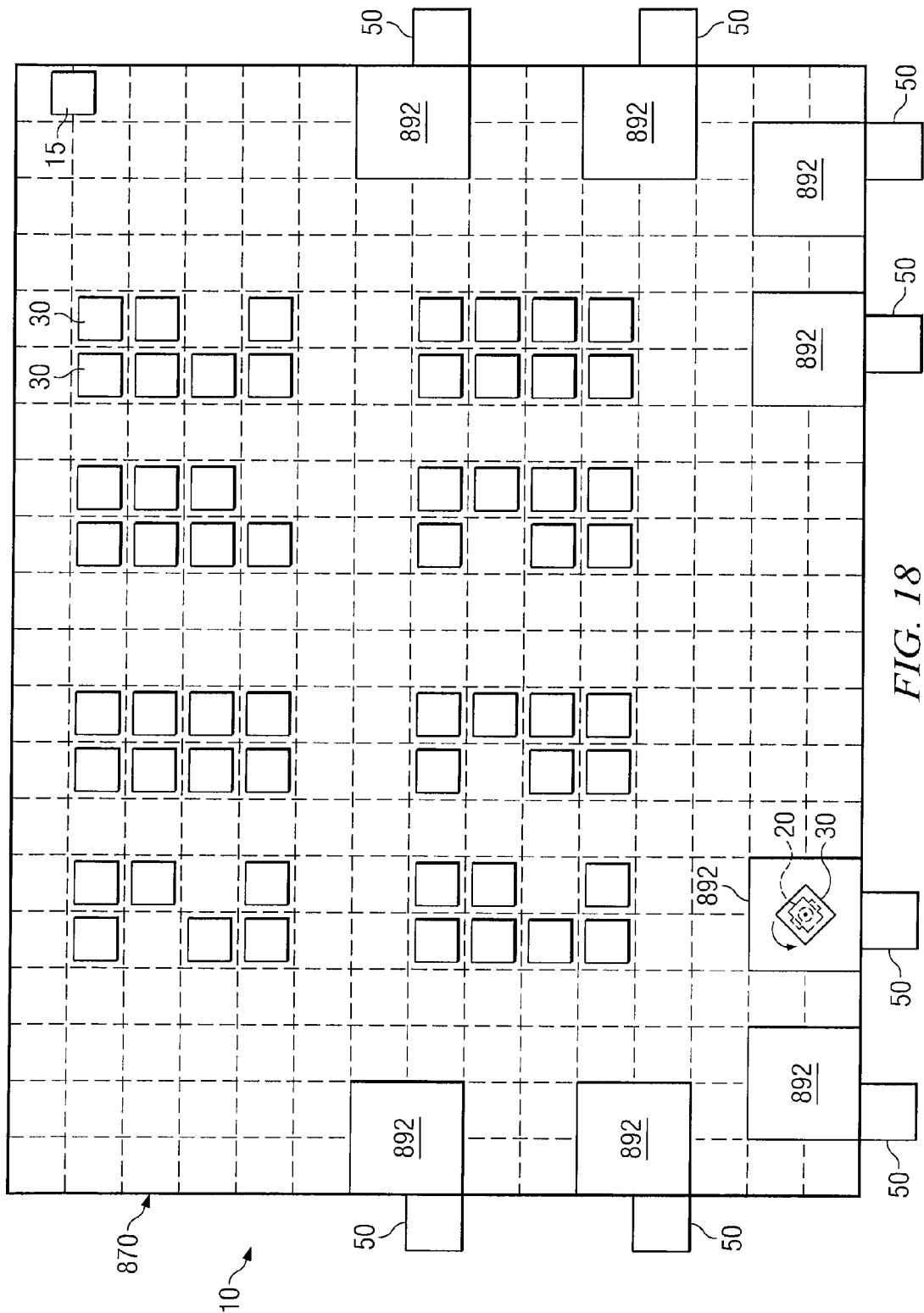
FIG. 18 illustrates an example embodiment of the inventory system that includes one or more rotation areas for the rotation of inventory holders.

FIGS. 18-20 illustrate example operation of an embodiment of inventory system 10 that utilizes specific techniques for rotating inventory holders 30 as part of transporting inventory holders 30 within inventory system 10. These techniques may be useful, for example, in presenting a particular face of an inventory holder 30 to an operator of an inventory station 50. The described techniques and system configuration may allow particular embodiments of inventory system 10 to operate within workspaces 70 having a reduced size and to simplify the coordination of mobile drive unit movement. In particular embodiments of inventory system 10 that utilize inventory stations 50, the positioning of rotation areas 790 near inventory stations 50 may allow management module 15 to delay the selection of a face to be presented at a particular inventory station 50 until the assigned mobile drive unit 20 is near the inventory station 50. This may allow management module 15 to optimize face selection based on the current state of inventory system 10.

FIG. 18 illustrates an embodiment of inventory system 10 that includes a management module 15, one or more mobile drive units 20, one or more inventory holders 30, and one or more inventory stations 50 that operate within a workspace 870 similar to those described above with respect to FIG. 1. Additionally, workspace 870 includes a plurality of rotation areas 892 in which mobile drive units 20 perform particular operations associated with rotating inventory holders 30. By performing some or all rotations of inventory holders 30 in rotation areas 892, particular embodiments of inventory system 10 may be configured to operate within a smaller workspace.

Rotation areas 892 represent a portion of workspace 870 covering a plurality of cells 14. In particular embodiments of inventory system 10, the number and arrangement of cells 14 in a particular rotation area 892 are selected based on the size and shape of inventory holders 30 and the type of rotational movement supported by mobile drive units 20. For example, in particular embodiments, inventory system 10 utilizes inventory holders 30 that include four similarly-dimensioned faces with each face having a width substantially equal to or slightly smaller than the width of a cell 14 in workspace 870. Particular embodiments may also utilize mobile drive units 20 that are capable of three-hundred and sixty degree rotations while stationary. In such embodiments, workspace 870 may include rotation areas 892 that represent a two-cell by two-cell section of workspace 870. While FIG. 18 illustrates a particular embodiment in which rotation areas are equal in size to some whole multiple of the size of an individual cell 14, alternative embodiments of inventory system 10 may utilize rotation areas 892 having any suitable size that is larger than the size of an individual cell 14. Additionally, although FIG. 18 illustrates a particular embodiment of inventory system 10 in which rotation areas 892 are located adjacent to each inventory station 50, alternative embodiments of inventory items 40 may include any number of rotation areas 892 in any appropriate location within workspace 870.

In the illustrated embodiment of inventory system 10, mobile drive units 20 interact with management module 15 to receive task assignments, request paths 16, and reserve routed segments 17 in order to complete tasks in a manner similar to that described above with respect to FIG. 5. While transporting inventory holders 30 between locations in workspace 870, a mobile drive unit 20 maintains a constant orientation for inventory holders 30 regardless of the direction mobile drive unit 20. Consequently, in the illustrated embodiment, when a mobile drive unit 20 changes the direction in which it is traveling, the orientation of an inventory holder 30 being transported by that mobile drive unit 20 remains the same despite the direction change.

This may be accomplished in a variety of ways depending on the configuration and capabilities of mobile drive units 20. As one example, in particular embodiments, a mobile drive unit 20 may be capable of propelling itself in a forward and a backward direction relative to a certain face of mobile drive unit 20 and of rotating itself to change its direction of travel. In such embodiments, mobile drive unit 20 may undock from an inventory holder 30 it is currently transporting before rotating and inventory holder 30 may, as a result, maintain a constant orientation regardless of the direction in which mobile drive unit 20 is driving. As another example, in particular embodiments, mobile drive unit 20 is capable of propelling itself in any of four directions and can thus change its direction of travel without rotating.

Because many shapes of inventory holders 30 require a greater amount of space between neighboring inventory holders 30 when one or more such inventory holders 30 are rotated, limiting rotation of inventory holders 30 can reduce the amount of space required for inventory holders 30 to be transported within workspace 870 without collisions occurring between inventory holders 30. Nonetheless, in particular embodiments of inventory system 10, a number of benefits may arise from mobile drive units 20 rotating inventory holders 30. For example, inventory system 10 may reduce the amount of time and effort that is spent by the operator of an inventory station 50 in retrieving inventory items 40 from a particular bin of an inventory holder 30 if inventory holder 30 is rotated so that the appropriate face of that inventory holder 30 is presented to the operator.

Thus, in the illustrated embodiment of inventory system 10, mobile drive units 20 may be configured to allow rotation of inventory holders 30 but to perform some or all such rotations in rotation areas 892. In particular, mobile drive units 20 assigned tasks that involve transporting inventory holders 30 to inventory stations 50 may bring inventory holders 30 towards inventory station 50, maintaining a constant orientation for inventory holders 30 as described above. Mobile drive units 20 may then, if appropriate, execute one or more steps designed to induce a certain form of rotation in inventory holder 30 suitable to present a particular face of the retrieved inventory holder 30 to inventory station 50. FIGS. 19A to 19E illustrate examples of the steps particular embodiments of mobile drive units 20 may execute to induce specific types of rotation in inventory holders 30. After completing the appropriate form of rotation, mobile drive unit 20 may then position inventory holder 30 in front of inventory station 50 to allow an operator of inventory station 50 to access the presented face of inventory holder 30.

Consequently, by restricting or eliminating the ability of mobile drive units 20 to rotate inventory holders 30 outside of rotation areas 892, particular embodiments of inventory system 10 may be able to utilize smaller cells 14 without collisions occurring. As a result, such embodiments may be able to operate within a smaller workspace. Thus, by incorporating rotation areas 892, particular embodiments of inventory system 10 may reduce their overall space requirements and/or provide additional operational benefits.

Figure 19D:
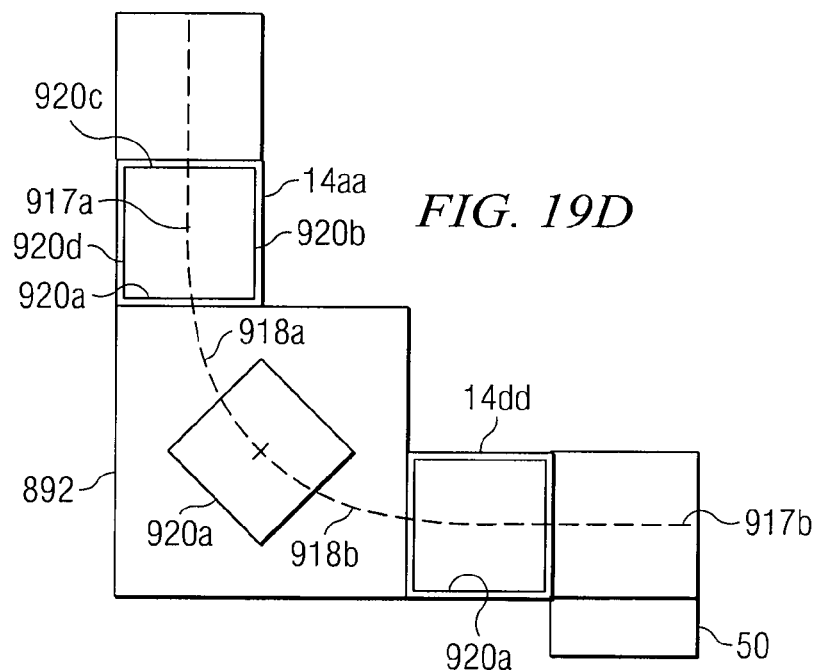
Figure 19E:
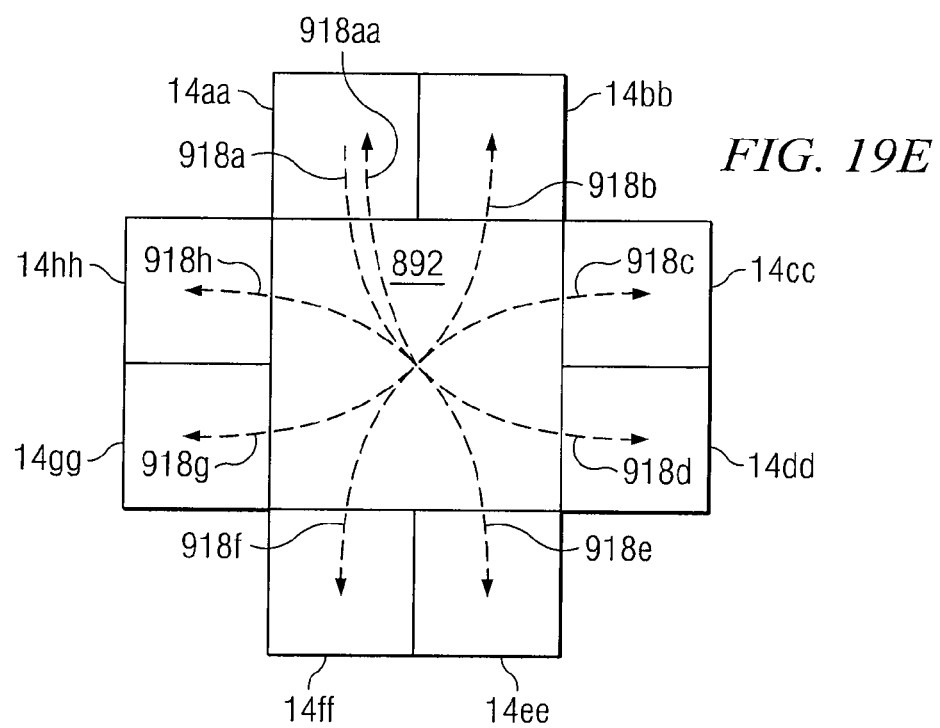

FIGS. 19A-19E illustrate example maneuvers that may be performed by particular embodiments of mobile drive unit 20 when rotating an inventory holder 30 in a rotation area 892. In particular, FIGS. 19A-19D illustrate various maneuvers that may be completed by mobile drive unit 20 to enter a rotation area 892 from a first cell 14 and exit the rotation area 892 into a second cell 14 while rotating inventory holder 30 so that a particular one of the four faces of inventory holder 30z is presented to inventory station 50. FIG. 19E illustrates various maneuvers that may be performed by mobile drive unit 20z to allow mobile drive unit 20z to exit rotation area 892 into any cell 14 neighboring rotation area 892. Thus, as shown by FIGS. 19A-19E, in particular embodiments, mobile drive unit 20 may enter a rotation area 892 from any neighboring cell 14, perform an appropriate rotation so that any face of inventory holder 30 is facing a specific direction, and then exit into any specific cell 14 neighboring rotation area 892.

FIG. 19A illustrates an example in which mobile drive unit 20 enters rotation area 892 from cell 14aa, rotates, and exits rotation area 892 into cell 14dd. In particular embodiments, rotation areas 892 may be associated with a queue in which mobile drive units 20 are expected to wait until being granted access to rotation area 892 and also with an inventory station 50 at which the relevant inventory holder 30 will be presented after exiting the relevant rotation area 892. As a result, mobile drive units 20 may be limited in terms of the cells 14 from which they can enter rotation areas 892 and limited in terms of the cell 14 into which they can exit rotation areas 892. Thus, FIGS. 19A-19D illustrate an example of such an embodiment in which mobile drive unit 20z is limited to entering rotation area 892 from cell 14aa and exiting rotation area 892 into cell 14dd.

More specifically, in the example shown in FIG. 19A, mobile drive unit 20 receives a path 16 into rotation area 892 through cell 14aa. Mobile drive unit 20 approaches cell 14aa along a straight segment 917a with a first face of inventory holder 30 (labeled as face "920a" in FIG. 19A) facing in the direction of travel, referred to here as the "first" direction. As mobile drive unit 20 is traveling through cell 14aa, mobile drive unit 20 begins to veer to the left or right so that mobile drive unit 20 follows an arced segment 918a into rotation area 892. While mobile drive unit 20 follows arced segment 918a, the orientation of first face is kept consistent with the direction of travel, as shown in FIG. 19A. As a result, when mobile drive unit 20 reaches the center of rotation area 892, in the illustrated example, the orientation of the first face has changed so that the first face now faces a direction ("referred to here as the "second" direction) somewhere between the first direction and a third direction orthogonal to the first direction. In particular embodiments, this second direction equals approximately a forty-five degree rotation from the first direction.

Upon reaching the center of rotation area 892, mobile drive unit 20 may perform any of a number of rotation maneuvers to facilitate the presentation of a particular face of inventory holder 30. FIGS. 19A-19D illustrate examples of these rotation maneuvers. In particular, FIG. 19A illustrates an example in which mobile drive unit 20 performs a ninety degree rotation (as indicated by arrow 901a) in the direction opposite of the veer mobile drive unit 20 executed to follow arced segment 918b to orient inventory holder 30 so the first face is presented to an operator of inventory station 50. Mobile drive unit 20 then moves toward the cell 14dd along arced segment 918b veering in the same direction as the original veer. As a result of the ninety-degree rotation, a second face (labeled as face "920b" in FIG. 19A) of inventory holder 30 now faces in the direction of travel and mobile drive unit 20 holds the orientation of this second face consistent with the direction of travel as mobile drive unit 20 follows arced segment 918b.

Furthermore, as mobile drive unit 20 travels arced segment 918*b* this arced path induces an additional rotation in inventory holder 30 that complements the rotation induced in inventory holder 30 while mobile drive unit 20 traveled arced segment 17*a*. In particular embodiments, this rotation is equal to approximately forty-five degrees. As a result, the total rotation induced in inventory holder 30 as a result of mobile drive unit 20 traveling the arced segments 918*a* and 918*b* is approximately ninety degrees. In FIG. 19A, this rotation counteracts the rotation performed by mobile drive unit 20 at the center of rotation area 892 and, as mobile drive unit 20 completes arced segment 918*b*, the first face of inventory holder 30 is once again facing the first direction. Mobile drive unit 20 may then follow another straight path segment 17 to inventory station 50. As a result, in FIG. 19A, the first face of inventory holder 30 is presented to the operator of inventory station 50.

FIG. 19B illustrates a similar example in which the second face is presented to the operator of inventory station 50. More specifically, in FIG. 19B, mobile drive unit 20 follows straight path segment 17*a* into cell 14*a* and follows arced segment 918*a* into rotation area 892, as described with respect to FIG. 19A. Upon reaching the center of rotation area 892, however, mobile drive unit 20 performs a one-hundred-and-eighty-degree rotation (as indicated by arrow 901*b*). Mobile drive unit 20 then follows arced segment 918*b* into cell 14*dd*. As a result of the rotation performed at the center of rotation area 892, a third face of inventory holder 30 (labeled as face "920*c*" in FIG. 19B) now faces in the direction of travel and mobile drive unit 20 holds the orientation of this third face consistent with the direction of travel as mobile drive unit 20 follows arced segment 17*b*.

As mobile drive unit 20 travels arced segment 918*b* the arced path induces an additional rotation in inventory holder 30 as described with respect to FIG. 19A. In FIG. 19B, this rotation partially counteracts the rotation performed by mobile drive unit 20 at the center of rotation area 892 and, as mobile drive unit 20 completes arced segment 17*b*, the second face of inventory holder 30 is now facing the first direction. Mobile drive unit 20 may then follow straight segment 917*b* to inventory station 50. As a result, in FIG. 19B, the second face of inventory holder 30 is presented to the operation of inventory station 50.

FIG. 19C similarly illustrates an example in which the third side is presented to the operator of inventory station 50. More specifically, in FIG. 19C, mobile drive unit 20 follows straight path segment 917*a* into cell 14*aa* and follows arced segment 918*a* into rotation area 892, as described with respect to FIGS. 19A and 19B. Upon reaching the center of rotation area 892, however, mobile drive unit 20 performs a two-hundred-and-seventy-degree rotation. Mobile drive unit 20 then follows arced segment 918*b* into cell 14*dd*. As a result of the rotation performed at the center of rotation area 892, a fourth face of inventory holder 30 (labeled as face "920*e*" in FIG. 19C) now faces in the direction of travel and mobile drive unit 20 holds the orientation of this fourth face consistent with the direction of travel as mobile drive unit 20 follows arced segment 918*b*.

As mobile drive unit 20 travels arced segment 918*b* the arced path induces an additional rotation in inventory holder 30 as described with respect to FIGS. 19A and 19B. In FIG. 19C, this rotation partially counteracts the rotation performed by mobile drive unit 20 at the center of rotation area 892 and, as mobile drive unit 20 completes arced segment 918*b*, the third face of inventory holder 30 is now facing the first direction. Mobile drive unit 20 may then follow straight path segment 918*b* to inventory station 50. As a result, in FIG. 19C, the third face of inventory holder 30 is presented to the operator of inventory station 50.

FIG. 19D illustrates an example in which the fourth side is presented to the operator of inventory station 50. More specifically, in FIG. 19D, mobile drive unit 20 follows straight path segment 917*a* into cell 14*aa* and follows arced segment 918*a* into rotation area 892, as described with respect to FIGS. 19A and 19B. Upon reaching the center of rotation area 892, however, mobile drive unit 20 performs no rotation in the example illustrated by FIG. 19D. Mobile drive unit 20 follows arced path 918*b* into cell 14*dd*. Because no rotation was performed at the center of rotation area 892, the first face of inventory holder 30 remains facing in the direction of travel, and mobile drive unit 20 holds the orientation of the first face consistent with the direction of travel as mobile drive unit 20 follows arced segment 918*b*.

As mobile drive unit 20 travels arced segment 918*b* the arced path induces an additional rotation in inventory holder 30 as described with respect to FIGS. 19A-19C. Consequently, as mobile drive unit 20 completes arced segment 918*b*, the fourth face of inventory holder 30 now faces the first direction. Mobile drive unit 20 may then follow straight path segment 917*b* to inventory station 50. As a result, in FIG. 19D, the fourth face of inventory holder 30 is presented to the operator of inventory station 50.

Thus, by performing a selected rotation maneuver (including, in particular circumstances, no rotation) within rotation area 892, particular embodiments of mobile drive unit 20 are capable of achieving any desired orientation for inventory holder 30 upon arriving at inventory station 50. Moreover, when utilized in embodiments of inventory system 10 that limit or prohibit rotations elsewhere in workspace 870, the inclusion of rotation areas 892 in select places within workspace 870 allows inventory system 10 to support the presentation of any face of inventory holders 30 within a significantly smaller workspace. As a result, the use of the described rotation maneuvers may provide space-saving and other advantages.

FIG. 19E illustrates how, in particular embodiments, mobile drive units 20 can be configured to access rotation areas 892 using any appropriate combination of neighboring cells 14 as entry and exit points. As shown in FIG. 19E, mobile drive unit 20 may be configured to follow arced segment 918*a* into rotation area 892, perform an appropriate rotation maneuver, and then follow one of arced segment 918*b*, arced segment 918*c*, arced segment 918*d*, arced segment 918*e*, arced segment 918*f*, arced segment 918*g*, and arced segment 918*h* to exit into cell 14*bb*, cell 14*cc*, cell 14*dd*, cell 14*ee*, cell 14*ff*, cell 14*gg*, and cell 14*hh*, respectively. Additionally, mobile drive unit 20 may be configured to exit rotation area 892 following the same path mobile drive unit 20 followed entering rotation area 892, that is arced segment 918*a*. This is indicated in FIG. 19E by the dotted-line curve labeled 918*aa*.

Furthermore, while FIG. 19E illustrates an example in which mobile drive unit 20 is configured to enter rotation area 892 through a particular cell 14, specifically cell 14*aa*, the example arced segment 918*a* in FIG. 19E can be generalized to represent an arced segment 918 entering rotation area 892 from any of neighboring cells 14*aa*-*dd*. As a result, in a given embodiment of inventory system 10, mobile drive units 20 may be configured to enter rotation area 892 from and exit rotation area 892 to any appropriate cell 14 neighboring rotation area 892. On the other hand, a given embodiment of inventory system 10 that utilizes rotation areas 892 may also limit the cells 14 that may be used enter and exit a particular rotation area 892, for example, to control traffic flow around rotation area 892. Thus, while a particular embodiment of inventory system 10 may include a rotation area 892 that mobile drive units 20 are capable of utilizing without constraints as to their entry and exit points, the same or other embodiments of inventory system 10 may include rotation areas 892 that mobile drive units 20 are configured to enter or exit using specific neighboring cells 14.

Thus, in particular embodiments, to present a desired face in a desired direction and to provide flexibility in choosing entry points into and exit points out of rotation areas 892, mobile drive units 20 may enter rotation areas 892 then perform one or both of a rotation that rotates both mobile drive unit 20 and inventory holder 30 and a rotation that rotates only mobile drive unit 20, in any appropriate order. This may result in both mobile drive unit 20 having the appropriate orientation for mobile drive unit 20 to utilize the desired exit point from the rotation area 892 and inventory holder 30 having the appropriate orientation to present the desired face in the desired direction after mobile drive unit 20 and inventory holder 30 exit rotation area 892. As a result, in particular embodiments, mobile drive unit 20 may be able to utilize any desired entry and exit points to rotation area 892 and be able to present any desired face of inventory holder 30 in any desired direction.

FIGS. 20A-20G illustrate an example of how mobile drive unit 20 may traverse the portions of workspace 870 outside designated rotation areas 892 without rotating inventory holders 30. In particular, FIGS. 20A-20G show operation of a mobile drive unit 20 as the mobile drive unit 20 moves inventory holder 30 from a first position to a second position along a portion of a path 16 that includes a ninety-degree turn. Because, in the illustrated embodiment, mobile drive unit 20 is able to turn a corner without rotating inventory holder 30, inventory holder 30 may not overlap neighboring cells 14 and/or interfere with inventory holders 30 in neighboring cells 14 when mobile drive unit 20 changes its direction of travel. As a result, inventory system 10 may operate with a smaller workspace and thus mobile drive units 20 configured to operate as shown in FIGS. 20A-20G may provide space-saving benefits.

Figure 20A:
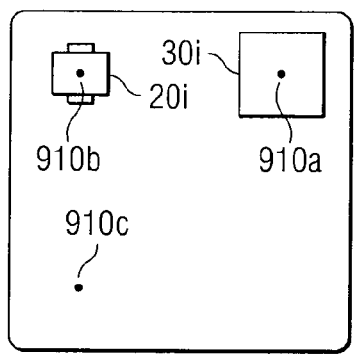
FIGS. 20A-20F illustrate example operation of a particular embodiment of mobile drive unit while transporting inventory holders outside of the rotation areas illustrated in FIGS. 18 and 19A-19E.
Figure 20B:
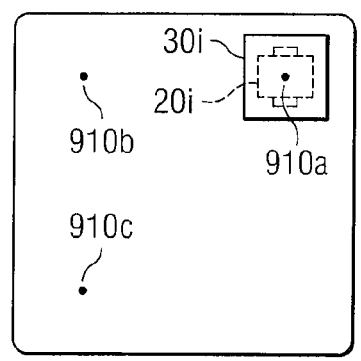

FIG. 20A shows a starting location of both mobile drive unit 20*i* and inventory holder 30*i*. Initially, inventory holder 30*i* is located at a point 910*a* in the relevant workspace 870, and mobile drive unit 20*i* is located at a point 910*b*. As shown by FIG. 20B, mobile drive unit 20*i* moves to the location of inventory holder 30*i* at point 910*a*. At this point, mobile drive unit 20*i* has yet to dock with inventory holder 30*i*.

Figure 20C:
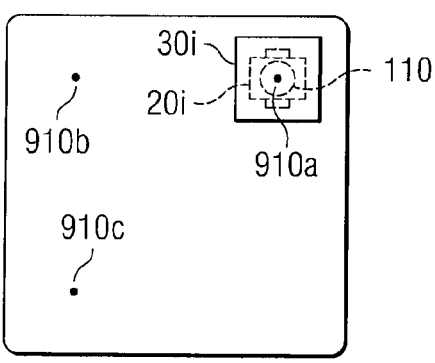
Figure 20D:
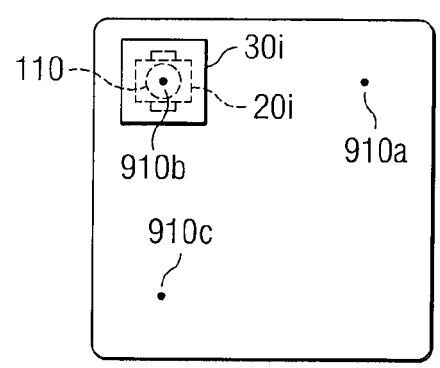

In the illustrated example, mobile drive unit 20*i* is configured to dock with inventory holder 30*i* by positioning itself underneath inventory holder 30*i* and raising a docking head of mobile drive unit 20*i*. Thus, as indicated by the outline of docking head 110, FIG. 20C illustrates mobile drive unit 20 docking with inventory holder 30*i*. Mobile drive unit 20*i* then propels itself and inventory holder 30*i* in a first direction to point 910*b* as shown in FIG. 20D.

Figure 20E:
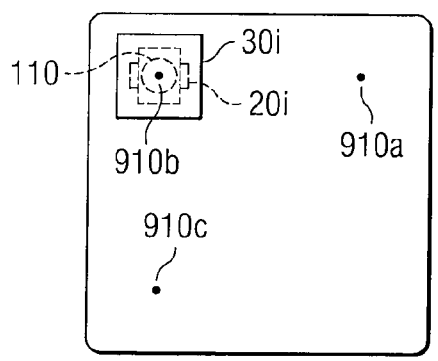

At point 910*b*, mobile drive unit 20 rotates from the first direction to a second direction, as shown in FIG. 20E. As indicated by the outline of docking head 110, mobile drive unit 20, in the illustrated example, remains docked with inventory holder 30 throughout the rotation. For example, in particular embodiments, mobile drive unit 20*i* may, after docking with inventory holder 30*i*, transport inventory holder 30*i* with a rotation lock engaged that prevents mobile drive unit 20 from rotating independently from inventory holder 30*i*. In such embodiments, when mobile drive unit 20*i* attempts to turn a corner, mobile drive unit 20*i*, mobile drive unit 20*i* may release the rotation lock, allowing the remainder of mobile drive unit 20 to rotate independently from docking head 110. Thus, in such embodiments, mobile drive unit 20 may be able to rotate while docked with inventory holder 30 but without rotating inventory holder 30.

Figure 20F:
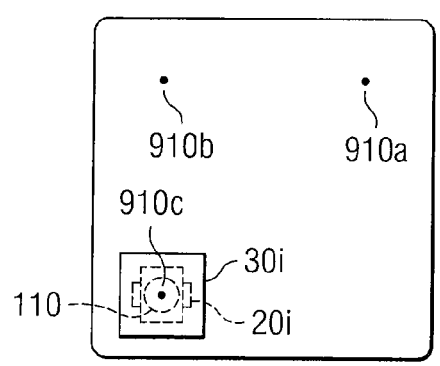

After rotating, mobile drive unit 20*i* propels mobile drive unit 20*i* and inventory holder 30*i* in the second direction. As a result, mobile drive unit 20 moves to point 910*c* as shown in FIG. 20F. Depending on the task mobile drive unit 20*i* is completing, mobile drive unit 20 may then undock from inventory holder 30*i*, rotate inventory holder 30*i* in a designated rotation area 892 for presentation of a particular face, and/or perform any other appropriate actions to complete its assigned task.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. A method for transporting inventory items, comprising:
calculating, for each of a plurality of cells in a workspace, a cost associated with a mobile drive unit moving through that cell;
calculating a cost associated with transporting a mobile drive unit between a first point and a second point using particular conveyance equipment;
calculating a first path cost associated with a first path between an initial location and a destination location based, at least in part, on a sum of the cost associated with each of the cells the first path traverses;
calculating a second path cost associated with a second path between the initial location and the destination location, the second path traversing the first point and the second point, based, at least in part, on a sum of the cost associated with each of the cells the second path traverses and the cost associated with transporting the mobile drive unit using the conveyance equipment;
selecting one of the first path and the second path based on the first path cost and the second path cost; and
transmitting information identifying the selected path to a mobile drive unit.

2. The method of claim 1, wherein calculating, for each of the plurality of cells in the workspace, the cost associated with a mobile drive unit moving through that cell comprises calculating, for each of the plurality of cells in the workspace, a cost based, at least in part, on an amount of time required for the mobile drive unit to move across the cell.

3. The method of claim 1, wherein calculating, for each of the plurality of cells in the workspace, the cost associated with a mobile drive unit moving through that cell comprises calculating, for each of the plurality of cells in the workspace, a cost based, at least in part, on a frequency with which mobile drive units move across the cell.

4. The method of claim 1, wherein calculating, for each of the plurality of cells in the workspace, the cost associated with a mobile drive unit moving through that cell comprises calculating, for each of the plurality of cells in the workspace, a cost based, at least in part, on a frequency with which a particular inventory holder associated with the cell is involved in inventory requests processed by the mobile drive units.

5. The method of claim 1, wherein calculating the cost associated with transporting the mobile drive unit between the first point and the second point using the conveyance equipment comprises calculating a cost based, at least in part, on a time required to transport the mobile drive unit between the first point and the second point using the conveyance equipment.

6. The method of claim 1, wherein calculating the cost associated with transporting the mobile drive unit between the first point and the second point using the conveyance equipment comprises calculating a cost based, at least in part, on a frequency with which mobile drive units utilize the conveyance equipment.

7. The method of claim 1, wherein calculating the cost associated with transporting the mobile drive unit between the first point and the second point using the conveyance equipment comprises calculating the cost based, at least in part, on whether a particular inventory item is held only by inventory holders currently stored in a portion of the workspace associated with the second point.

8. The method of claim 1, further comprising:
moving the mobile drive unit along the selected path to an inventory holder;
docking the mobile drive unit with the inventory holder; and
moving the inventory holder.

9. A system for transporting inventory items, comprising:
a mobile drive unit;
a plurality of inventory holders;
a workspace comprising a plurality of workspace cells;
conveyance equipment operable to transport the mobile drive unit between a first point and a second point; and
a management module operable to:
calculate, for each of a plurality of cells in a workspace, a cost associated with a mobile drive unit moving through that cell;
calculate a cost associated with transporting a mobile drive unit between a first point and a second point using the conveyance equipment;
calculate a first path cost associated with a first path between an initial location and a destination location based, at least in part, on a sum of the cost associated with each of the cells the first path traverses;
calculate a second path cost associated with a second path between the initial location and the destination location, the second path traversing the first point and the second point, based, at least in part, on a sum of the cost associated with each of the cells the second path traverses and the cost associated with transporting the mobile drive unit using the conveyance equipment;
select one of the first path and the second path based on the first path cost and the second path cost; and
transmit information identifying the selected path to a mobile drive unit.

10. The system of claim 9, wherein the management module is operable to calculate, for each of the plurality of cells in the workspace, the cost associated with the mobile drive unit moving through that cell by calculating, for each of the plurality of cells in the workspace, a cost based, at least in part, on an amount of time required for the mobile drive unit to move across the cell.

11. The system of claim 9, wherein the management module is operable to calculate, for each of the plurality of cells in the workspace, the cost associated with a mobile drive unit moving through that cell by calculating, for each of the plurality of cells in the workspace, a cost based, at least in part, on a frequency with which mobile drive units move across the cell.

12. The system of claim 9, wherein the management module is operable to calculate, for each of the plurality of cells in the workspace, the cost associated with a mobile drive unit moving through that cell by calculating, for each of the plurality of cells in the workspace, a cost based, at least in part, on a frequency with which a particular inventory holder associated with the cell is involved in inventory requests processed by the mobile drive units.

13. The system of claim 9, wherein the management module is operable to calculate the cost associated with transporting the mobile drive unit between the first point and the second point using the conveyance equipment comprises calculating a cost based, at least in part, on a time required to transport the mobile drive unit between the first point and the second point using the conveyance equipment.

14. The system of claim 9, wherein the management module is operable to calculate the cost associated with transporting the mobile drive unit between the first point and the second point using the conveyance equipment by calculating a cost based, at least in part, on a frequency with which mobile drive units utilize the conveyance equipment.

15. The system of claim 9, wherein the management module is operable to calculate the cost associated with transporting the mobile drive unit between the first point and the second point using the conveyance equipment by calculating the cost based, at least in part, on whether a particular inventory item is held only by inventory holders currently stored on in a portion of the workspace associated with the second point.

16. The system of claim 9, wherein the mobile drive unit is further operable to:
move the mobile drive unit along the selected path to one of the inventory holders;
dock with the inventory holder; and
move the inventory holder.

17. A management module for managing mobile drive units, the management module operable to:
calculate, for each of a plurality of cells in a workspace, a cost associated with a mobile drive unit moving through that cell;
calculate a cost associated with transporting a mobile drive unit between a first point and a second point using particular conveyance equipment;
calculate a first path cost associated with a first path between an initial location and a destination location based, at least in part, on a sum of the cost associated with each of the cells the first path traverses;
calculate a second path cost associated with a second path between the initial location and the destination location, the second path traversing the first point and the second point, based, at least in part, on a sum of the cost associated with each of the cells the second path traverses and the cost associated with transporting the mobile drive unit using the conveyance equipment;
select one of the first path and the second path based on the first path cost and the second path cost; and
transmit information identifying the selected path to a mobile drive unit.

18. A system for managing mobile drive units, comprising:
means for calculating, for each of a plurality of cells in a workspace, a cost associated with a mobile drive unit moving through that cell;
means for calculating a cost associated with transporting a mobile drive unit between a first point and a second point using particular conveyance equipment;
means for calculating a first path cost associated with a first path between an initial location and a destination location based, at least in part, on a sum of the cost associated with each of the cells the first path traverses;

means for calculating a second path cost associated with a second path between the initial location and the destination location, the second path traversing the first point and the second point, based, at least in part, on a sum of the cost associated with each of the cells the second path traverses and the cost associated with transporting the mobile drive unit using the conveyance equipment;

means for selecting one of the first path and the second path based on the first path cost and the second path cost; and means for transmitting information identifying the selected path to a mobile drive unit.

* * * * *